US009034816B2

(12) United States Patent
Scheibel et al.

(10) Patent No.: US 9,034,816 B2
(45) Date of Patent: May 19, 2015

(54) BIOPOLYMER HAVING EXCELLENT TENSILE STRENGTH, EXTENSIBILITY AND TOUGHNESS

(71) Applicant: AMSilk GmbH, Planegg/Martinsried (DE)

(72) Inventors: Thomas Scheibel, Bayreuth (DE); Felix Bauer, Weidenberg (DE)

(73) Assignee: AMSilk GmbH, Planegg/Martinsried (DE)

( * ) Notice: Subject to any disclaimer, the term of this patent is extended or adjusted under 35 U.S.C. 154(b) by 0 days.

(21) Appl. No.: 13/742,636

(22) Filed: Jan. 16, 2013

(65) Prior Publication Data

US 2013/0225476 A1 Aug. 29, 2013

(30) Foreign Application Priority Data

Jan. 16, 2012 (EP) .................................... 12151315

(51) Int. Cl.

*C07K 14/00* (2006.01)
*A61K 8/00* (2006.01)
*C07K 14/435* (2006.01)
*A61K 38/00* (2006.01)

(52) U.S. Cl.

CPC ................ *C07K 14/00* (2013.01); *A61K 38/00* (2013.01); *C07K 14/43563* (2013.01)

(58) Field of Classification Search

None

See application file for complete search history.

(56) References Cited

U.S. PATENT DOCUMENTS

2013/0225476 A1* 8/2013 Scheibel et al. ............... 514/1.1

OTHER PUBLICATIONS

Allmeling, et al., “Use of Spider Silk Fiber as an Innovative Material in a Biocompatible Artificial Nerve Conduit”, J. Cell. Mol. Med., vol. 10:3; 770-777 (2006).
Allmeling, et al., “Spider Silk Fibers in Artificial Nerve Constructs Promote Peripheral Nerve Regeneration”, Cell Prolif., vol. 41:408-420 (2008).
Craig, “Evolution of Arthropod Silks” Annu. Rev. Entomol., 42:231-67 (1997).
Hagenau, et al., “Mussel Collagen Molecules with Silk-lik Domains as Load-bearing elements in Distal Byssal Threads”, J. Struc. Bio., vol. 175:339-347 (2011).
Hardy, et al., “Polymeric Materials based on Silk Proteins”, Polymer, vol. 49:4309-4327 (2008).
Hepburn, et al., “Extensometric Properties of Insect Fibroins: the Green Lacewing Cross-β, Honeybee α-Helical and Greater Waxmoth Parallel-α Conformations”, Insect Biochem., vol. 9:69-77 (1979).
Hu, et. al., Determining Beta-Sheet Crystallinity in Fibrous Proteins by Thermal Analysis and Infrared Spectroscopy, Macromolecules, vol. 39:6161-6170 (2006).
Huemmerich, et al., “Primary Structure Elements of Spider Dragline Silks and their Contributions to Protein Solubility”, Biochemistry, vol. 43:13604-13612 (2004).
Korz, et al., “Simple Fed-Batch Technique for High Cell Density Cultivation of *Escherichia coli*” J. Biotech., vol. 39:59-65 (1995).
Lammel, et al., “Recombinant Spider Silk Particles as Drug Delivery Vehicles”, Biomaterials, vol. 32:2233-2240 (2011).
Leal-Egaña, et al., “Silk-based materials for biomedical applications”, University of Bayreuth, Bayreuth Germany: p. 1-21.
Lucas, et al., “Amino-Acid Composition of Silk of Chrysopa Egg-Stalks”, Nature, vol. 179 No. 4566:906-7 (May 4, 1957).
Moore, et al., “Vibrational Analysis of Peptides, Polypeptides, and Proteins. II β-Poly(L-alanine) and β-Poly(L-alanylgycine”, Biopolymers, vol. 15:2465-2483 (1976).
Numata, et al, “Silk-based Delivery System of Bioactive Molecules”, Adv. Drug Delivery Rev., vol. 62;1497-1508 (2010).
Parker, et al., “The Silk of the Egg-Stalk of the Green Lacy-Wing Fly”, Nature, vol. 179 No. 4566:905-6 (May 4, 1957).
Plaza, et al., “Thermo-Hygro-Mechanical Behavior of Spider Dragline Silk: Glassy and Rubber States”, J. Polymer Sci. Part B Polymer Physics, vol. 44, 994-999 (2006).
Schäfer et al., “Spider Silk Softening by Water Uptake: an AFM Study”, Eur Biophys J. (2007).
Spiess, et al., “Recombinant Spider Silk Proteins for Applications in Biomaterials”, Macromol. Biosci., vol. 10: 998-1007 (2010).
Vehoff, et al., “Mechanical Properties of Spider Dragline Silk: Humidity, Hysteresis, and Relaxation”, Biophys J. BioFAST, 1-23 (Aug. 31, 2007).
Vendrely, et al., “Biotechnological Production of Spider-Silk Proteins Enables New Applications”, Macromol. Biosci., vol. 7:401-409 (2007).
Weisman, et al., “Fifty Years Later: The Sequence, Structure and Function of Lacewing Cross-beta Silk”<J. Struc. Bio., vol. 168:467-475 (2009).
Xia, et al., “Native-sized Recombinant Spider Silk Protein Produced in Metalbolically Engineered *Escherichia coli* Results in a Strong Fiber”, PNAS, vol. 107, No. 32:14059-14063 (Aug. 10, 2010).
Yao, et al., “Artificial Spinning and Characterization of Silk Fiber from *Bombyx mori* Silk Fibroin in Hexafluoroacetone Hydrate”, Macromolecules, vol. 35-6-9 2002.
Zhang, et al., “Stable Extracellular Matrix Protein Patterns Guide the Orientation of Osteoblast-like Cells”, Adv. Funct. Mater., vol. 21:4079-4087 (2011).

* cited by examiner

*Primary Examiner* — Maury Audet
(74) *Attorney, Agent, or Firm* — Morgan, Lewis & Bockius LLP

(57) ABSTRACT

The present invention relates to a biopolymer having excellent tensile strength, extensibility and toughness. The present invention further relates to a nucleic acid molecule encoding the biopolymer of the invention, a vector comprising the nucleic acid molecule of the invention and a non-human host transformed with the vector of the invention. Furthermore, the present invention relates to methods for producing a biopolymer of the invention and to foams, films, gels, coatings, particles, capsules, springs or nonwoven mats as well as fibers comprising or consisting of the biopolymer of the invention. The present invention also relates to a method of producing fibers and the biopolymer of the invention for use in medicine, agriculture, cosmetics as well as surface, paper, leather and/or textile processing.

23 Claims, 17 Drawing Sheets

SEQUENCE LISTING

```
<160> NUMBER OF SEQ ID NOS: 68

<210> SEQ ID NO 1
<211> LENGTH: 48
<212> TYPE: PRT
<213> ORGANISM: artificial sequence
<220> FEATURE:
<223> OTHER INFORMATION: /note="Description of artificial sequence:
      amino acid sequence of repeat"

<400> SEQUENCE: 1
```

```
Gly Ser Ala Gly Ala Ser Ser Asn Gly Ser Ser Ala Thr Ala Ser Lys
1               5                   10                  15

Gly Ser Ala Gly Ala Thr Ser Asn Gly Ser Thr Ala Val Ala Ser Lys
            20                  25                  30

Gly Ser Ala Gly Ala Ser Ser Gly Asn Ser Thr Ala Ser Ala Thr Lys
        35                  40                  45


<210> SEQ ID NO 2
<211> LENGTH: 288
<212> TYPE: DNA
<213> ORGANISM: artificial sequence
<220> FEATURE:
<223> OTHER INFORMATION: /note="Description of artificial sequence:
      nucleic acid sequence of repeat"

<400> SEQUENCE: 2

ggtagtgccg gtgcaagcag caatggtagc agcgcaaccg caagcaaagg ttcagccggt      60

gcaacctcaa atggtagcac cgcagttgcc agcaaaggta gcgcaggcgc aagcagcggt     120

aatagcaccg caagcgcgac caaaggtagt gcgggtgcca gctcaaatgg ttcaagcgcc     180

accgcatcaa aaggtagcgc tggtgcgacc agcaatggtt caaccgcagt tgcgtcaaaa     240

ggttctgcgg gtgcaagcag tggtaattca accgcatcag caaccaaa                  288


<210> SEQ ID NO 3
<211> LENGTH: 153
<212> TYPE: PRT
<213> ORGANISM: Mallada signata

<400> SEQUENCE: 3

Asn Tyr Asn Ile Trp Ser Asn Val Asn Ala His Pro Thr Asp Cys Gly
1               5                   10                  15

Asn Ser Gly Gly Ser Ser Gly Ser Ser Ala Ala Ser Gly Ala Ala Ser
            20                  25                  30

Ser Ser Gly Ser Gly Ser Ala Ala Gly Ser Gly Ala Ala Ser Gly Ser
        35                  40                  45

Gly Ala Ala Ser Gly Ser Gly Ala Ala Ser Gly Ser Gly Ala Ala Ser
    50                  55                  60

Gly Ser Gly Ala Ala Ser Gly Ser Gly Ala Ala Ser Gly Ser Gly Ala
65                  70                  75                  80

Ala Ser Gly Ser Gly Ala Ala Ser Gly Ser Gly Ala Ala Ser Gly Ser
                85                  90                  95

Gly Ala Ala Ser Gly Ser Gly Ala Ala Ser Gly Ser Gly Ala Ala Ser
            100                 105                 110

Gly Ser Gly Ala Ala Ser Gly Ser Gly Ala Ala Ser Gly Ser Gly Ser
        115                 120                 125

Ala Ser Gly Ser Gly Ser Ala Ser Gly Ser Gly Ser Ser Ser Gly Ser
    130                 135                 140

Gly Ser Ser Gly Cys Gly Ser Gly Gly
145                 150


<210> SEQ ID NO 4
<211> LENGTH: 129
<212> TYPE: PRT
<213> ORGANISM: Mallada signata

<400> SEQUENCE: 4

Gly Cys Asn Val Ile Ala Tyr Pro Thr Ala Ser Cys Gly Asp Ser Gly
1               5                   10                  15
```

```
Ser Gly Ser Ala Ala Ser Ser Gly Ala Ala Ser Ser Ser Gly Ser Gly
            20                  25                  30

Ser Ala Ser Gly Ser Gly Ala Ala Ser Gly Ser Gly Ser Ala Ser Gly
        35                  40                  45

Ser Gly Ala Ala Ser Gly Ser Gly Ser Ala Ala Gly Ser Gly Ala Ala
    50                  55                  60

Ser Gly Ser Gly Ala Ala Ser Gly Ser Gly Ser Ala Ser Gly Ser Gly
65                  70                  75                  80

Ser Ala Ser Gly Ser Gly Ser Ala Ala Gly Ser Gly Ala Ala Ser Gly
                85                  90                  95

Ser Gly Ser Ala Ser Gly Ser Gly Ser Ser Ser Ser Gly Ser Ser Ser
            100                 105                 110

Ser Gly Ser Ser Gly Gly Cys Gly Gly Gly Ser Gly Ser Ala Ser Ser
        115                 120                 125

Gly


<210> SEQ ID NO 5
<211> LENGTH: 153
<212> TYPE: PRT
<213> ORGANISM: Latrodectus hesperus

<400> SEQUENCE: 5

Met Thr Thr Met Asn Trp Ser Thr Arg Leu Val Leu Ser Ile Leu Val
1               5                   10                  15

Val Leu Cys Thr Gln Ser Leu Cys Ala Leu Gly Gln Ala Asn Thr Pro
            20                  25                  30

Trp Ser Ser Lys Glu Asn Ala Asp Ala Phe Ile Gly Ala Phe Met Asn
        35                  40                  45

Ala Ala Ser Gln Ser Gly Ala Phe Ser Ser Asp Gln Ile Asp Asp Met
    50                  55                  60

Ser Val Ile Ser Asn Thr Leu Met Ala Ala Met Asp Asn Met Gly Gly
65                  70                  75                  80

Arg Ile Thr Gln Ser Lys Leu Gln Ala Leu Asp Met Ala Phe Ala Ser
                85                  90                  95

Ser Val Ala Glu Ile Ala Val Ala Asp Gly Gln Asn Val Gly Ala Ala
            100                 105                 110

Thr Asn Ala Ile Ser Asp Ala Leu Arg Ser Ala Phe Tyr Gln Thr Thr
        115                 120                 125

Gly Val Val Asn Asn Gln Phe Ile Thr Gly Ile Ser Ser Leu Ile Gly
    130                 135                 140

Met Phe Ala Gln Val Ser Gly Asn Glu
145                 150


<210> SEQ ID NO 6
<211> LENGTH: 153
<212> TYPE: PRT
<213> ORGANISM: Latrodectus hesperus

<400> SEQUENCE: 6

Thr Thr Thr Met Thr Trp Ser Thr Arg Leu Ala Leu Ser Phe Leu Phe
1               5                   10                  15

Val Leu Cys Thr Gln Ser Leu Tyr Ala Leu Ala Gln Ala Asn Thr Pro
            20                  25                  30

Trp Ser Ser Lys Ala Asn Ala Asp Ala Phe Ile Asn Ser Phe Ile Ser
        35                  40                  45

Ala Ala Ser Asn Thr Gly Ser Phe Ser Gln Asp Gln Met Glu Asp Met
```

```
    50                  55                  60

Ser Leu Ile Gly Asn Thr Leu Met Ala Ala Met Asp Asn Met Gly Gly
65                  70                  75                  80

Arg Ile Thr Pro Ser Lys Leu Gln Ala Leu Asp Met Ala Phe Ala Ser
                85                  90                  95

Ser Val Ala Glu Ile Ala Ala Ser Glu Gly Gly Asp Leu Gly Val Thr
            100                 105                 110

Thr Asn Ala Ile Ala Asp Ala Leu Thr Ser Ala Phe Tyr Gln Thr Thr
        115                 120                 125

Gly Val Val Asn Ser Arg Phe Ile Ser Glu Ile Arg Ser Leu Ile Gly
    130                 135                 140

Met Phe Ala Gln Ala Ser Ala Asn Asp
145                 150


<210> SEQ ID NO 7
<211> LENGTH: 153
<212> TYPE: PRT
<213> ORGANISM: Nephila inaurata madagascariensis

<400> SEQUENCE: 7

Met Ser Trp Ser Thr Leu Ala Leu Ala Ile Ile Ala Val Leu Ser Thr
1               5                   10                  15

Gln Cys Ile Phe Ile Ala Gly Gln Ala Asn Thr Pro Trp Ser Asp Thr
            20                  25                  30

Ala Thr Ala Asp Ala Phe Ile Gln Asn Phe Leu Gly Ala Val Ser Gly
        35                  40                  45

Ser Gly Ala Phe Thr Pro Asp Gln Leu Asp Asp Met Ser Thr Val Gly
    50                  55                  60

Asp Thr Ile Met Ser Ala Met Asp Lys Met Ala Arg Ser Asn Lys Ser
65                  70                  75                  80

Ser Lys Ser Lys Leu Gln Ala Leu Asn Met Ala Phe Ala Ser Ser Met
                85                  90                  95

Ala Glu Ile Ala Ala Val Glu Gln Gly Gly Gln Ser Met Asp Val Lys
            100                 105                 110

Thr Asn Ala Ile Ala Asn Ala Leu Asp Ser Ala Phe Tyr Met Thr Thr
        115                 120                 125

Gly Ser Thr Asn Gln Gln Phe Val Asn Glu Met Arg Ser Leu Ile Asn
    130                 135                 140

Met Leu Ser Ala Ala Ala Val Asn Glu
145                 150


<210> SEQ ID NO 8
<211> LENGTH: 154
<212> TYPE: PRT
<213> ORGANISM: Argiope trifasciata

<400> SEQUENCE: 8

Met Asn Trp Ser Ile Arg Leu Ala Leu Leu Gly Phe Val Val Leu Ser
1               5                   10                  15

Thr Gln Thr Val Phe Ser Ala Gly Gln Gly Ala Thr Pro Trp Glu Asn
            20                  25                  30

Ser Gln Leu Ala Glu Ser Phe Ile Ser Arg Phe Leu Arg Phe Ile Gly
        35                  40                  45

Gln Ser Gly Ala Phe Ser Pro Asn Gln Leu Asp Asp Met Ser Ser Ile
    50                  55                  60

Gly Asp Thr Leu Lys Thr Ala Ile Glu Lys Met Ala Gln Ser Arg Lys
```

```
65                  70                  75                  80

Ser Ser Lys Ser Lys Leu Gln Ala Leu Asn Met Ala Phe Ala Ser Ser
                85                  90                  95

Met Ala Glu Ile Ala Val Ala Glu Gln Gly Gly Leu Ser Leu Glu Ala
            100                 105                 110

Lys Thr Asn Ala Ile Ala Ser Ala Leu Ser Ala Ala Phe Leu Glu Thr
        115                 120                 125

Thr Gly Tyr Val Asn Gln Gln Phe Val Asn Glu Ile Lys Thr Leu Ile
    130                 135                 140

Phe Met Ile Ala Gln Ala Ser Ser Asn Glu
145                 150


<210> SEQ ID NO 9
<211> LENGTH: 153
<212> TYPE: PRT
<213> ORGANISM: Euprosthenops australis

<400> SEQUENCE: 9

Met Ser Trp Thr Ala Arg Leu Ala Leu Leu Leu Leu Phe Val Ala Cys
1               5                   10                  15

Gln Gly Ser Ser Ser Leu Ala Ser His Thr Thr Pro Trp Thr Asn Pro
            20                  25                  30

Gly Leu Ala Glu Asn Phe Met Asn Ser Phe Met Gln Gly Leu Ser Ser
        35                  40                  45

Met Pro Gly Phe Thr Ala Ser Gln Leu Asp Asp Met Ser Thr Ile Ala
    50                  55                  60

Gln Ser Met Val Gln Ser Ile Gln Ser Leu Ala Ala Gln Gly Arg Thr
65                  70                  75                  80

Ser Pro Asn Lys Leu Gln Ala Leu Asn Met Ala Phe Ala Ser Ser Met
                85                  90                  95

Ala Glu Ile Ala Ala Ser Glu Glu Gly Gly Gly Ser Leu Ser Thr Lys
            100                 105                 110

Thr Ser Ser Ile Ala Ser Ala Met Ser Asn Ala Phe Leu Gln Thr Thr
        115                 120                 125

Gly Val Val Asn Gln Pro Phe Ile Asn Glu Ile Thr Gln Leu Val Ser
    130                 135                 140

Met Phe Ala Gln Ala Gly Met Asn Asp
145                 150


<210> SEQ ID NO 10
<211> LENGTH: 153
<212> TYPE: PRT
<213> ORGANISM: Nephila inaurata madagascariensis

<400> SEQUENCE: 10

Met Ala Cys Phe Thr Ser Ala Val Ile Phe Leu Phe Leu Ala Gln Cys
1               5                   10                  15

Ala Ser Thr Tyr Gly Arg Gly Ile Ile Val Asn Ser Pro Phe Ser Asn
            20                  25                  30

Pro Asn Thr Ala Glu Ala Phe Ala Arg Ser Phe Val Ser Asn Val Val
        35                  40                  45

Ser Ser Gly Glu Phe Gly Ala Gln Gly Ala Glu Asp Phe Asp Asp Ile
    50                  55                  60

Ile Gln Ser Leu Ile Gln Ala Gln Ser Met Gly Lys Gly Arg His Asp
65                  70                  75                  80

Thr Lys Ala Lys Ala Lys Ala Met Gln Val Ala Leu Ala Ser Ser Ile
```

```
                85                  90                  95

Ala Glu Leu Val Ile Ala Glu Ser Ser Gly Gly Asp Val Gln Arg Lys
            100                 105                 110

Thr Asn Val Ile Ser Asn Ala Leu Arg Asn Ala Leu Met Ser Thr Thr
        115                 120                 125

Gly Ser Pro Asn Glu Glu Phe Val His Glu Val Gln Asp Leu Ile Gln
    130                 135                 140

Met Leu Ser Gln Glu Gln Ile Asn Glu
145                 150


<210> SEQ ID NO 11
<211> LENGTH: 80
<212> TYPE: PRT
<213> ORGANISM: Nephila clavipes

<400> SEQUENCE: 11

Met Gly Lys Gly Arg His Asp Thr Lys Ala Lys Ala Lys Ala Met Gln
1               5                   10                  15

Val Ala Leu Ala Ser Ser Ile Ala Glu Leu Val Ile Ala Glu Ser Ser
            20                  25                  30

Gly Gly Asp Val Gln Arg Lys Thr Asn Val Ile Ser Asn Ala Leu Arg
        35                  40                  45

Asn Ala Leu Met Ser Thr Thr Gly Ser Pro Asn Glu Glu Phe Val His
    50                  55                  60

Glu Val Gln Asp Leu Ile Gln Met Leu Ser Gln Glu Gln Ile Asn Glu
65                  70                  75                  80


<210> SEQ ID NO 12
<211> LENGTH: 153
<212> TYPE: PRT
<213> ORGANISM: Argiope bruennichi

<400> SEQUENCE: 12

Met Val Trp Leu Thr Ser Ile Ala Phe Leu Val Gly Phe Leu Gly Ala
1               5                   10                  15

Val Ser Ser Gln Ser Val Ala Val Thr Ala Val Pro Ser Val Phe Ser
            20                  25                  30

Ser Pro Asn Leu Ala Ser Gly Phe Leu Gln Cys Leu Thr Phe Gly Ile
        35                  40                  45

Gly Asn Ser Pro Ala Phe Pro Thr Gln Glu Gln Gln Asp Leu Asp Ala
    50                  55                  60

Ile Ala Gln Val Ile Leu Asn Ala Val Ser Ser Asn Thr Gly Ala Thr
65                  70                  75                  80

Ala Ser Ala Arg Ala Gln Ala Leu Ser Thr Ala Leu Ala Ser Ser Leu
                85                  90                  95

Thr Asp Leu Leu Ile Ala Glu Ser Ala Glu Ser Asn Tyr Ser Asn Gln
            100                 105                 110

Leu Ser Glu Leu Thr Gly Ile Leu Ser Asp Cys Phe Ile Gln Thr Thr
        115                 120                 125

Gly Ser Asp Asn Pro Ala Phe Val Ser Arg Ile Gln Ser Leu Ile Ser
    130                 135                 140

Val Leu Ser Gln Asn Ala Asp Thr Asn
145                 150


<210> SEQ ID NO 13
<211> LENGTH: 98
<212> TYPE: PRT
```

<213> ORGANISM: Argiope bruennichi

<400> SEQUENCE: 13

```
Gln Ala Thr Met Met Trp Phe Thr Thr Val Ala Phe Leu Leu Cys Leu
1               5                   10                  15

Leu Gly Ala Val Ser Ser Gln Ser Val Ala Val Thr Val Pro Ser Val
            20                  25                  30

Phe Ser Ser Pro Asn Leu Ala Ser Gly Phe Leu Gln Cys Leu Thr Phe
        35                  40                  45

Gly Ile Gly Asn Ser Pro Ala Phe Pro Thr Gln Glu Gln Gln Asp Leu
    50                  55                  60

Asp Ala Ile Ala Gln Val Ile Leu Asn Ala Val Ser Ser Asn Thr Gly
65                  70                  75                  80

Ala Thr Ala Ser Ala Arg Ala Gln Ala Leu Ser Thr Ala Leu Ala Ser
                85                  90                  95

Ser Leu
```

<210> SEQ ID NO 14
<211> LENGTH: 158
<212> TYPE: PRT
<213> ORGANISM: Nephila clavata

<400> SEQUENCE: 14

```
Met Val Trp Leu Thr Ser Ile Ala Phe Val Val Ala Leu Leu Gly Ala
1               5                   10                  15

Gln Tyr Asp Ile Val Thr Ala Gln Ala Ile Ser Val Ala Thr Pro Val
            20                  25                  30

Pro Ser Val Phe Ser Ser Pro Ser Leu Ala Ser Gly Phe Leu Gly Cys
        35                  40                  45

Leu Thr Thr Gly Ile Gly Leu Ser Pro Ala Phe Pro Phe Gln Glu Gln
    50                  55                  60

Gln Asp Leu Asp Asp Leu Ala Lys Val Ile Leu Ser Ala Val Thr Ser
65                  70                  75                  80

Asn Thr Asp Thr Ser Lys Ser Ala Arg Ala Gln Ala Leu Ser Thr Ala
                85                  90                  95

Leu Ala Ser Ser Leu Ala Asp Leu Leu Ile Ser Glu Ser Ser Gly Ser
            100                 105                 110

Ser Tyr Gln Thr Gln Ile Ser Ala Leu Thr Asn Ile Leu Ser Asp Cys
        115                 120                 125

Phe Val Thr Thr Thr Gly Ser Asn Asn Pro Ala Phe Val Ser Arg Val
    130                 135                 140

Gln Thr Leu Ile Gly Val Leu Ser Gln Ser Ser Ser Asn Ala
145                 150                 155
```

<210> SEQ ID NO 15
<211> LENGTH: 155
<212> TYPE: PRT
<213> ORGANISM: Latrodectus hesperus

<400> SEQUENCE: 15

```
Met Val Trp Leu Thr Ser Thr Val Leu Leu Ala Ser Leu Leu Gly Thr
1               5                   10                  15

Leu Gly Leu Pro Ala Asn Ser Leu Ser Gly Val Ser Ala Ser Val Asn
            20                  25                  30

Ile Phe Asn Ser Pro Asn Ala Ala Thr Ser Phe Leu Asn Cys Leu Arg
        35                  40                  45
```

-continued

```
Ser Asn Ile Glu Ser Ser Pro Ala Phe Pro Phe Gln Glu Gln Ala Asp
    50                  55                  60

Leu Asp Ser Ile Ala Glu Val Ile Leu Ser Asp Val Ser Ser Val Asn
65                  70                  75                  80

Thr Ala Ser Ser Ala Thr Ser Leu Ala Leu Ser Thr Ala Leu Ala Ser
                85                  90                  95

Ser Leu Ala Glu Leu Leu Val Thr Glu Ser Ala Glu Glu Asp Ile Asp
            100                 105                 110

Asn Gln Val Val Ala Leu Ser Thr Ile Leu Ser Gln Cys Phe Val Glu
        115                 120                 125

Thr Thr Gly Ser Pro Asn Pro Ala Phe Val Ala Ser Val Lys Ser Leu
    130                 135                 140

Leu Gly Val Leu Ser Gln Ser Ala Ser Asn Tyr
145                 150                 155


<210> SEQ ID NO 16
<211> LENGTH: 94
<212> TYPE: PRT
<213> ORGANISM: Mytilus galloprovincialis

<400> SEQUENCE: 16

Gly Gly Phe Gly Gly Ile Gly Gly Ile Gly Pro Gly Gly Ser Val Gly
1               5                   10                  15

Gly Gly Ile Gly Gly Ile Gly Gly Gly Val Gly Gly Val Gly Gly Ile
            20                  25                  30

Gly Gly Val Gly Gly Pro Gly Gly Ile Gly Gly Ile Gly Ile Gly Pro
        35                  40                  45

Gly Phe Gly Gly Gly Phe Gly Pro Gly Ser Ser Ala Ser Gly Ser Gly
    50                  55                  60

Ser Gly Ser Ala Phe Gly Gly Pro Gly Gly Ser Ser Ala Ser Ala Asn
65                  70                  75                  80

Ala Ala Ala Arg Ala Asn Ala Asn Gly Gly Gly Gly Phe Gly
                85                  90


<210> SEQ ID NO 17
<211> LENGTH: 54
<212> TYPE: PRT
<213> ORGANISM: Mytilus galloprovincialis

<400> SEQUENCE: 17

Gly Gly Ser Ala Ser Ala Ala Ala Arg Ala Ala Ala Arg Ala Ser Ala
1               5                   10                  15

Gly Gly Leu Gly Gly Leu Gly Gly Phe Gly Ser Ala Ala Ala Asn Ala
            20                  25                  30

Ala Ala Ala Ala Asn Ala Gly Ala Gly Phe Gly Gly Phe Gly Gly Phe
        35                  40                  45

Gly Gly Phe Gly Gly Val
    50


<210> SEQ ID NO 18
<211> LENGTH: 169
<212> TYPE: PRT
<213> ORGANISM: Mytilus galloprovincialis

<400> SEQUENCE: 18

Ala Ala Ala His Ala Ala Ala Val Ala Asn Ala Leu Gly Gly Gly Gly
1               5                   10                  15

Gly Gly Ser Ala Ser Ala Ala Ala Arg Ala Ala Ala Ala Ala Arg Ala
```

```
            20                  25                  30

Leu Gly Gly Gly Gly Gly Ser Ala Ser Ala Ala Ala Arg Ala Ala Ala
        35                  40                  45

Ala Ala Arg Ala Leu Gly Gly Gly Gly Gly Ala Ser Ala Ala Ala Arg
    50                  55                  60

Ala Ala Ala Ala Ala Ser Ala Leu Gly Gly Gly Gly Gly Phe Gly Gly
65                  70                  75                  80

Leu Gly Gly Leu Gly Gly Gly Ala Gly Gly Leu Gly Gly Leu Gly Gly
                85                  90                  95

Gly Leu Gly Gly Leu Gly Gly Gly Gly Val Gly Gly Gly Gly Val Gly
            100                 105                 110

Gly Gly Gly Val Gly Gly Ile Gly Pro Gly Gly Leu Leu Gly Gly Gly
        115                 120                 125

Gly Gly Pro Gly Ser Ala Gly Ala Phe Gly Asn Gly Asn Ala Ala Ala
    130                 135                 140

Gly Pro Gly Gly Ala Gly Ala Ser Ala Ser Ala Gly Ala Phe Ala Thr
145                 150                 155                 160

Gly Gly Gly Gly Phe Pro Leu Pro Gly
                165


<210> SEQ ID NO 19
<211> LENGTH: 459
<212> TYPE: DNA
<213> ORGANISM: Mallada signata

<400> SEQUENCE: 19

aattacaata tttggagcaa tgtgaatgcc catccgaccg attgtggtaa tagcggtggt      60

agcagcggta gctcagcagc aagcggtgcc gcaagcagca gcggtagtgg tagcgcagca     120

ggtagcggtg cggcatcagg ttcaggtgcg gcaagcggta gcggtgccgc tagtggtagc     180

ggtgctgcaa gcggttctgg tgccgcatca ggtagtggcg cagccagcgg ttcaggcgca     240

gcatctggca gtggtgcggc aagtggctca ggtgccgcaa gtggttccgg tgcggcttct     300

ggttctggcg cagcctcagg ttctggtgct gcctctggca gcggtgctgc gtctggtagt     360

ggcgctgcaa gtggtagcgg cagcgcatct ggtagcggta gtgccagtgg ttcaggtagc     420

agctcaggta gcggtagcag tggttgtggt agcggtggc                            459


<210> SEQ ID NO 20
<211> LENGTH: 387
<212> TYPE: DNA
<213> ORGANISM: Mallada signata

<400> SEQUENCE: 20

ggttgtaatg ttattgcata tccgaccgca agctgtggtg atagcggtag cggtagcgca      60

gcaagcagcg gtgccgcaag cagcagcggt tcaggtagcg caagcggtag tggtgcggca     120

agcggttctg gttcagccag tggtagcggt gcggcatcag gtagcggtag tgccgcaggt     180

tcaggtgccg catcaggttc aggcgcagca agcggcagcg gtagtgcaag tggttctggt     240

agcgcatctg gtagcggttc agcagcaggt tctggtgctg ccagcggcag tggtagcgcc     300

tcaggtagtg gtagcagcag cagtggtagt agcagctcag gtagcagcgg tggttgtggt     360

ggtggtagcg gcagcgccag cagcggt                                         387


<210> SEQ ID NO 21
<211> LENGTH: 459
<212> TYPE: DNA
```

<213> ORGANISM: Latrodectus hesperus

<400> SEQUENCE: 21
atgactacaa tgaattggtc tactcgactt gtgttgtcaa tactcgtagt gctttgcact 60
cagagcctct gtgctctggg acaagcaaac actccgtggt ccagtaaaga aaacgctgac 120
gcttttatag gcgcatttat gaatgctgct tcacaaagtg gagcattttc atcggatcag 180
atagatgata tgtcagttat tagtaataca ttgatggctg caatggacaa catgggtgga 240
agaatcacac aatcaaaatt acaggcttta gatatggctt ttgcatcatc cgtggcagaa 300
atagctgtag ctgatggcca aaacgttgga gccgctacga atgccatatc agacgcatta 360
cggtcagcct tctatcaaac taccggagtg gtaaacaatc aatttattac tgggataagt 420
agcctaattg gcatgtttgc ccaagtatca ggcaatgaa 459

<210> SEQ ID NO 22
<211> LENGTH: 459
<212> TYPE: DNA
<213> ORGANISM: Latrodectus hesperus

<400> SEQUENCE: 22
actactacaa tgacttggtc aactcgactt gccttatcat ttcttttcgt gctctgcact 60
cagagcctgt acgctttggc gcaagccaac acgccatggt caagtaaagc gaatgctgat 120
gcttttatca attcctttat ttcggcagct tcgaatactg gatccttctc ccaagatcag 180
atggaagata tgtcattgat tggtaataca ttaatggcag caatggataa tatgggtgga 240
agaattacgc catccaaatt acaggcttta gatatggctt tcgcatcatc tgtagcagaa 300
attgctgctt cggaaggagg agacttagga gtaacaacaa atgcaattgc agatgcttta 360
acgtcagctt tctatcaaac aaccggagta gttaatagca gatttataag cgaaattaga 420
agtttgattg gcatgtttgc acaggcatct gccaacgat 459

<210> SEQ ID NO 23
<211> LENGTH: 459
<212> TYPE: DNA
<213> ORGANISM: Nephila inaurata madagascariensis

<400> SEQUENCE: 23
atgagttggt ccactctagc tttagcgatt atcgcggtgc ttagcaccca gtgcattttt 60
attgcaggac aagcaaacac accatggagc gacactgcca cagcagatgc tttcattcag 120
aatttcttag gagctgtttc aggaagtgga gcctttactc cagatcaact tgatgatatg 180
tccacagtcg gagataccat catgtcagca atggacaaaa tggctcgcag taacaagagc 240
tccaaatcaa aattacaagc tctaaacatg gctttcgctt catcgatggc agaaattgca 300
gcggtggaac aaggtggtca gagcatggat gtcaaaacaa atgcaattgc caatgctcta 360
gattcagctt tttatatgac aactggttca acaaatcaac agtttgtcaa cgaaatgaga 420
agcttaatta acatgttgag tgcagctgcc gttaatgaa 459

<210> SEQ ID NO 24
<211> LENGTH: 462
<212> TYPE: DNA
<213> ORGANISM: Argiope trifasciata

<400> SEQUENCE: 24
atgaattggt caattcgtct tgctctttta ggtttcgtgg tgctcagcac ccaaactgta 60
ttttctgctg gccagggtgc aactccatgg gagaactcgc aactggcgga gagcttcatc 120
agccgttttt taagattcat aggacaaagc ggagcttttt ccccaaacca actggatgat 180
atgtcttcta ttggagacac cttgaagact gcaattgaaa aaatggctca aagccgaaaa 240
agttctaaat cgaagttgca ggcattaaac atggcatttg cttcctcaat ggccgaaatt 300
gctgtagcag agcagggagg tttaagctta gaagcaaaaa ccaatgccat cgcaagtgcc 360
ctcagtgcag cctttttgga aaccactggc tatgtaaacc aacagtttgt caatgaaata 420
aaaacattaa tatttatgat cgctcaggca tcatcaaatg aa 462

<210> SEQ ID NO 25
<211> LENGTH: 459
<212> TYPE: DNA
<213> ORGANISM: Euprosthenops australis

<400> SEQUENCE: 25
atgagttgga cagcgcgact tgctcttcta ttgctctttg tagcttgcca gggctccagt 60
tctctggcct cacacactac accatggaca aacccaggac tcgcagaaaa cttcatgaac 120
agtttcatgc aaggcctgag ctcgatgcca ggtttcacgg caagccaatt ggatgatatg 180
tcaaccatcg cacaatccat ggtacagtca atacaatcct tggcggcaca aggcaggaca 240
tcaccgaata agctgcaggc ccttaacatg gcttttgcat cttcgatggc agaaatcgcg 300
gcatccgaag aaggaggggg aagcctttcc accaaaacta gctctatagc cagtgcaatg 360
tccaacgcgt ttctgcaaac aactggagtg gtaaaccaac cgttcataaa tgaaataact 420
cagctcgtta gcatgtttgc tcaagcaggt atgaatgat 459

<210> SEQ ID NO 26
<211> LENGTH: 459
<212> TYPE: DNA
<213> ORGANISM: Nephila inaurata madagascariensis

<400> SEQUENCE: 26
atggcctgct ttacctcggc agtgatattt cttttcttag cgcagtgtgc gtcgacgtac 60
ggaaggggga ttatagtcaa ctcccctttc tcaaacccta acacagcgga agcttttgca 120
agatctttcg tgagcaatgt tgtttctagt ggagaatttg gagcccaagg agccgaagac 180
ttcgatgaca taattcaaag tctcatacag gcccagagta tgggcaaagg gcggcatgat 240
acgaaggcca aggcgaaagc gatgcaggta gcccttgctt cttctatagc cgaattggtg 300
atagcagaaa gcagcggagg cgatgtgcaa cgcaaaacca atgttatctc caacgctttg 360
agaaacgcct tgatgtctac aactggaagc ccgaacgaag agttcgtcca tgaagttcaa 420
gacctcatcc agatgttatc tcaagaacag atcaacgag 459

<210> SEQ ID NO 27
<211> LENGTH: 240
<212> TYPE: DNA
<213> ORGANISM: Nephila clavipes

<400> SEQUENCE: 27
atgggcaaag ggcggcatga tacgaaggcc aaggcgaaag cgatgcaggt agcccttgct 60
tcttctatag ccgaattggt tattgcagaa agcagcggag gcgatgtgca acgcaaaacc 120
aacgttatct ccaacgcttt gagaaacgcc ttgatgtcta caacaggcag cccaaacgaa 180
gagttcgtcc atgaagttca agacctcatc cagatgttat ctcaagaaca gatcaacgag 240

<210> SEQ ID NO 28

<211> LENGTH: 459
<212> TYPE: DNA
<213> ORGANISM: Argiope bruennichi

<400> SEQUENCE: 28
atggtttggc tcactagcat agcgttcctc gtaggctttc tgggagcagt gtcgtctcag 60
tcagttgcag ttaccgccgt tccttcagtc ttcagcagtc caaatttggc cagcggcttc 120
cttcaatgtc tcacatttgg aatcggaaat tcccccgcat ttcctactca agaacaacaa 180
gacttggatg ccattgctca ggtgatactc aatgctgttt caagcaacac tggcgctaca 240
gcatcggcca gagctcaagc tttaagtaca gcgcttgcat cttctctgac agatctgctc 300
attgcagagt cggcagaaag caattacagc aatcagttgt ctgaactaac aggaattctc 360
tccgactgtt ttatccaaac tactggatcg gacaacccag catttgtgtc cagaattcaa 420
tctctcattt cagtgctttc ccagaatgca gatacaaat 459

<210> SEQ ID NO 29
<211> LENGTH: 297
<212> TYPE: DNA
<213> ORGANISM: Argiope bruennichi

<400> SEQUENCE: 29
caagcaacta tgatgtggtt cactacagta gcgttcctct tatgcctttt aggagcagtg 60
tcgtcacaat cagttgcagt taccgccgtt ccctcagtct tcagcagtcc aaatttggcc 120
agcggtttcc ttcagtgtct cacatttgga atcggaaatt ctcccgcatt tcctactcaa 180
gaacaacaag acttggatgc cattgcccag gtgatactca atgccgtttc aagcaacact 240
ggcgccacag catcggccag agctcaggct ttaagtacag cgcttgcatc ttctctt 297

<210> SEQ ID NO 30
<211> LENGTH: 474
<212> TYPE: DNA
<213> ORGANISM: Nephila clavata

<400> SEQUENCE: 30
atggtttggc tgacaagcat agcgtttgtt gtggctcttt taggagcaca atacgacatc 60
gtgactgctc aggcaatttc agttgcaact cctgtcccat cagtgttcag tagccctagc 120
cttgcgagtg gtttccttgg atgcctcaca actggtattg gactatctcc agctttcccg 180
tttcaagaac aacaagattt agatgactta gccaaggtaa ttctctccgc agtaaccagt 240
aatactgaca cctcaaagtc agcgagagca caagccttga gcactgcatt agcatcttcc 300
ttagccgacc tactgatatc cgaatcaagt ggaagcagct accaaactca aatatctgcc 360
ctcactaata tcctatccga ttgttttgtc acaacaactg gatcaaacaa tcctgcattt 420
gtatcaagag ttcaaacact tataggagtg ctttctcaaa gcagcagtaa tgca 474

<210> SEQ ID NO 31
<211> LENGTH: 465
<212> TYPE: DNA
<213> ORGANISM: Latrodectus hesperus

<400> SEQUENCE: 31
atggtttggt tgacaagtac tgtgctccta gcatcccttc tgggaacact tggacttcca 60
gccaatagtt tatcaggagt ttctgcctcg gtcaatattt tcaatagccc caatgcagca 120
actagtttcc taaactgtct tagatctaat atagaatctt ctccagcatt cccattccaa 180
gaacaggctg acttagattc tatcgcggaa gtaattcttt cagatgtatc cagtgtgaat 240
accgcaagct cagcaacatc tttagcgcta agtactgctt tagcatcgtc gttggctgaa 300
ctacttgtca ctgaatcagc tgaagaagat attgataatc aggtagtagc tttgtcaaca 360
attctttctc agtgtttcgt agaaaccaca ggatctccca acccagcgtt tgtagcaagt 420
gtaaaatcgc tacttggagt attatcacag tctgcaagca attat 465

<210> SEQ ID NO 32
<211> LENGTH: 282
<212> TYPE: DNA
<213> ORGANISM: Mytilus galloprovincialis

<400> SEQUENCE: 32
ggtggattcg gcggtattgg cggtattggc ccaggaggaa gtgttggagg aggtattggt 60
ggaatcggag gcggcgttgg cggtgttggc ggtattggcg gcgttggtgg accaggcggt 120
attggcggta tcggaatcgg accaggattc ggaggaggat tcggaccagg ttcatcagct 180
agtggatccg gaagtggcag cgcattcggt ggtccaggag gttcaagcgc aagcgcaaac 240
gcagctgcac gtgcaaatgc aaatggtggt ggaggattcg gt 282

<210> SEQ ID NO 33
<211> LENGTH: 633
<212> TYPE: DNA
<213> ORGANISM: Mytilus galloprovincialis

<400> SEQUENCE: 33
atgagatttc cttcaatttt tactgctgtt ttattcgcag catcctccgc attagctgct 60
ccagtcaaca ctacaacaga agatgaaacg gcacaaattc cggctgaagc tgtcatcggt 120
tactcagatt tagaagggga tttcgatgtt gctgttttgc cattttccaa cagcacaaat 180
aacgggttat tgtttataaa tactactatt gccagcattg ctgctaaaga agaaggggta 240
tctctcgaga aaagagaggc tgaagctgac tatcacggta acaaacagta tggcggccga 300
tacggcaaca gattcggagg tggtattggt ggtgcaggag ccgtagccca tgcccatgcc 360
catgcccatg ctagtgccgg agcaaacgga agagcaagag cacatgcacg agccttggcc 420
catgcacatg ccggtggtag cgctgcacat ggacacccag gattcccagt tggtggtagc 480
gcaagcgcag ccgcacgagc agcagcacga gcatcagcag gaggattagg aggactaggt 540
ggattcggat cagcagcagc caatgcagca gcagcagcaa acgcaggagc aggatttggt 600
ggattcggtg gattcggagg attcggagga gtc 633

<210> SEQ ID NO 34
<211> LENGTH: 873
<212> TYPE: DNA
<213> ORGANISM: Mytilus galloprovincialis

<400> SEQUENCE: 34
atgagatttc cttcaatttt tactgctgtt ttattcgcag catcctccgc attagctgct 60
ccagtcaaca ctacaacaga agatgaaacg gcacaaattc cggctgaagc tgtcatcggt 120
tactcagatt tagaagggga tttcgatgtt gctgttttgc cattttccaa cagcacaaat 180
aacgggttat tgtttataaa tactactatt gccagcattg ctgctaaaga agaaggggta 240
tctctcgaga aaagagaggc tgaagctggg agcatcggat atggcaaacc cggatacggt 300
ggtggtagag atttctttaa cggccacgga ggaggtcatg gaggtggaca cggaggtggt 360
catggaggaa gtgcttcagc agcagcccat gcagcagcag ttgcaaatgc tctaggtggc 420

```
ggtggaggag gaagtgcctc agcagcagcc cgagctgcag ctgctgcacg tgctctaggt    480

ggtggtggag gaagtgcctc agcagcagcc cgagctgcag ccgctgcacg tgctcttggt    540

ggtggtggag gtgcatctgc agccgcccgt gccgcagcag ccgcaagtgc tctaggcggc    600

ggtggtggtt ttggaggtct cggcggtctc ggcggaggcg ctggaggcct tggcggactt    660

ggaggtggac ttggcggact cggaggaggt ggagtcggag gaggtggagt cggaggaggt    720

ggagtcggac ctggaggact tttgggcggc ggcggtggcc ctggtagtgc aggtgcattc    780

ggcaacggaa atgcagctgc tggaccagga ggcgctggtg caagcgctag tgcaggagca    840

tttgcaactg gcggaggagg attcccctta cca                                 873


<210> SEQ ID NO 35
<211> LENGTH: 58
<212> TYPE: PRT
<213> ORGANISM: artificial sequence
<220> FEATURE:
<223> OTHER INFORMATION: /note="Description of artificial sequence:
      C-terminal polypeptide"

<400> SEQUENCE: 35

Gly Ser Ala Ser Ala Ser Ser Asp Gly Phe Ser Ala Ala Cys Asp Ser
1               5                   10                  15

Gly Glu Ser Glu Ala Val Asp Lys Ala Asn Leu Ala Ala Ile Ala Asn
            20                  25                  30

Ile Ala Ala Ala Ala Gly Lys Pro Ala Ala Cys Gly Ser Ala Pro Pro
        35                  40                  45

Ser Asp Asp Tyr Tyr Asp Tyr Gly Cys Gly
    50                  55


<210> SEQ ID NO 36
<211> LENGTH: 117
<212> TYPE: PRT
<213> ORGANISM: Mallada signata

<400> SEQUENCE: 36

Gly Ser Ala Ser Gly Ser Ser Gly Gly Cys Gly Ser Gly Gly Ser Ser
1               5                   10                  15

Gly Ser Gly Ser Gly Ser Ala Ser Gly Ser Gly Ser Ala Ser Gly Ser
            20                  25                  30

Gly Ser Ala Ser Gly Ser Gly Ser Ala Ser Gly Ser Gly Ala Ala Ser
        35                  40                  45

Gly Ser Gly Ala Ala Ser Gly Ser Gly Ala Ala Ser Gly Ser Gly Ala
    50                  55                  60

Ala Ser Gly Ser Gly Ala Ala Ser Gly Ser Gly Ala Ala Ser Gly Ser
65                  70                  75                  80

Gly Ala Ala Ser Gly Ser Ala Ala Ala Ser Gly Ala Ala Ser Ser Ser
                85                  90                  95

Gly Ser Ala Ser Gly Ser Gly Ser Gly Ser Gly Ser Ser Asp Asp Ser
            100                 105                 110

Glu Asp Asp Ser Cys
        115


<210> SEQ ID NO 37
<211> LENGTH: 101
<212> TYPE: PRT
<213> ORGANISM: Latrodectus hesperus

<400> SEQUENCE: 37
```

-continued

```
Ala Gly Leu Ala Ser Thr Ala Ala Thr Ser Arg Ile Asn Asp Ile Ala
1               5                   10                  15

Gln Ser Leu Ser Ser Thr Leu Ser Ser Gly Ser Gln Leu Ala Pro Asp
            20                  25                  30

Asn Val Leu Pro Gly Leu Ile Gln Leu Ser Ser Ser Ile Gln Ser Gly
        35                  40                  45

Asn Pro Asp Leu Asp Pro Ala Gly Val Leu Ile Glu Ser Leu Leu Glu
    50                  55                  60

Tyr Thr Ser Ala Leu Leu Ala Leu Leu Gln Asn Ala Gln Ile Thr Thr
65                  70                  75                  80

Tyr Asp Ala Ala Thr Leu Pro Ala Phe Asn Thr Ala Leu Val Asn Tyr
                85                  90                  95

Leu Val Pro Leu Val
            100


<210> SEQ ID NO 38
<211> LENGTH: 98
<212> TYPE: PRT
<213> ORGANISM: Latrodectus geometricus

<400> SEQUENCE: 38

Ser Ala Leu Ala Ala Pro Ala Thr Ser Ala Arg Ile Ser Ser His Ala
1               5                   10                  15

Leu Thr Leu Leu Ser Asn Gly Pro Thr Asn Pro Ala Ser Ile Ser Asn
            20                  25                  30

Val Ile Ser Asn Ala Val Ser Gln Ile Ser Ser Ser Asn Pro Gly Tyr
        35                  40                  45

Ser Ser Cys Asp Ile Leu Val Gln Ala Leu Leu Glu Leu Val Thr Ala
    50                  55                  60

Leu Leu Thr Ile Ile Gly Ser Ser Asn Val Asn Asp Ile Asn Tyr Gly
65                  70                  75                  80

Ser Ser Gly Gln Tyr Ala Gln Met Val Ser Gln Ser Val Gln Asn Val
                85                  90                  95

Phe Gly


<210> SEQ ID NO 39
<211> LENGTH: 98
<212> TYPE: PRT
<213> ORGANISM: Latrodectus hesperus

<400> SEQUENCE: 39

Ser Ala Leu Ala Ala Pro Ala Thr Ser Ala Arg Ile Ser Ser His Ala
1               5                   10                  15

Ser Ala Leu Leu Ser Asn Gly Pro Thr Asn Pro Ala Ser Ile Ser Asn
            20                  25                  30

Val Ile Ser Asn Ala Val Ser Gln Ile Ser Ser Ser Asn Pro Gly Ala
        35                  40                  45

Ser Ala Cys Asp Val Leu Val Gln Ala Leu Leu Glu Leu Val Thr Ala
    50                  55                  60

Leu Leu Thr Ile Ile Gly Ser Ser Asn Ile Gly Ser Val Asn Tyr Asp
65                  70                  75                  80

Ser Ser Gly Gln Tyr Ala Gln Val Val Thr Gln Ser Val Gln Asn Ala
                85                  90                  95

Phe Ala


<210> SEQ ID NO 40
```

```
<211> LENGTH: 87
<212> TYPE: PRT
<213> ORGANISM: Nephila inaurata madagascariensis

<400> SEQUENCE: 40

Ser Arg Val Pro Asp Met Val Asn Gly Ile Met Ser Ala Met Gln Gly
1               5                   10                  15

Ser Gly Phe Asn Tyr Gln Met Phe Gly Asn Met Leu Ser Gln Tyr Ser
            20                  25                  30

Ser Gly Ser Gly Ser Cys Asn Pro Asn Asn Val Asn Val Leu Met Asp
        35                  40                  45

Ala Leu Leu Ala Ala Leu His Cys Leu Ser Asn His Gly Ser Ser Ser
    50                  55                  60

Phe Ala Pro Ser Pro Thr Pro Ala Ala Met Ser Ala Tyr Ser Asn Ser
65                  70                  75                  80

Val Gly Arg Met Phe Ala Tyr
                85


<210> SEQ ID NO 41
<211> LENGTH: 99
<212> TYPE: PRT
<213> ORGANISM: Argiope trifasciata

<400> SEQUENCE: 41

Ser Arg Leu Ser Ser Pro Gly Ala Ala Ser Arg Val Ser Ser Ala Val
1               5                   10                  15

Thr Ser Leu Val Ser Ser Gly Gly Pro Thr Asn Ser Ala Ala Leu Ser
            20                  25                  30

Asn Thr Ile Ser Asn Val Val Ser Gln Ile Ser Ser Ser Asn Pro Gly
        35                  40                  45

Leu Ser Gly Cys Asp Val Leu Val Gln Ala Leu Leu Glu Ile Val Ser
    50                  55                  60

Ala Leu Val His Ile Leu Gly Ser Ala Asn Ile Gly Gln Val Asn Ser
65                  70                  75                  80

Ser Gly Val Gly Arg Ser Ala Ser Ile Val Gly Gln Ser Ile Asn Gln
                85                  90                  95

Ala Phe Ser


<210> SEQ ID NO 42
<211> LENGTH: 82
<212> TYPE: PRT
<213> ORGANISM: Nephila inaurata madagascariensis

<400> SEQUENCE: 42

Ser Arg Leu Ala Ser Pro Asp Ser Gly Ala Arg Val Ala Ser Ala Val
1               5                   10                  15

Ser Asn Leu Val Ser Ser Gly Pro Thr Ser Ser Ala Ala Leu Ser Ser
            20                  25                  30

Val Ile Ser Asn Ala Val Ser Gln Ile Gly Ala Ser Asn Pro Gly Leu
        35                  40                  45

Ser Gly Cys Asp Val Leu Ile Gln Ala Leu Leu Glu Ile Val Ser Ala
    50                  55                  60

Cys Val Thr Ile Leu Ser Ser Ser Ser Ile Gly Gln Val Asn Tyr Gly
65                  70                  75                  80

Ala Ala


<210> SEQ ID NO 43
```

<211> LENGTH: 87
<212> TYPE: PRT
<213> ORGANISM: Nephila clavipes

<400> SEQUENCE: 43

Ser Arg Val Pro Asp Met Val Asn Gly Ile Met Ser Ala Met Gln Gly
1 5 10 15

Ser Gly Phe Asn Tyr Gln Met Phe Gly Asn Met Leu Ser Gln Tyr Ser
20 25 30

Ser Gly Ser Gly Thr Cys Asn Pro Asn Asn Val Asn Val Leu Met Asp
35 40 45

Ala Leu Leu Ala Ala Leu His Cys Leu Ser Asn His Gly Ser Ser Ser
50 55 60

Phe Ala Pro Ser Pro Thr Pro Ala Ala Met Ser Ala Tyr Ser Asn Ser
65 70 75 80

Val Gly Arg Met Phe Ala Tyr
85

<210> SEQ ID NO 44
<211> LENGTH: 99
<212> TYPE: PRT
<213> ORGANISM: Argiope bruennichi

<400> SEQUENCE: 44

Ser Gly Leu Gly Ser Ser Ala Ala Thr Ala Arg Val Ser Ser Leu Ala
1 5 10 15

Asn Ser Phe Ala Ser Ala Ile Ser Ser Ser Gly Gly Ser Leu Ser Val
20 25 30

Pro Thr Phe Leu Asn Leu Leu Ser Ser Val Gly Ala Gln Val Ser Ser
35 40 45

Ser Ser Ser Leu Ser Ser Leu Glu Val Thr Asn Glu Val Leu Leu Glu
50 55 60

Ala Ile Ala Ala Leu Leu Gln Val Ile Asn Gly Gly Ser Ile Thr Ser
65 70 75 80

Val Asp Leu Arg Tyr Val Pro Asn Ala Gln Gln Asp Leu Val Asn Ala
85 90 95

Leu Ser Gly

<210> SEQ ID NO 45
<211> LENGTH: 103
<212> TYPE: PRT
<213> ORGANISM: Argiope bruennichi

<400> SEQUENCE: 45

Ser Gly Leu Gly Ser Ser Ala Ala Thr Ala Arg Val Ser Ser Leu Ala
1 5 10 15

Asn Ser Ile Ala Ser Ala Ile Ser Ser Ser Gly Gly Ser Leu Ser Val
20 25 30

Pro Thr Phe Leu Asn Leu Leu Ser Ser Ile Gly Ala Gln Val Ser Ser
35 40 45

Ser Ser Ser Leu Ser Ser Ser Ser Glu Val Thr Thr Gln Val Leu Leu
50 55 60

Glu Ala Ile Ala Ala Leu Leu Gln Val Ile Asn Gly Ala Gln Ile Thr
65 70 75 80

Ser Val Asn Phe Ser Asn Val Ser Asn Val Asn Arg Ala Leu Val Asp
85 90 95

Ser Leu Val Gly Ser Phe Ala

```
            100


<210> SEQ ID NO 46
<211> LENGTH: 99
<212> TYPE: PRT
<213> ORGANISM: Nephila clavata

<400> SEQUENCE: 46

Ser Gly Leu Ser Ser Ala Ser Ala Ser Ala Arg Val Gly Ser Leu Ala
1               5                   10                  15

Gln Ser Leu Ala Ser Ala Leu Ser Thr Ser Arg Gly Thr Leu Ser Leu
            20                  25                  30

Ser Thr Phe Leu Asn Leu Leu Ser Pro Ile Ser Ser Glu Ile Arg Ala
        35                  40                  45

Asn Thr Ser Leu Asp Gly Thr Gln Ala Thr Val Glu Ala Leu Leu Glu
    50                  55                  60

Ala Leu Ala Ala Leu Leu Gln Val Ile Asn Gly Ala Gln Ile Thr Asp
65                  70                  75                  80

Val Asn Val Ser Ser Val Pro Ser Val Asn Ala Ala Leu Ala Ser Ala
                85                  90                  95

Leu Val Ala


<210> SEQ ID NO 47
<211> LENGTH: 98
<212> TYPE: PRT
<213> ORGANISM: Latrodectus hesperus

<400> SEQUENCE: 47

Ser Ala Leu Ser Ser Pro Thr Thr His Ala Arg Ile Ser Ser His Ala
1               5                   10                  15

Ser Thr Leu Leu Ser Ser Gly Pro Thr Asn Ala Ala Ala Leu Ser Asn
            20                  25                  30

Val Ile Ser Asn Ala Val Ser Gln Val Ser Ala Ser Asn Pro Gly Ser
        35                  40                  45

Ser Ser Cys Asp Val Leu Val Gln Ala Leu Leu Glu Ile Ile Thr Ala
    50                  55                  60

Leu Ile Ser Ile Leu Asp Ser Ser Ser Val Gly Gln Val Asn Tyr Gly
65                  70                  75                  80

Ser Ser Gly Gln Tyr Ala Gln Ile Val Gly Gln Ser Met Gln Gln Ala
                85                  90                  95

Met Gly


<210> SEQ ID NO 48
<211> LENGTH: 152
<212> TYPE: PRT
<213> ORGANISM: Mytilus galloprovincialis

<400> SEQUENCE: 48

Pro Gly Phe Gly Gly Phe Gly Gly Phe Gly Gly Ala Ser Ala Asn Ala
1               5                   10                  15

Gly Ser Ser Ala Asn Ala Asn Ala Gly Gly Pro Gly Gly Ser Ala Gly
            20                  25                  30

Ala Gly Ser Ser Ser Gly Ala Asn Ala Asn Ala Gly Gly Phe Pro Phe
        35                  40                  45

Gly Gly Pro Phe Gly Gly Val Gly Gly Gly Pro Gly Gly Ala Gly Gly
    50                  55                  60

Pro Gly Gly Val Gly Gly Gly Pro Gly Gly Val Gly Gly Gly Val Gly
```

-continued

```
65                  70                  75                  80

Gly Gly Pro Gly Gly Val Gly Gly Gly Val Gly Gly Gly Pro Gly Gly
                85                  90                  95

Ala Gly Gly Leu Gly Gly Phe Gly Gly Phe Gly Gly Gly Ser Ser Ala
            100                 105                 110

Gly Ala Ser Ser Ser Gly Ser Ala Ser Ala Ser Ser Gly Gly Pro Phe
        115                 120                 125

Gly Val Leu Asn Val Gly Pro Gly Gly Gly Ile Gly Gly Gly Ser Ala
    130                 135                 140

Ser Ala Ser Ala Ala Ser Arg Ala
145                 150


<210> SEQ ID NO 49
<211> LENGTH: 143
<212> TYPE: PRT
<213> ORGANISM: Mytilus galloprovincialis

<400> SEQUENCE: 49

Gly Gly Leu Gly Gly Ala Gly Pro Gly Gly Leu Gly Gly Leu Gly Gly
1               5                   10                  15

Gly Leu Gly Gly Leu Gly Gly Gly Leu Gly Gly Leu Gly Gly Ala Gly
            20                  25                  30

Gly Leu Gly Gly Gly Leu Gly Gly Leu Gly Gly Ala Gly Gly Leu Gly
        35                  40                  45

Gly Gly Leu Gly Gly Leu Gly Gly Ala Gly Gly Gly Ala Gly Gly Ala
    50                  55                  60

Gly Gly Ala Gly Gly Ala Gly Ala Ile Ala Ala Ala Ala Ala Gln Ala
65                  70                  75                  80

Ala Ala Ala Ala Gly Ala Gly Gly Asn Gly Gly Ala Ala Gln Ala Ala
                85                  90                  95

Ala Gln Ala Ala Ala Ser Ala Ala Ala Asn Ser Gly Leu Gly Ala Gly
            100                 105                 110

Ala Ala Arg Ala Ala Ala Ser Ala Ala Ala Arg Ala Thr Val Ala Gly
        115                 120                 125

His Gly Ser Gly Thr Ala Ala Ala Ala Ala Asn Ala Ala Ala Gln
    130                 135                 140


<210> SEQ ID NO 50
<211> LENGTH: 99
<212> TYPE: PRT
<213> ORGANISM: Mytilus galloprovincialis

<400> SEQUENCE: 50

Gly Ala Gly Glu Gly Gly Ala Gly Gly Ala Gly Gly Gly Ala Gly Gly
1               5                   10                  15

Ala Gly Gly Leu Gly Gly Gly Ala Gly Gly Ala Gly Gly Leu Gly Gly
            20                  25                  30

Gly Phe Gly Gly Leu Gly Gly Gly Ala Gly Gly Leu Gly Gly Leu Gly
        35                  40                  45

Gly Gly Ala Gly Gly Ala Gly Gly Val Gly Gly Leu Gly Gly Gly Val
    50                  55                  60

Gly Gly Leu Gly Gly Val Gly Gly Leu Gly Phe Gly Gly Ala Gly Ala
65                  70                  75                  80

Ser Ala Gly Ala Gly Ala Asn Ala Gly Ala Gly Gly Ala Gly Gly Ser
                85                  90                  95

Ala Ser Ala
```

<210> SEQ ID NO 51
<211> LENGTH: 171
<212> TYPE: DNA
<213> ORGANISM: Mallada signata

<400> SEQUENCE: 51
ggatctgcct ctgcttcgtc agatggattt tcggcagctt gtgattcagg tgaatcagag 60
gctgtggata aagccaatct tgctgccatt gctaatattg cagcagcggc gggtaaacca 120
gcagcatgtg gttcagctcc cccaagtgac gattattacg attatggatg t 171

<210> SEQ ID NO 52
<211> LENGTH: 174
<212> TYPE: DNA
<213> ORGANISM: artificial sequence
<220> FEATURE:
<223> OTHER INFORMATION: /note="Description of artificial sequence: nucleic acid of C-terminal polypeptide"

<400> SEQUENCE: 52
ggtagcgcaa gcgcaagcag tgatggtttt agcgcagcat gtgatagcgg tgaaagcgaa 60
gcagttgata aagcaaatct ggcagccatt gcaaatattg cagcagcagc aggtaaaccg 120
gcagcctgtg gtagcgcacc tccgagtgat gattattatg attatggttg tggc 174

<210> SEQ ID NO 53
<211> LENGTH: 327
<212> TYPE: DNA
<213> ORGANISM: Mallada signata

<400> SEQUENCE: 53
ggatgtggtt ctggaggctc tagtgggtca ggttctggat cagcctctgg ctctggttca 60
gcttctggtt caggttcagc ctctggctct ggatcagctt ctggttcagg tgcagcctct 120
ggatctggtg cagcctctgg ctctggtgca gcctctggct ctggagcagc ttctggttca 180
ggtgctgcct ctggctctgg agcagcctct ggttctggag cagcatctgg ttcagctgct 240
gcatctggtg ccgcttcgag ctcaggatca gcttcgggat ccggatctgg aagtggatca 300
tcggatgatt ccgaagatga ttcttgc 327

<210> SEQ ID NO 54
<211> LENGTH: 294
<212> TYPE: DNA
<213> ORGANISM: Latrodectus hesperus

<400> SEQUENCE: 54
tcagctttat cttcaccgac aacgcatgct agaatttctt cccatgcatc aactctatta 60
tcaagtgggc caactaatgc ggcagctctt tctaatgtca ttagtaatgc cgtttcccaa 120
gtcagtgcaa gtaatccagg atcttcctct tgtgatgtcc ttgttcaagc acttcttgaa 180
ataattactg cattaattag tatactagat tcctctagtg ttggacaagt taattacggt 240
tcttcaggac agtatgcaca aattgtaggg cagtctatgc aacaggctat gggg 294

<210> SEQ ID NO 55
<211> LENGTH: 294
<212> TYPE: DNA
<213> ORGANISM: Latrodectus hesperus

<400> SEQUENCE: 55
tctgctttgg cagctccagc tacaagcgcg agaatttctt cacacgcctc agctcttctt 60

-continued

```
tcaaatggac ctactaaccc tgcttctatt tcaaacgtta ttagtaatgc tgtatcccaa    120

attagttcca gcaatccagg agcgtctgcg tgtgatgttc tcgttcaagc tcttcttgaa    180

cttgttactg ctttgctcac cattattgga tcatcaaata ttggcagtgt taattatgat    240

tcttcaggcc aatatgcgca agttgttact caatctgttc aaaatgcatt cgct          294


<210> SEQ ID NO 56
<211> LENGTH: 246
<212> TYPE: DNA
<213> ORGANISM: Nephila inaurata madagascariensis

<400> SEQUENCE: 56

tctcgacttg cttctccaga ttcaggcgct agagttgcat ctgctgtttc taacttggta     60

tccagtggtc caactagctc tgctgcctta tcaagcgtca tcagtaacgc tgtgtctcaa    120

attggagcca gtaatcctgg tctctctggt tgcgatgtcc tcattcaagc tctcttggaa    180

atcgtttcgg cttgtgtaac cattctttct tcatctagca ttggtcaagt taattatgga    240

gcggct                                                               246


<210> SEQ ID NO 57
<211> LENGTH: 297
<212> TYPE: DNA
<213> ORGANISM: Argiope trifasciata

<400> SEQUENCE: 57

tcacgcttgt catcacctgg tgctgcttcg agagtttctt ctgccgttac atctttggtg     60

tcaagtggtg gcccaactaa ttctgcagct ttatctaata ctatcagcaa tgttgtttca    120

caaattagtt caagcaatcc tggtctctct ggctgtgatg ttcttgttca agcattactt    180

gaaattgttt cagctttggt acatattctt ggttcagcta acattggaca agttaactcc    240

agcggtgttg ggcgatcagc ttctattgtg ggacaatcta taaaccaagc tttctca       297


<210> SEQ ID NO 58
<211> LENGTH: 261
<212> TYPE: DNA
<213> ORGANISM: Nephila inaurata madagascariensis

<400> SEQUENCE: 58

tcgcgtgttc ccgatatggt gaatggtata atgagtgcta tgcaaggatc tggttttaac     60

taccaaatgt ttggcaatat gctatcacaa tattcttctg gttcagggtc atgcaatcca    120

aataatgtta atgttttgat ggatgctttg ttagctgctt tgcactgtct aagtaaccac    180

ggatcatcat cttttgcacc ttctccaact ccggctgcta tgagtgctta ttctaattct    240

gtaggaagaa tgttcgctta t                                              261


<210> SEQ ID NO 59
<211> LENGTH: 261
<212> TYPE: DNA
<213> ORGANISM: Nephila clavipes

<400> SEQUENCE: 59

tcgcgtgttc ccgatatggt gaatggtata atgagtgcta tgcaaggatc tggttttaac     60

taccaaatgt ttggtaatat gctatcacaa tattcgtctg gttcaggaac atgcaatcca    120

aataatgtta atgttttgat ggatgctttg ttagctgctt tgcactgtct aagtaaccac    180

ggatcatcat cttttgcacc ttctccaact ccggctgcta tgagtgcgta ttctaattct    240
```

```
gtaggaagaa tgttcgctta t                                            261


<210> SEQ ID NO 60
<211> LENGTH: 297
<212> TYPE: DNA
<213> ORGANISM: Argiope bruennichi

<400> SEQUENCE: 60

tcaggcttag gctcatctgc tgccactgcc agggtgagta gtttagccaa ctcctttgct     60

tctgcgattt cttcatctgg aggttccctc agtgttccaa ccttcttgaa tcttctttca    120

tccgttgggg cccaagttag tagtagcagt tctttgagtt ccttggaagt tacaaacgaa    180

gttttacttg aagctattgc ggctctcttg caagttatca acggaggttc aataacatca    240

gttgatctta gatacgttcc gaatgctcag caggatttgg tgaacgcttt atctggt       297


<210> SEQ ID NO 61
<211> LENGTH: 309
<212> TYPE: DNA
<213> ORGANISM: Argiope bruennichi

<400> SEQUENCE: 61

tcaggcttag gttcatctgc tgccactgcc agggtgagta gtttagccaa ctccattgct     60

tctgcgattt cttcatctgg aggttccctc agtgttccaa ccttcttgaa tcttctttca    120

tccattgggg cgcaagttag tagtagcagt tctttgagtt cttcctcgga agttacaacc    180

caagttttac ttgaagctat tgcggcgctc ttgcaagtta tcaacggggc tcaaataact    240

tcagttaatt tttcaaatgt ttcgaatgta aaccgagcac ttgtagattc tcttgtaggt    300

tcatttgct                                                            309


<210> SEQ ID NO 62
<211> LENGTH: 297
<212> TYPE: DNA
<213> ORGANISM: Nephila clavata

<400> SEQUENCE: 62

tccggcttat catcagcgag tgcgagtgca agagttggca gtttagctca atctctggcg     60

tctgcattgt cgacttctcg aggtactttg agtttatcaa ccttcttgaa tctcctctct    120

ccgatttcgt cagaaattcg agccaatact tctcttgatg gaacgcaggc gactgttgaa    180

gctttactgg aagctttagc tgctctcctg caagttatca atggagcaca gataaccgat    240

gtcaatgttt ctagcgtccc cagcgtgaat gcagccctgg cttctgctct tgttgct       297


<210> SEQ ID NO 63
<211> LENGTH: 303
<212> TYPE: DNA
<213> ORGANISM: Latrodectus hesperus

<400> SEQUENCE: 63

gctggattgg cttctactgc agcaacttca agaattaatg acattgcaca aagtttatct     60

tcaactctat cttcaggatc gcaattagct ccagataatg tacttcctgg tctcattcaa    120

ctgtcttcat ccattcaaag cggaaatcct gatttagacc ctgctggtgt tttgatcgag    180

tcattattag aatacacttc cgcactttta gctcttcttc aaaacgctca aattacaact    240

tatgatgctg cgactttacc tgcattcaat acagctcttg taaattacct tgttcccctt    300

gtt                                                                  303
```

<210> SEQ ID NO 64
<211> LENGTH: 456
<212> TYPE: DNA
<213> ORGANISM: Mytilus galloprovincialis

<400> SEQUENCE: 64
ccaggatttg gtggatttgg tggtttcgga ggagcatcag ctaatgcagg aagttcagca 60
aatgcaaatg ctggtggacc cggtggatcc gctggagcag gttcatcatc aggagctaac 120
gcaaacgcag gtggatttcc attcggagga ccatttggag gagtaggagg tggtcctgga 180
ggagcaggag gtcccggagg agtaggaggt ggaccaggcg gagtaggagg cggagtagga 240
ggtggcccag gaggcgtagg aggtggagta ggaggtggcc caggaggagc aggaggatta 300
ggaggatttg gtggatttgg aggaggatct agcgccggag catcatcatc aggatcagca 360
tctgcatcta gcggtggacc attcggggta ctcaatgtag gaccaggagg tggaatcggt 420
ggtggaagtg catcagcatc tgcagcatct agagca 456

<210> SEQ ID NO 65
<211> LENGTH: 630
<212> TYPE: DNA
<213> ORGANISM: Mytilus galloprovincialis

<400> SEQUENCE: 65
ggtggactcg gaggagcagg accaggagga ctcggaggac taggaggtgg actcggagga 60
cttggaggtg gactcggagg attaggagga gcaggaggtt taggtggtgg actcggagga 120
ttaggaggag caggaggttt aggtggtgga ctcggaggat taggaggagc aggaggtgga 180
gcaggtggag caggaggagc aggaggagca ggtgcaatag cagctgcagc agcacaagca 240
gcagcagcag caggagcagg aggaaacggt ggagcagcac aagcagcagc acaagcagca 300
gcatcagcag cagcaaattc aggacttgga gcaggagcag caagagcagc agcatcagca 360
gctgctagag caaccgtagc aggacatgga agtggaaccg ccgcagcagc agccaacgca 420
gccgcacaag cacatgcagc aacacgagga caaggaggat cacacgcaca cgctgccgcc 480
gcagctcacg cagccgcaag tagcgtaatc catggtggtg gacacggtgg acatggtggt 540
gactatcacg gaggcgatgc cggctatcac aaaccaggat atctagaaca aaaactcatc 600
tcagaagagg atctgaatag cgccgtcgac 630

<210> SEQ ID NO 66
<211> LENGTH: 621
<212> TYPE: DNA
<213> ORGANISM: Mytilus galloprovincialis

<400> SEQUENCE: 66
ggtgcaggag aaggcggagc cggaggtgcc ggtggtggtg ctggtggagc cggtggactc 60
ggaggtggag ccggaggagc tggtggactc ggaggtggat tcggaggact cggtggtgga 120
gcaggtggac ttggtggtct cggtggtgga gcaggaggag ctggtggagt cggaggactc 180
ggcggtggag tcggtggact cggaggagtc ggaggattag gatttggagg agccggtgca 240
agtgcaggag caggagcaaa tgcaggagca ggaggtgcag gcggtagtgc cagtgctcat 300
gcccatgcac atgcccatgc atcatcagca ggcggacttg gaggaggatc cgctcacgca 360
catgccgcag cacacgcaca ttcagtaagt cacgccggag gatcacacgc acacgcagct 420
gctgcagcac acgcacattc agtaagtcac gccggaggat cacacgcaca cgcagctgcc 480
gcagcacacg cacatgctgc atctctcgga ggatctactg gaggacactc actgcactac 540

```
aacgatccat tttatggcaa aaaagccgac tatctagaac aaaaactcat ctcagaagag    600

gatctgaata gcgccgtcga c                                              621


<210> SEQ ID NO 67
<211> LENGTH: 48
<212> TYPE: PRT
<213> ORGANISM: artificial sequence
<220> FEATURE:
<223> OTHER INFORMATION: consensus sequence
<220> FEATURE:
<221> NAME/KEY: VARIANT
<222> LOCATION: (3)..(3)
<223> OTHER INFORMATION: Ala in position 3 may be Ser
<220> FEATURE:
<221> NAME/KEY: VARIANT
<222> LOCATION: (4)..(4)
<223> OTHER INFORMATION: Gly in position 4 may be Ser, Thr or Val
<220> FEATURE:
<221> NAME/KEY: VARIANT
<222> LOCATION: (6)..(6)
<223> OTHER INFORMATION: Ser in position 6 may be Gly, Thr or Val
<220> FEATURE:
<221> NAME/KEY: VARIANT
<222> LOCATION: (8)..(8)
<223> OTHER INFORMATION: Asn in position 8 may be Gly, Gln or Asp
<220> FEATURE:
<221> NAME/KEY: VARIANT
<222> LOCATION: (9)..(9)
<223> OTHER INFORMATION: Gly in position 9 may be Asn, provided that at
      least one of positions 8 or 9 is Gly
<220> FEATURE:
<221> NAME/KEY: VARIANT
<222> LOCATION: (11)..(11)
<223> OTHER INFORMATION: Ser in position 11 may be Gly, Thr, Ala or Val
<220> FEATURE:
<221> NAME/KEY: VARIANT
<222> LOCATION: (13)..(13)
<223> OTHER INFORMATION: Thr in position 13 may be Ser or Ala
<220> FEATURE:
<221> NAME/KEY: VARIANT
<222> LOCATION: (15)..(15)
<223> OTHER INFORMATION: Ser in position 15 may be Thr
<220> FEATURE:
<221> NAME/KEY: VARIANT
<222> LOCATION: (17)..(17)
<223> OTHER INFORMATION: Gly in position 17 may be Asp
<220> FEATURE:
<221> NAME/KEY: VARIANT
<222> LOCATION: (18)..(18)
<223> OTHER INFORMATION: Ser in position 18 may be Ala or Gly
<220> FEATURE:
<221> NAME/KEY: VARIANT
<222> LOCATION: (20)..(20)
<223> OTHER INFORMATION: Gly in position 20 may be Ser, Thr, Ala or Val
<220> FEATURE:
<221> NAME/KEY: VARIANT
<222> LOCATION: (22)..(22)
<223> OTHER INFORMATION: Thr in position 22 may be Gly, Ser, Ala or Val
<220> FEATURE:
<221> NAME/KEY: VARIANT
<222> LOCATION: (24)..(24)
<223> OTHER INFORMATION: Asn in position 24 may be Gly
<220> FEATURE:
<221> NAME/KEY: VARIANT
<222> LOCATION: (25)..(25)
<223> OTHER INFORMATION: Gly in position 25 may be Asn, provided that at
      least one of positions 24 or 25 is Gly
<220> FEATURE:
<221> NAME/KEY: VARIANT
<222> LOCATION: (29)..(29)
<223> OTHER INFORMATION: Val in position 29 may be Gly, Ser, Thr, or Ala
<220> FEATURE:
<221> NAME/KEY: VARIANT
<222> LOCATION: (36)..(36)
<223> OTHER INFORMATION: Gly in position 36 may be Ser, Thr, Ala or Val
<220> FEATURE:
<221> NAME/KEY: VARIANT
```

-continued

```
<222> LOCATION: (38)..(38)
<223> OTHER INFORMATION: Ser in position 38 may be Thr, Ala or Val
<220> FEATURE:
<221> NAME/KEY: VARIANT
<222> LOCATION: (40)..(40)
<223> OTHER INFORMATION: Gly in position 40 may be Asn
<220> FEATURE:
<221> NAME/KEY: VARIANT
<222> LOCATION: (41)..(41)
<223> OTHER INFORMATION: Asn in position 41 may be Gly, provided that at
      last one of positions 40 or 41 is Gly
<220> FEATURE:
<221> NAME/KEY: VARIANT
<222> LOCATION: (45)..(45)
<223> OTHER INFORMATION: Ser in position 45 may be Gly, Thr, Ala or Val
<220> FEATURE:
<221> NAME/KEY: VARIANT
<222> LOCATION: (47)..(47)
<223> OTHER INFORMATION: Thr in position 47 may be Ser

<400> SEQUENCE: 67

Gly Ser Ala Gly Ala Ser Ser Asn Gly Ser Ser Ala Thr Ala Ser Lys
1               5                   10                  15

Gly Ser Ala Gly Ala Thr Ser Asn Gly Ser Thr Ala Val Ala Ser Lys
            20                  25                  30

Gly Ser Ala Gly Ala Ser Ser Gly Asn Ser Thr Ala Ser Ala Thr Lys
        35                  40                  45


<210> SEQ ID NO 68
<211> LENGTH: 152
<212> TYPE: PRT
<213> ORGANISM: Mallada signata

<400> SEQUENCE: 68

Asn Tyr Asn Ile Trp Ser Asn Val Asn Ala His Pro Thr Asp Cys Gly
1               5                   10                  15

Asn Ser Gly Gly Ser Ser Gly Ser Ser Ala Ala Ser Gly Ala Ala Ser
            20                  25                  30

Ser Ser Gly Ser Gly Ser Ala Ala Gly Ser Gly Ala Ala Ser Gly Ser
        35                  40                  45

Gly Ala Ala Ser Gly Ser Gly Ala Ala Ser Gly Ser Gly Ala Ala Ser
    50                  55                  60

Gly Ser Gly Ala Ala Ser Gly Ser Gly Ala Ala Ser Gly Ser Gly Ala
65                  70                  75                  80

Ala Ser Gly Ser Gly Ala Ala Ser Gly Ser Gly Ala Ala Ser Gly Ser
                85                  90                  95

Gly Ala Ala Ser Gly Ser Gly Ala Ala Ser Gly Ser Gly Ala Ala Ser
            100                 105                 110

Gly Ser Gly Ala Ala Ser Gly Ser Gly Ala Ala Ser Gly Ser Gly Ser
        115                 120                 125

Ala Ser Gly Ser Gly Ser Ala Ser Gly Ser Gly Ser Ser Ser Gly Ser
    130                 135                 140

Gly Ser Ser Gly Cys Gly Ser Gly
145                 150
```

BIOPOLYMER HAVING EXCELLENT TENSILE STRENGTH, EXTENSIBILITY AND TOUGHNESS

RELATED APPLICATIONS

This application claims priority of EP 12151315.4, filed Jan. 16, 2012, which is incorporated herein by reference in its entirety for all purposes.

The present invention relates to a biopolymer having excellent tensile strength, extensibility and toughness. The present invention further relates to a nucleic acid molecule encoding the biopolymer of the invention, a vector comprising the nucleic acid molecule of the invention and a non-human host transformed with the vector of the invention. Furthermore, the present invention relates to methods for producing a biopolymer of the invention and to foams, films, gels, coatings, particles, capsules, springs or nonwoven mats as well as fibres comprising or consisting of the biopolymer of the invention. The present invention also relates to a method of producing fibres and the biopolymer of the invention for use in medicine, agriculture, cosmetics as well as surface, paper, leather and/or textile processing.

BACKGROUND OF THE INVENTION

Biopolymers such as polyamino acids, polynucleic acids, polyphenols and polysaccharides have evolved over billions of years to carry out a myriad of tasks such as catalysis, molecular recognition or the storage of energy or information. Biopolymers are synthesized from a very limited number of building blocks and it is their complex three-dimensional structures that are responsible for their highly specialized properties. Polyamino acids and polynucleic acids are synthesized in template-directed catalyzed reactions yielding monodisperse linear polymers composed of a specific sequence of monomers; whereas polyphenols and polysaccharides are prepared via untemplated catalyzed reactions yielding polydisperse polymers with a wide variety of potential structures (including linear and branched) depending upon the monomers involved. Biopolymers are commonly occurring structural elements of biological systems. Polysaccharides are the most abundant biopolymers on earth, cellulose and chitin serve as structural elements in plant cell walls and animal exoskeletons; polyphenols such as lignins are important structural elements in wood and other plants; and polyamino acids such as collagen and elastin are the main components of blood vessels, connective tissues and skin in animals and humans.

Polyamino acids (known as polypeptides or proteins) in higher organisms are synthesized from combinations of up to 19 amino acid monomers (—NH—CHR$^1$—CO—) and one imino acid monomer (—NR$^1$—CHR$^2$—CO—), linked via amide bonds (also known as peptide bonds) between the monomers (which are more commonly referred to as residues). In higher organisms, only the L-amino acids are used as monomers, whereas in lower life forms (such as bacteria or lower plants) D-amino acid monomers can also be incorporated. In vivo, polyamino acids are synthesized in a template-directed fashion: first, DNA is used as a template in the synthesis of messenger RNA (mRNA) via a process known as transcription; mRNA can subsequently be used as a template by ribosomes in the synthesis of a sequence-specific polypeptide, this process is known as translation, because the information stored in a polynucleic acid (genetic code) is translated into information in a polyamino acid (functional code).

The sequence of residues in a polypeptide is known as the primary structure. The amino acid residues display different functional groups on the polyamide backbone of the polymer; these functional groups can be categorized as polar, non-polar, aromatic, anionic or cationic. After polymer synthesis, supramolecular interactions (such as hydrogen bonding between the amide bonds in the backbone of the polymer, or π interactions between aromatic groups) determine the local conformation of the polypeptide which is known as the secondary structure—prominent examples of common secondary structures are: α-helices, β-sheets and β-turns. Hydrogen bonds between the hydrogen atom attached to the nitrogen atom of an amide and the carbonyl oxygen atom of the fourth amino acid on the amino-terminal side of the peptide bond encourage the polymer to coil around an axis into an α-helix; each helical twist contains on average 3.6 amino acids and is 5.4 Å in length. α-helix formation is encouraged by ion pair formation between oppositely charged residues 3 or 4 amino acids apart, and π-interactions between similarly spaced aromatic amino acids. Less common are helical twists containing 3 amino acids (known as $3_1$- or $3_{10}$-helices). In certain cases, hydrogen bonding between chains (intrachain or interchain) that are side by side cause the polypeptide chain to adopt a zigzag conformation, known as a β-sheet. Amino acids with small side chains such as glycine and alanine allow stacking of β-sheets, whereas bulkier amino acids discourage this sort of assembly process. Turns and loops are also frequently occurring secondary structures in polypeptides. Particularly common are 180° loops, known as β-turns, which consist of 4 amino acids where the carbonyl oxygen of the first amino acid is hydrogen bonded to the hydrogen on the amine of the fourth amino acid. Importantly, the second and third amino acids do not participate in hydrogen bonding.

Polypeptides therefore contain regions that are either locally disorganized or locally organized dependent upon their primary structure, and covalent or non-covalent cross links between different regions within a polypeptide chain determine the overall three-dimensional arrangement of the polypeptide chain, which is known as the tertiary structure. Further interactions (covalent or non-covalent) between individual polypeptide chains (identical or different) determine a protein's quaternary structure. The process by which polypeptides assume their secondary, tertiary and quaternary structures after polymerization is known as 'folding' and is in some cases aided by accessory proteins. Once the process of folding is complete and the polypeptides are fully assembled into their biologically active conformations, the polypeptides are said to be in their 'native' state.

As mentioned above, biopolymers based on polyamino acids such as collagen and elastin are a major component in nature, often displaying advantageous properties such as excellent tensile strength, extensibility and toughness that render them attractive for applications such as medical or cosmetic uses. However, despite the knowledge about such naturally occurring biopolymers and their properties, the provision of such compounds in amounts suitable for applications remains a challenge. Accordingly, there is still a need to provide such biopolymers yielding structures with advantageous properties such as e.g. excellent tensile strength, extensibility and toughness.

This need is addressed by the provision of the embodiments characterized in the claims.

SUMMARY OF THE INVENTION

The present invention relates to a biopolymer comprising or consisting of at least two repeats of an amino acid sequence comprising or consisting of: (a) the amino acid sequence of formula I: Gly-Ser-$X_1$-$X_2$-Ala-$X_3$-Ser-$X_4$-$X_5$-Ser-$X_6$-Ala-$X_7$-Ala-$X_8$-Lys-$X_9$-$X_{10}$-Ala-$X_{11}$-Ala-$X_{12}$-Ser-$X_{13}$-$X_{14}$-Ser-Thr-Ala-$X_{15}$-Ala-Ser-Lys-Gly-Ser-Ala-$X_{16}$-Ala-$X_{17}$-Ser-$X_{18}$-$X_{19}$-Ser-Thr-Ala-$X_{20}$-Ala-$X_{21}$-Lys (formula I), wherein: $X_1$ is selected from the group consisting of Ala and Ser; $X_2$ and $X_3$ are each independently selected from the group consisting of Gly, Ser, Thr and Val; $X_4$ is selected from the group consisting of Asn, Gly, Gln and Asp; $X_5$, $X_{13}$, $X_{14}$, $X_{18}$ and $X_{19}$ are each independently selected from the group consisting of Gly and Asn; $X_6$, $X_{11}$, $X_{12}$, $X_{15}$, $X_{16}$, and $X_{20}$ are each independently selected from the group consisting of Gly, Ser, Thr, Ala and Val; $X_7$ is selected from the group consisting of Ser, Thr and Ala; $X_8$ and $X_{21}$ are each independently selected from the group consisting of Ser and Thr; $X_9$ is selected from the group consisting of Gly and Asp; $X_{10}$ is selected from the group consisting of Ser, Ala and Gly; and $X_{17}$ is selected from the group consisting of Ser, Thr, Ala and Val; and wherein at least one of and $X_5$ is Gly; at least one of $X_{13}$ and $X_{14}$ is Gly; and at least one of $X_{18}$ and $X_{19}$ is Gly; and/or (b) a variant of the amino acid sequence of (a), wherein the variant differs from the amino acid sequence of (a) in 1 to 10 amino acids and wherein the variations are selected from the group consisting of substitutions, deletions, insertions and/or additions and wherein preferably the variations, e.g. the substitutions, do not or do not substantially reduce the biophysical properties of the biopolymer formed as compared to a biopolymer comprising or consisting of repeats of the amino acid sequence of (a), wherein the biophysical properties are at least one of the ability of the biopolymer to stay in solution, the processability of the biopolymer and the tensile strength, extensibility, Young's modulus/stiffness and/or toughness of fibres produced from the biopolymer of the invention.

The present invention further relates to a nucleic acid molecule encoding the biopolymer of the invention, a vector comprising the nucleic acid molecule of the invention and a non-human host transformed with the vector of the invention.

Furthermore, the present invention relates to methods for producing a biopolymer of the invention and to foams, films, gels, coatings, particles, capsules, springs or nonwoven mats as well as fibres comprising or consisting of the biopolymer of the invention.

The present invention also relates to a method of producing fibres and the biopolymer of the invention for use in medicine, agriculture, cosmetics as well as surface, paper, leather and/or textile processing.

The above overview does not necessarily describe all problems solved by the present invention.

BRIEF DESCRIPTION OF THE FIGURES

The Figures show:

FIG. 2A is a schematic picture of stalk production from the biopolymers of the invention. 1) stalk drawn from the dope to tinfoil using tweezers; 2) relaxation of the stalk by moving of the tinfoil; 3) the stalk contracts during post-treatment at 60° C. and 70% relative humidity; FIG. 2B is a picture of an artificial egg stalk with tinfoil on top (left) and an natural egg stalk with an egg on top (right); FIG. 2C: SEM picture of an artificial egg stalk; FIG. 2D: SEM picture of a natural egg stalk.

FIG. 4A is a microscopic picture of a natural lacewing egg stalk. Top: bright field; bottom: with crossed polarisers; FIG. 2B is microscopic pictures of a artificial egg stalk; Top: bright field; bottom: with crossed polarisers; scale bars: 50 μm FIG. 5A is a stress strain curves of (the best performing) natural and artificial stalks measured at 30% relative humidity. Differences in noise are due to different stalk diameters; FIG. 5B is a SEM picture of the cross sections of a natural stalk (left) and an artificial stalk (right).

FIG. 11A is a light microscopic picture of stripes of N[AS]$_8$C films made by micro channels in PDMS with a width of 10 μm using a concentration of 1% N[AS]$_8$C in formic acid. FIG. 11B is a light microscopic picture of a structured surface/stripes of protein film with fibroblasts one day after seeding. Thin stripes: treated cell culture plate (20 μm); wide stripes: N[AS]$_8$C film (50 μm).

DETAILED DESCRIPTION OF THE INVENTION

Figure 1:
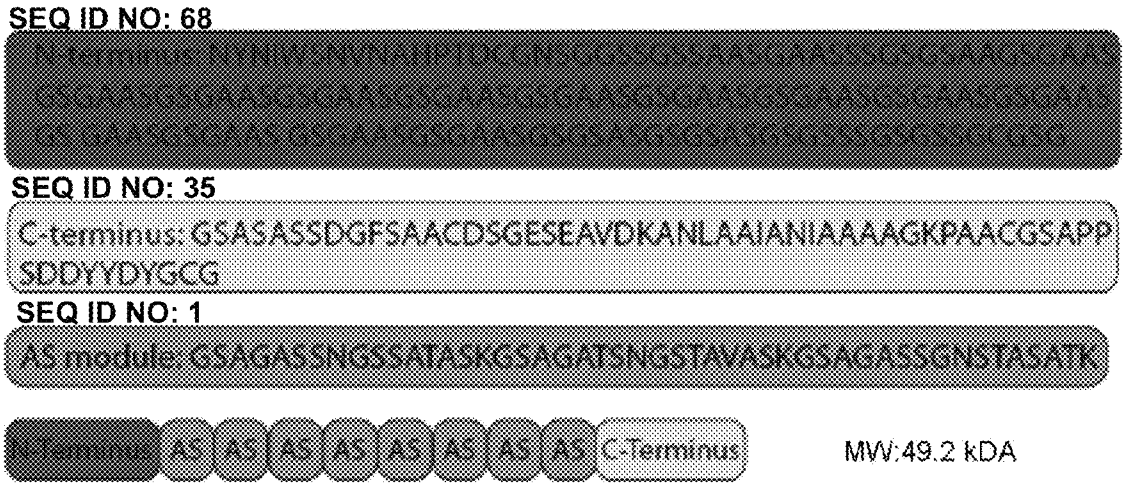
FIG. 1: Modular composition of N[AS]$_8$C; Designed modules and N[AS]$_8$C composition. N=N-terminus: SEQ ID NO: 68, C=C-terminus: SEQ ID NO: 35, and AS=AS module: SEQ ID NO: 1 repeated 8 times.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

As mentioned above, there is still a need to provide biopolymers yielding structures with advantageous properties such as e.g. excellent tensile strength, extensibility and toughness.

Accordingly, the present invention relates to a biopolymer comprising or consisting of at least two repeats of an amino acid sequence comprising or consisting of:

(a) the amino acid sequence of formula I:

(SEQ ID NO: 67)

Gly-Ser-$X_1$-$X_2$-Ala-$X_3$-Ser-$X_4$-$X_5$-Ser-$X_6$-Ala-$X_7$-Ala- $X_8$-Lys-$X_9$-$X_{10}$-Ala-$X_{11}$-Ala-$X_{12}$-Ser-$X_{13}$-$X_{14}$-Ser-Thr-

-continued

Ala-$X_{15}$-Ala-Ser-Lys-Gly-Ser-Ala-$X_{16}$-Ala-$X_{17}$-Ser- $X_{18}$-$X_{19}$-Ser-Thr-Ala-$X_{20}$-Ala-$X_{21}$-Lys (formula I), wherein:

$X_1$ is selected from the group consisting of Ala and Ser;

$X_2$ and $X_3$ are each independently selected from the group consisting of Gly, Ser, Thr and Val;

$X_4$ is selected from the group consisting of Asn, Gly, Gln and Asp;

$X_5$, $X_{13}$, $X_{14}$, $X_{18}$ and $X_{19}$ are each independently selected from the group consisting of Gly and Asn;

$X_6$, $X_{11}$, $X_{12}$, $X_{15}$, $X_{16}$, and $X_{20}$ are each independently selected from the group consisting of Gly, Ser, Thr, Ala and Val;

$X_7$ is selected from the group consisting of Ser, Thr and Ala;

$X_8$ and $X_{21}$ are each independently selected from the group consisting of Ser and Thr;

$X_9$ is selected from the group consisting of Gly and Asp;

$X_{10}$ is selected from the group consisting of Ser, Ala and Gly; and $X_{17}$ is selected from the group consisting of Ser, Thr, Ala and Val;

and wherein at least one of $X_4$ and $X_5$ is Gly;

at least one of $X_{13}$ and $X_{14}$ is Gly; and at least one of $X_{18}$ and $X_{19}$ is Gly; and/or (b) a variant of the amino acid sequence of (a), wherein the variant differs from the amino acid sequence of (a) in 1 to 10 amino acids, e.g. 1, 2, 3, 4, 5, 6, 7, 8, 9, or 10 amino acids, and wherein the variations are selected from the group consisting of substitutions, deletions, insertions and/or additions.

Preferably, the variations do not or do not substantially reduce the biophysical properties of the biopolymer formed as compared to a biopolymer comprising or consisting of repeats of the amino acid sequence of (a), wherein the biophysical properties are at least one of the ability of the biopolymer to stay in solution, the processability of the biopolymer and the tensile strength, extensibility, Young's modulus/stiffness and/or toughness of fibres produced from the biopolymer of the invention.

The biopolymer of the invention may be a recombinant biopolymer.

The term biopolymer is well known in the art and refers to a molecule composed of repeating structural units. In accordance with the present invention, the biopolymer is composed of repeating units based on the structure of formula (I) and variants thereof.

In those embodiments where a biopolymer comprises (rather than consists of) the recited sequence of (a) and/or (b), additional amino acids extend over the specific sequence either at the N-terminal end or the C-terminal end or both. Preferably, no more than 500 additional amino acids are present at the N-terminal end and no more than 500 additional amino acids are present at the C-terminal end. More preferably no more than 400, such as no more than 300, more preferably no more than 200, such as no more than 100, no more than 90, no more than 80, no more than 70, no more than 60, no more than 50, no more than 40, no more than 30, no more than 20 and even more preferably no more than 10 additional amino acids are independently present at either one or both of the N- or C-terminal end. Most preferably, no more than 5, e.g. 1, 2, 3, 4, or 5, additional amino acids are independently present at either one or both of the N- or C-terminal end. Additional sequences may include further repetitive sequences or non-repetitive sequences that form part of the resulting biopolymer as well as sequences introduced for example for purification. Such biopolymers comprising additional sequences represent a preferred embodiment of the invention, as detailed below.

In accordance with the present invention, the biopolymer comprises or consists of at least two repeats, i.e. two or more repeats. For example, the term "at least two repeats" also relates to at least three repeats, such as at least four repeats, such as at least five, at least six, at least seven, at least eight, at least nine, at least ten repeats or more, such as at least eleven, at least 12, at least 13, at least 14, at least 15, at least 16, at least 17, at least 18, at least 19 or at least 20 repeats. Also encompassed by this term are at least 25 repeats, such as for example at least 30 repeats, such as for example at least 40 repeats, such as for example at least 50 repeats, such as for example at least 80 repeats, or such as for example at least 100 repeats. The term further encompasses exactly two, exactly three, exactly four, exactly five, exactly six, exactly seven, exactly eight, exactly nine, exactly ten, exactly eleven, exactly 12, exactly 13, exactly 14, exactly 15, exactly 16, exactly 17, exactly 18, exactly 19, at least exactly 20, such as exactly 25, exactly 30, exactly 40, exactly 50, exactly 80, or exactly 100 repeats.

In other embodiments of the present invention, the biopolymer comprises or consists of between 2 and 100 repeats, e.g. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 repeats. Preferably, the biopolymer comprises or consists of between 5 and 100 repeats or between 8 and 100 repeats. More preferably, the biopolymer comprises or consists of between 5 and 80 repeats or between 8 and 80 repeats. Even more preferably, the biopolymer comprises or consists of between 5 and 50 repeats or between 8 and 50 repeats. Most preferably, the biopolymer comprises or consists of between 5 and 20 repeats or between 8 and 20 repeats, e.g. 8 repeats.

It will be readily understood by a person skilled in the art that the at least two repeats within one biopolymer may be identical or different, as long as they comprise or consist of the amino acid sequence of formula (I) or a variant thereof as defined in (b). In other words, a biopolymer in accordance with the present invention may for example consist of two repeats, wherein in the first $X_1$ is Ala and in the second $X_1$ is Ser, while all other residues are identical; or $X_1$ is different from Ala or Ser, while all other residues are identical and the biophysical properties of the resulting biopolymer as compared to a biopolymer comprising or consisting Ala or Ser in $X_1$ are not or not substantially reduced. In another example, a biopolymer in accordance with the present invention may comprise two repeats having the identical residues in formula (I), while one repeat further comprises an additional amino acid at one end but the other repeat does not comprise any additional amino acids.

The amino acids referred to herein are abbreviated in accordance with the established nomenclature employed in the art which is well known to the skilled person and is shown in the following table:

| Amino Acid | three-letter code | one-letter code |
|---|---|---|
| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp or Try | W |
| Tyrosine | Tyr | Y |
| Valine | Val | V |

In accordance with the present invention, the amino acid sequence representing one of the repeats of the biopolymer may comprise or consist of the amino acid sequence of formula I, as defined in (a).

In those embodiments where the amino acid sequence representing one of the repeats comprises (rather than consists of) the sequence of formula I or the variant sequence defined in (b), additional amino acids extend over the specific sequence either at the N-terminal end or the C-terminal end or both. Preferably, no more than 30 additional amino acids are present at the N-terminal end and no more than 30 additional amino acids are present at the C-terminal end. More preferably no more than 25, such as no more than 20, more preferably no more than 15 and even more preferably no more than 10, no more than 9, no more than 8, no more than 7, no more than 6, no more than 5, no more than 4, no more than 3, no more than 2 and even more preferably no more than 1 additional amino acid is independently present at either one or both of the N- or C-terminal ends. Additional sequences may include linkers for connecting the repetitive sequences as well as sequences introduced for example for purification.

Also in accordance with the present invention, the amino acid sequence representing the repeats of the biopolymer may be a variant of the amino acid sequence of (a), wherein the variant differs from the amino acid sequence of (a) in 1 to 10 amino acids, e.g. 1, 2, 3, 4, 5, 6, 7, 8, 9, or 10 amino acids.

In accordance with the present invention, these variations in amino acid sequences are selected from the group consisting of substitutions, deletions, insertions and/or additions. The amino acid sequence deviating from the amino acid sequence described in (a) by 1 to 10 amino acids, e.g. 1, 2, 3, 4, 5, 6, 7, 8, 9, or 10 amino acids, in accordance with the present invention is also referred to herein as the "variant repeat sequence".

The term "substitution", as used herein, refers to the replacement of amino acids with other amino acids. Preferably, amino acid "substitutions" are the result of replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. This variation is preferred in accordance with the present invention.

The term "deletion" as used in accordance with the present invention refers to the loss of amino acids, e.g. one or more amino acids, while the term "insertion" in accordance with the present invention refers to the incorporation of amino acids, e.g. one or more amino acids, into the amino acid sequence of the repeat of (a), wherein these amino acids are not added to the end of the sequence. Where amino acids are added to the N- or C-terminal end of the amino acid sequence of (a), the variation is referred to as "addition". Variations in form of "additions" refer to direct additions of amino acids to ends of the amino acid sequence of formula I, i.e. either in front of the initial Gly or behind the last Lys. Accordingly, where the amino acid sequence of the repeats comprises rather than exists of the amino acid sequence defined in (b), further amino acids that extent over the specific sequence of formula I—as defined herein above—may be added to the amino acid sequence of the repeats. It will be appreciated that these further amino acids are not variations falling under the terms of option (b).

In accordance with the present invention, the substitutions, deletions, insertions and/or additions taken together are in the range of 1 to 10 amino acids, preferably in the range of 1 to 8 amino acids, more preferably in the range of 1 to 5 amino acids and most preferably are 1, 2 or 3 amino acids.

Residues of the amino acid sequence of formula I that are defined as $X_1$ to $X_{21}$ each represent one amino acid residue. Accordingly, substitution of for example one of these residues for a different amino acid is regarded a variation in one amino acid. Similarly, deletion of one of these residues is regarded as a variation in one amino acid. With regard to insertions and/or additions of amino acids, the number of inserted amino acids defines the variation. It will be appreciated that the total difference between the biopolymer defined in (a) and the variant defined in (b) is calculated based on the combined number of amino acid substitutions, deletions, insertions and additions carried out. For example, deletion of $X_1$ and insertion of 5 amino acids that are not alanine or serine into the corresponding position is regarded as a variation of six amino acids.

Also preferred in accordance with the present invention is that the resulting variant of the amino acid sequence of formula I has a length of 48 amino acids.

Only those variations are encompassed in this invention, which do not negatively affect the desired characteristics of the biopolymer of the invention. In other words, the variations are restricted to those variations that do not (substantially) reduce the biophysical properties of the biopolymer formed from these variant repeat sequences as compared to a biopolymer comprising or consisting of repeats of the amino acid sequence of (a).

The variations allowed may be experimentally determined by systematically making insertions, deletions, additions and/or substitutions of amino acids in the sequences of the present invention, such as e.g. the repeats of a biopolymer or the additional polypeptides defined herein below, using recombinant DNA techniques and assaying the resulting recombinant variants for their formation of a similar secondary structure and their behavior in terms of solubility and processability as well as their quaternary structure and tensile strength, extensibility and toughness, preferably in direct comparison to a biopolymer made of the corresponding sequences of the present invention, i.e. repeats as defined in (a) or the unmodified polypeptide sequences referred to herein below. The skilled person is aware of methods of testing and comparing these properties, such as for example described in the appended examples.

The term "variations that do not substantially reduce the biophysical properties" refers to variations that maintain the biophysical properties of the resulting biopolymer to at least 80%, such as for example at least 85%, such as at least 90%, such as at least 95%, more preferably at least 98% and most preferably maintain or improve the biophysical properties of the resulting biopolymer as compared to a corresponding biopolymer made of unmodified sequences in accordance with the invention, such as e.g. an identical number of repeats, wherein the repeats are as defined in (a). It will be appreciated that preferably the comparison is made to a biopolymer that only differs from the variant sequence in a variation as defined herein. In other words, where a variant repeat sequence as defined above in (b) is incorporated into a biopolymer, the comparison is made with a biopolymer having the same overall structure (including N- and/or C-terminal polypeptides) but differing in the repeat sequence by said variations from the repeat sequence of (a).

Even more preferably, the comparison is made with a biopolymer made up of repeats comprising or consisting of the amino acid sequence of SEQ ID NO: 1 and most preferably with a biopolymer comprising or consisting of repeats consisting of the amino acid sequence of SEQ ID NO: 1.

In accordance with the present invention, the biophysical properties are at least one of the ability of the biopolymer to stay in solution, the processability of the biopolymer and the tensile strength, extensibility, Young's modulus/stiffness and/or toughness of fibres produced from the biopolymer of the invention. More preferably, the biophysical properties are at least two of the recited properties, more preferably at least three, such as at least four, more preferably at least five and most preferably all six of the recited properties.

The term "tensile strength", as used herein, is defined in accordance with the pertinent art and relates to the maximum stress that a material can withstand while being stretched or pulled. Tensile strength is defined as a stress, which is measured as force per unit area. In the SI system, the unit is the pascal (Pa) (or a multiple thereof, often megapascals (MPa), using the mega-prefix); or, equivalently to pascals, newtons per square meter ($N/m^2$). Preferably, the variant biopolymer of the invention has a tensile strength of at least 40 MPa (at 30% relative humidity (RH)) and 15 MPa (at 70% RH).

The term "extensibility", as used herein, is defined in accordance with the pertinent art and relates to the maximal extension a material can withstand before rupture. The unit of the extensibility is %. Preferably, the variant biopolymer of the invention has a extensibility of at least 1.5% independent of RH.

The term "toughness", as used herein, is defined in accordance with the pertinent art and relates to the ability of a material to absorb energy and plastically deform without fracturing. Material toughness is defined as the amount of energy per volume that a material can absorb before rupturing. Toughness requires a balance of strength and ductility. The area covered under a stress strain curve is called toughness. Toughness is measured in units of joules per cubic meter ($J/m^3$) in the SI system. Preferably, the variant biopolymer of the invention has a toughness of at least 700 $J/m^3$ independent of RH.

The term "Young's modulus" as used herein, is defined in accordance with the pertinent art and relates to the stiffness of a material. The Young's modulus, also known as the tensile modulus, is a measure of the stiffness of an elastic material and is a quantity used to characterize materials. It is defined as the ratio of the uniaxial stress over the uniaxial strain in the range of stress in which Hooke's Law holds. The SI unit of modulus of elasticity (E) is the pascal (Pa or $N/m^2$). Preferably, the variant biopolymer of the invention has a Young's modulus of at least 1 $GN/m^2$ (at 30% RH) and 0.8 $GN/m^2$ (at 70% RH).

All of the biophysical properties referred to herein above can be tested employing any method known in the art, such as for example dissolving the biopolymers in various solvents comprising aqueous solvents such as GdmSCN (guanidinium thiocyanate), GdmCl (guanidinechloride), urea, Hepes- and tris buffers as well as non aqueous solvents such as HFA (Hexafluoroacetone), HFIP (Hexafluoroisopropanol), formic acid, trichlormethan and ionic liquids. For the ionic liquids, several cations can be used which can be alkylated such as imidazolium, pyridinium, pyrrolidinium, guanidinium, uronium, thiouronium, piperidinium, morpholinium, ammonium and phosphonium. As anion one could use halogenoids and complex ions such as tetrafluoroborate, trifluoracetate, triflate, hexafluorophosphate phosphinate and tosylate. Also organic ions, such as imide and amide are possible anions. The concentration at which the biopolymer is soluble may then be determined. For example, to determine the maximal concentration of soluble biopolymer, a 1 mg/ml (=0.1% (w/v)) solution in various solvents can be concentrated by ultra filtration using e.g. a 10,000 Da molecular weight cut off polyether sulfone membrane. At certain intervals, samples can be taken from the solution until the biopolymer starts to precipitate. Samples can then be diluted in solvent at a defined ratio to determine the protein concentration photometrically. Preferably, the variant biopolymer of the invention has a solubility of at least 0.1 mg/ml.

Moreover, tensile strength may for example be tested as shown in the appended examples, where an extension rate of 0.01 mm/s and a relative humidity of 30% and 70% at 22° C. were employed. Also extensibility and toughness may be tested using the methods as described in the examples. Additional methods include, without being limiting asymmetric flow field-flow fractionation; fast protein liquid chromatography (FPLC); high-performance liquid chromatography (HPLC); CD-spectroscopy, fluorescence spectroscopy; UV-VIS-spectroscopy; FT-IR spectroscopy; Raman-spectroscopy; differential scanning calorimetry (DSC); dynamic mechanical thermal analysis (DMTA); rheology; thermogravimetric analysis (TGA); static and dynamic tensile tests. All of these methods are well known in the art and the skilled person knows how to employ these methods (Materials science and technology: A comprehensive Treatment; Characterization of Materials, Vol. 2a, Cahn, Haasen and Kramer; Wiley-VCH ISBN-13:978-3-527-31395-2).

In accordance with the present invention, artificial biopolymers comprising repeats that form cross-(3-structures are provided. Whereas the motifs of repetitive sequences in biopolymers typically have a length of at most 30 amino acids (Structure and mechanism in Protein science; Alan Fersht; 1999; W. H. Freeman and Company), the motif of the repeats of the biopolymer of the present invention is based on a length of 48 amino acids (i.e. formula I) as well as variations thereof of a maximum of 10 amino acids less or more. Surprisingly, it was found in accordance with the present invention that biopolymers based on such unusual 48-amino acid motifs possess excellent tensile strength, extensibility and toughness. The biopolymers of the present invention can be processed into materials which can be used for numerous technical as well as biomedical applications. For example, the biopolymers of the present invention may be used for the preparation of foams, films, gels, coatings, particles, capsules, springs or nonwovens mats. The biopolymers may further be used for the preparation of fibres, as described herein below. Moreover, the biopolymers of the present invention show excellent stability in solution and easily assemble into the above listed structures enabling their use in numerous applications, as described herein below. Further advantageous properties are hydrating and softening effects when the biopolymers of the invention are employed in e.g. cosmetic preparations. The biopolymers of the invention can be produced recombinantly, which ensures a superior homogeneity and monodispersity which cannot be achieved by purifying any of the naturally occurring biopolymers.

In a preferred embodiment of the biopolymer of the invention, the amino acid sequence of formula I is selected from the group consisting of:

(i) the amino acid sequence of SEQ ID NO: 1;

(ii) an amino acid sequence having at least 80% sequence identity, preferably at least 85% sequence identity, more preferably at least 90% sequence identity, even more preferably at least 96% sequence identity and most preferably at least 99% sequence identity, e.g. at least 91% sequence identity, to the amino acid sequence of SEQ ID NO: 1;

(iii) an amino acid sequence encoded by a nucleic acid molecule of SEQ ID NO: 2;

(iv) an amino acid sequence encoded by a nucleic acid sequence that hybridizes under stringent conditions to the complementary strand of the nucleic acid sequence of SEQ ID NO: 2;

(v) an amino acid sequence encoded by a nucleic acid sequence that is degenerate with respect to the nucleic acid sequence of (iii) or (iv); and (vi) a variant of the amino acid sequence of (i), wherein the variant differs from the amino acid sequence of (i) in 1 to 10 amino acids, e.g. 1, 2, 3, 4, 5, 6, 7, 8, 9, or 10 amino acids, wherein the variations are selected from the group consisting of substitutions, deletions, insertions and/or additions.

Preferably, the variations do not or do not substantially reduce the biophysical properties of the biopolymer formed with this repeat sequence as compared to a biopolymer formed with a repeat sequence comprising or consisting of the amino acid sequence of (i), wherein the biophysical properties are at least one of the ability of the biopolymer to stay in solution, the processability of the biopolymer and the tensile strength, extensibility, Young's modulus/stiffness and/or toughness of fibres produced from the biopolymer of the invention.

The amino acid sequence of SEQ ID NO: 1 is: Gly-Ser-Ala-Gly-Ala-Ser-Ser-Asn-Gly-Ser-Ser-Ala-Thr-Ala-Ser-Lys-Gly-Ser-Ala-Gly-Ala-Thr-Ser-Asn-Gly-Ser-Thr-Ala-Val-Ala-Ser-Lys-Gly-Ser-Ala-Gly-Ala-Ser-Ser-Gly-Asn-Ser-Thr-Ala-Ser-Ala-Thr-Lys.

As is shown in the appended examples, biopolymers comprising eight repeats of the amino acid sequence of SEQ ID NO: 1 can be recombinantly produced in *E. coli* and upon processing into fibres show good tensile strength, extensibility and toughness. Accordingly, it is preferred that the biopolymer of the invention comprises or consists of eight repeats of SEQ ID NO: 1. It is more preferred that said biopolymer is a recombinant biopolymer.

In accordance with the present invention, the term "% sequence identity" describes the number of matches ("hits") of identical amino acids/nucleotides of two or more aligned amino acid or nucleic acid sequences as compared to the number of amino acid residues or nucleotides making up the overall length of the amino acid sequences or nucleic acid (or the overall compared part thereof). In other terms, using an alignment, for two or more sequences or sub-sequences the percentage of amino acid residues or nucleotides that are the same (e.g., 80% or 85% identity) may be determined, when the (sub)sequences are compared and aligned for maximum correspondence over a window of comparison, or over a designated region as measured using a sequence comparison algorithm as known in the art, or when manually aligned and visually inspected. Preferred polypeptides/nucleic acid molecules in accordance with the invention are those where the described identity exists over a region that is at least about 15 to 25 amino acids or nucleotides in length, more preferably, over a region that is at least about 50 to 100 amino acids or nucleotides in length. More preferred polypeptides/nucleic acid molecules in accordance with the present invention are those having the described sequence identity over the entire length of the polypeptide or nucleic acid molecule specifically recited herein. Those having skill in the art will know how to determine percent sequence identity between/among sequences using, for example, algorithms such as those based on the NCBI BLAST algorithm (Stephen F. Altschul, Thomas L. Madden, Alejandro A. Schäffer, Jinghui Zhang, Zheng Zhang, Webb Miller, and David J. Lipman (1997), "Gapped BLAST and PSI-BLAST: a new generation of protein database search programs", Nucleic Acids Res. 25:3389-3402), CLUSTALW computer program (Thompson Nucl. Acids Res. 2 (1994), 4673-4680) or FASTA (Pearson and Lipman, Proc. Natl. Acad. Sci., 1988, 85; 2444).

The NCBI BLAST algorithm is preferably employed in accordance with this invention. For amino acid sequences, the BLASTP program uses as default a word length (W) of 3, and an expectation (E) of 10. The BLASTN program for nucleic acid sequences uses as default a word length (W) of 11, an expectation (E) of 10, M=5, N=4, and a comparison of both strands. The BLOSUM62 scoring matrix (Henikoff, Proc. Natl. Acad. Sci., 1989, 89:10915) uses alignments (B) of 50, expectation (E) of 10, M=5, N=4, and a comparison of both strands. Accordingly, all the polypeptides having the prescribed function and further having a sequence identity of at least 80% as determined with the NCBI BLAST program fall under the scope of the invention.

In accordance with this embodiment of the present invention, also encompassed are sequences having at least 80% sequence identity, preferably at least 85% sequence identity, and more preferably at least 90% sequence identity, e.g. at least 80% sequence identity, at least 81% sequence identity, at least 82% sequence identity, at least 83% sequence identity, at least 84% sequence identity, at least 85% sequence identity, at least 86% sequence identity, at least 87% sequence identity, at least 88% sequence identity, at least 89% sequence identity, at least 90% sequence identity, or at least 91% sequence identity, such as at least 92%, at least 93%, at least 94% and at least 95% sequence identity. Even more preferably, the identity is at least 96%, such as at least 97%, at least 98% and most preferably at least 99%.

The term "nucleic acid molecule", as used herein, is well known in the art and includes for example DNA, such as cDNA or genomic DNA, and RNA, such as mRNA.

The term "hybridizes/hybridizing" as used herein refers to a pairing of a nucleic acid molecule to a (partially) complementary strand of this nucleic acid molecule which thereby form a hybrid/double-stranded molecule.

It is well known in the art how to perform hybridization experiments with nucleic acid molecules. Correspondingly, the person skilled in the art knows what hybridization conditions she/he has to use to allow for a successful hybridization in accordance with item (i)(c), above. The establishment of suitable hybridization conditions is referred to in standard text books such as Sambrook, Russell "Molecular Cloning, A Laboratory Manual", Cold Spring Harbor Laboratory, N.Y. (2001); Ausubel, "Current Protocols in Molecular Biology", Green Publishing Associates and Wiley Interscience, N.Y. (1989), or Higgins and Hames (Eds.) "Nucleic acid hybridization, a practical approach" IRL Press Oxford, Washington D.C., (1985).

"Stringent conditions" refers to hybridization conditions under which the nucleic acid molecules that are capable of hybridizing to the nucleic acid molecules of the invention or parts thereof hybridize to these target sequences to a detectably greater degree than to other sequences (e.g., at least 2-fold over background). Stringent conditions are sequence-dependent and will be different in different circumstances. By controlling the stringency of the hybridization and/or washing conditions, target sequences that have at least 90% sequence identity, more preferably 95%, such as 98% and more preferred 100% sequence identity to the probe can be identified (highly stringent hybridization conditions). Alternatively, stringency conditions can be adjusted to allow a higher degree of mismatching in sequences (low stringency conditions of hybridization). Such highly stringent and low stringent conditions for hybridization are well known to the person skilled in the art. For example, highly stringent conditions for hybridization comprise, e.g. an overnight incubation at 65° C. in 4×SSC (600 mM NaCl, 60 mM sodium citrate) followed by washing at 65° C. in 0.1×SSC for one hour. Alternatively, highly stringent hybridization conditions can comprise: an overnight incubation at 42° C. in a solution comprising 50% formamide, 5×SSC (750 mM NaCl, 75 mM sodium citrate), 50 mM sodium phosphate (pH 7.6), 5×Denhardt's solution, 10% dextran sulphate, and 20 μg/ml denatured, sheared salmon sperm DNA, followed by washing in e.g. 0.1-0.5×SSC at about 55-65° C. for about 5 to 20 min. As mentioned, also contemplated are nucleic acid molecules that hybridize to the nucleic acid molecules of the invention at lower stringency hybridization conditions ("low stringency conditions for hybridization"). Changes in the stringency of hybridization are primarily accomplished through the manipulation of formamide concentration (lower percentages of formamide result in lowered stringency), salt conditions, or temperature. For example, lower stringency conditions include an overnight incubation at 50° C. in 4×SSC or an overnight incubation at 37° C. in a solution comprising 6×SSPE (20×SSPE=3M NaCl; 0.2M NaH2PO4; 0.02M EDTA, pH 7.4), 0.5% SDS, 30% formamide, 100 mg/ml salmon sperm blocking DNA; followed by washes at 50° C. with 1×SSPE, 0.1% SDS. To achieve an even lower stringency, washes performed following stringent hybridization can be done at higher salt concentrations (e.g. 5×SSC). Based on the above discussed variables composition and length of the nucleic acid molecules, temperature, salt concentrations etc., the skilled person knows how to determine suitably stringent hybridization conditions capable of specifically detecting even single base pair mismatches. It is of note that variations in the above conditions may be accomplished through the inclusion and/or substitution of alternate blocking reagents. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility. Such modifications can generally be effected by the skilled person without further ado. The embodiment recited herein above preferably refers to highly stringent conditions and alternatively to conditions of lower stringency. A hybridization complex may be formed in solution (e.g., Cot or Rot analysis) or between one nucleic acid sequence present in solution and another nucleic acid sequence immobilized on a solid support (e.g., membranes, filters, chips, pins or glass slides to which, e.g., cells have been fixed).

In accordance with the present invention, any sequence defined as a sequence having a certain degree of sequence identity or as a hybridising sequence has to fulfil the same requirements as defined herein above with regard to the variations. In other words, only encompassed herein are hybridising sequences or sequences of a certain degree of sequence identity if they do not or do not substantially reduce the biophysical properties of the resulting biopolymer made up with these sequences as compared to a biopolymer made up with the specifically recited sequences of SEQ ID NO: 1 to 68, e.g. SEQ ID NO: 66, wherein the biophysical properties are at least one of the ability of the biopolymer to stay in solution, the processability of the biopolymer and the tensile strength, extensibility, Young's modulus/stiffness and/or toughness of fibres produced from the biopolymer of the invention.

The term "degenerate" in accordance with the present invention refers to the redundancy of the genetic code. Degeneracy results because there are more codons than encodable amino acids. For example, if there were two bases per codon, then only 16 amino acids could be coded for ($4^2=16$). Because at least 21 codes are required (20 amino acids plus stop), and the next largest number of bases is three, then $4^3$ gives 64 possible codons, meaning that some degeneracy must exist. As a result, some amino acids are encoded by more than one triplet, i.e. by up to six triplets. The degeneracy mostly arises from alterations in the third position in a triplet. This means that nucleic acid molecules having a different sequence than that specified above, but still encoding the same polypeptide lie within the scope of the present invention.

All other definitions are defined as above with regard to the first embodiment.

In another preferred embodiment, the biopolymer further comprises an N- and/or C-terminal polypeptide.

In accordance with this embodiment, the biopolymer comprising several repeats as defined herein above may comprise additional amino acid sequences at the N- and/or C-terminal end. Preferred amounts of additional amino acids at the N- and/or C-terminus have been defined herein above.

Preferably, the biopolymer consists of eight repeats, most preferably repeats as defined in SEQ ID NO:1, and one polypeptide at one or at each of the N- and C-terminal ends.

The addition of N- and/or C-terminal polypeptides may improve the characteristics of the resulting Biopolymer. For example, the addition of N- and/or C-terminal polypeptides, such as for example any one of the polypeptides defined herein below, may further improve the solubility and processability of the biopolymers of the invention.

In a more preferred embodiment of the biopolymer of the invention, the N-terminal polypeptide is selected from the group consisting of:

(i) an amino acid sequence comprising or consisting of the amino acid sequence of any one of SEQ ID NO: 3 to SEQ ID NO: 18 or SEQ ID NO: 68;

(ii) an amino acid sequence having at least 80% sequence identity, preferably at least 85% sequence identity, more preferably at least 90% sequence identity, even more preferably at least 96% sequence identity and most preferably at least 99% sequence identity, to the amino acid sequence of (i);

(iii) an amino acid sequence encoded by a nucleic acid molecule comprising or consisting of the sequence of any one of SEQ ID NO: 19 to SEQ ID NO: 34;

(iv) an amino acid sequence encoded by a nucleic acid sequence that hybridizes under stringent conditions to the complementary strand of a nucleic acid sequence of (iii);

(v) an amino acid sequence encoded by a nucleic acid sequence that is degenerated with respect to the nucleic acid sequence of (iii) or (iv); and (vi) a variant of the amino acid sequence of (i), wherein the variant differs from the amino acid sequence of (i) in 1 to 10 amino acids, e.g. 1, 2, 3, 4, 5, 6, 7, 8, 9, or 10 amino acids, and wherein the variation(s) is (are) selected from the group consisting of substitutions, deletions, insertions and/or additions.

Preferably, the variations do not or do not substantially reduce the biophysical properties of the biopolymer formed with this variant N-terminal polypeptide as compared to a biopolymer formed with an N-terminal polypeptide comprising or consisting of the amino acid sequence of (i), wherein the biophysical properties are at least one of the ability of the biopolymer to stay in solution, the processability of the biopolymer and the tensile strength, extensibility, Young's modulus/stiffness and/or toughness of fibres produced from the biopolymer of the invention.

In another more preferred embodiment of the biopolymer of the invention, the C-terminal polypeptide is selected from the group consisting of:

(i) an amino acid sequence comprising or consisting of the amino acid sequence of any one of SEQ ID NO: 35 to SEQ ID NO: 50;

(ii) an amino acid sequence having at least 80% sequence identity, preferably at least 85% sequence identity, more preferably at least 90% sequence identity, even more preferably at least 96% sequence identity and most preferably at least 99% sequence identity, to the amino acid sequence of (i)

(iii) an amino acid sequence encoded by a nucleic acid molecule comprising or consisting of the sequence of any one of SEQ ID NO: 51 to SEQ ID NO: 66;

(iv) an amino acid sequence encoded by a nucleic acid sequence that hybridizes under stringent conditions to the complementary strand of a nucleic acid sequence of (iii);

(v) an amino acid sequence encoded by a nucleic acid sequence that is degenerate with respect to the nucleic acid sequence of (iii) or (iv); and (vi) a variant of the amino acid sequence of (i), wherein the variant differs from the amino acid sequence of (i) in 1 to 10 amino acids, e.g. 1, 2, 3, 4, 5, 6, 7, 8, 9, or 10 amino acids, and wherein the variation(s) is (are) selected from the group consisting of substitutions, deletions, insertions and/or additions.

Preferably, the variations do not or do not substantially reduce the biophysical properties of the biopolymer formed with this variant C-terminal polypeptide as compared to a corresponding biopolymer formed with a C-terminal polypeptide comprising or consisting of the amino acid sequence of (i), wherein the biophysical properties are at least one of the ability of the biopolymer to stay in solution, the processability of the biopolymer and the tensile strength, extensibility, Young's modulus/stiffness and/or toughness of fibres produced from the biopolymer of the invention.

In accordance with these embodiments of the present invention, also encompassed are sequences having at least 80% sequence identity to the specifically recited amino acid sequences, such as at least 81%, at least 82%, at least 83%, at least 84%. Preferably, the identity is at least 85%, such as at least 86%, at least 87%, at least 88%, at least 89%, more preferred at least 90%, such as at least 91%, at least 92%, at least 93%, at least 94% and 95%. Even more preferably, the identity is at least 96%, such as at least 97%, at least 98% and most preferably at least 99%. To evaluate the identity level between two nucleotide or protein sequences, they can be aligned electronically using suitable computer programs as described herein above.

With regard to a comparison of the biophysical properties of a variant biopolymer it will be appreciated that a biopolymer made up for example of a variant repeat sequence, a variant N-terminal polypeptide and a variant C-terminal polypeptide, i.e. where all three components are variant sequences needs to be compared to a biopolymer made up of a repeat sequence of formula I (i.e. a non-variant repeat sequence), a non-variant N-terminal polypeptide (i.e. an N-terminal polypeptide as defined in (i) above) and a non-variant C-terminal polypeptide (i.e. a C-terminal polypeptide as defined in (i) above). As a further example, a variant biopolymer made up for example of a variant repeat sequence and a variant N-terminal polypeptide but a non-variant C-terminal polypeptide needs to be compared to a biopolymer made up of a repeat sequence of formula I (i.e. a non-variant repeat sequence), a non-variant N-terminal polypeptide (i.e. an N-terminal polypeptide as defined in (i) above) and a non-variant C-terminal polypeptide (i.e. a C-terminal polypeptide as defined in (i) above). The same considerations apply to all other possible combinations of variant and non-variant sequences that make up the respective biopolymer.

All other definitions are as provided herein above with regard to the first and second embodiment.

The present invention also relates to a nucleic acid molecule encoding the biopolymer of the invention.

As defined herein above, the nucleic acid molecule of the invention may be for example DNA, such as cDNA or genomic DNA, and RNA, such as mRNA. Most preferably, the nucleic acid molecule is DNA.

The present invention further relates to a vector comprising the nucleic acid molecule of the invention. The nucleic acid molecule of the present invention may be inserted into several commercially available vectors. Preferably, the vector is a plasmid, cosmid, virus, bacteriophage or another vector used conventionally e.g. in genetic engineering. Non-limiting examples include prokaryotic plasmid vectors, such as the pET-series of expression vectors (Novagen), the pUC-series, pBluescript (Stratagene) or pCRTOPO (Invitrogen), lambda gt11, pJOE, the pBBR1-MCS series, pJB861, pBSMuL, pBC2, pUCPKS, pTACT1 and vectors compatible with expression in mammalian cells like E-027 pCAG Kosak-Chemy (L45a) vector system, pREP (Invitrogen), pCEP4 (Invitrogen), pMC1neo (Stratagene), pXT1 (Stratagene), pSG5 (Stratagene), EBO-pSV2neo, pBPV-1, pdBPVMMT-neo, pRSVgpt, pRSVneo, pSV2-dhfr, pIZD35, Okayama-Berg cDNA expression vector pcDV1 (Pharmacia), pRc/CMV, pcDNA1, pcDNA3 (Invitrogen), pSPORT1 (GIBCO BRL), pGEMHE (Promega), pLXIN, pSIR (Clontech), pIRES-EGFP (Clontech), pEAK-10 (Edge Biosystems) pTriEx-Hygro (Novagen) and pCINeo (Promega). Examples for plasmid vectors suitable for *Pichia pastoris* comprise e.g. the plasmids pAO815, pPIC9K and pPIC3.5K (all Invitrogen).

The nucleic acid molecule of the present invention referred to above may also be inserted into vectors such that a translational fusion with another nucleic acid molecule is generated. The other nucleic acid molecules may e.g. encode a amino acid sequence that increases the solubility and/or facilitates the purification of the biopolymer encoded by the nucleic acid molecule of the invention. Non-limiting examples of such vectors include pET28, pET29 pET32, pET41, pET43. Suitable bacterial expression hosts comprise e.g. strains derived from BL21 (such as BL21(DE3), BL21 (DE3)PlysS, BL21(DE3)RIL, BL21(DE3)PRARE), BL21 (DE3)gold, BLR or Rosetta.

The coding sequences inserted into the vector can be synthesized by standard methods. Ligation of the coding sequences to transcriptional regulatory elements and/or to other amino acid encoding sequences can be carried out using established methods. For vector modification techniques, see Sambrook and Russel, 2001. Regulatory sequences are well known to those skilled in the art and include, without being limiting, regulatory sequences ensuring the initiation of transcription, internal ribosomal entry sites (IRES) (Owens, Proc. Natl. Acad. Sci. USA 98 (2001), 1471-1476) and optionally regulatory elements ensuring termination of transcription and stabilization of the transcript. Non-limiting examples for regulatory elements ensuring the initiation of transcription comprise a translation initiation codon, enhancers such as e.g. the SV40-enhancer, insulators and/or promoters, such as for example the cytomegalovirus (CMV) promoter, SV40-promoter, RSV (Rous sarcome virus)-promoter, the lacZ promoter, chicken beta-actin promoter, CAG-promoter (a combination of chicken beta-actin promoter and cytomegalovirus immediate-early enhancer), the gai10 promoter, human elongation factor 1α-promoter, AOX1 promoter, GAL1 promoter CaM-kinase promoter, the lac, trp or tac promoter, the lacUV5 promoter, the *Autographa californica* multiple nuclear polyhedrosis virus (AcMNPV) polyhedral promoter or a globin intron in mammalian and other animal cells. The lac promoter is a typical inducible promoter, useful for prokaryotic cells, which can be induced using the lactose analogue isopropylthiol-β-D-galactoside ("IPTG"). Non-limiting examples for regulatory elements ensuring transcription termination include the V40-poly-A site, the tk-poly-A site or the SV40, lacZ or AcMNPV polyhedral polyadenylation signals, which are to be included downstream of the nucleic acid sequence of the invention. Additional regulatory elements may include translational enhancers, Kozak sequences and intervening sequences flanked by donor and acceptor sites for RNA splicing, nucleotide sequences encoding secretion signals or, depending on the expression system used, signal sequences capable of directing the expressed polypeptide to a cellular compartment. Moreover, elements such as origin of replication, drug resistance gene, regulators (as part of an inducible promoter) may also be included.

An expression vector according to this invention is capable of directing the replication, and the expression of the nucleic acid molecule of the invention and the biopolymer encoded thereby.

The present invention further relates to a non-human host transformed with the vector of the invention.

In a preferred embodiment, the host is a cell, such as an isolated cell which may be part of a cell culture.

Suitable prokaryotic host cells comprise e.g. bacteria of the species *Escherichia, Bacillus, Streptomyces* and *Salmonella typhimurium*. Suitable eukaryotic host cells are e.g. fungal cells, inter alia, yeasts such as *Saccharomyces cerevisiae* or *Pichia pastoris* or *Hansenula polymorpha* or insect cells such as *Drosophila* S2 cells, *Spodoptera* Sf9 cells, Sf21 cells and High five cells as well as plant cells and mammalian cells. Mammalian host cells include without being limiting, mouse NIH3T3 and C127 cells, COS 1, COS 7 and CV1, quail QC1-3 cells, mouse L cells, Chinese hamster ovary (CHO) cells and Bowes melanoma cells. It will readily be understood by the skilled person that the choice of host cell may be adjusted to achieve the desired posttranscriptional modification of the biopolymer of the invention, such as for example the presence or absence of glycosylation. For example, eukaryotic host cells mutated with respect to its ability to glycosylate may be employed, see e.g. Deutscher et al. 1984 (Cell, 39: 295-299).

Appropriate culture media and conditions for the above-described host cells are known in the art and include, without being limiting, the conditions and media detailed further below.

The present invention further relates to a method for the production of a biopolymer of the invention, comprising culturing the non-human host cell of the invention under suitable conditions and isolating the biopolymer produced.

Suitable conditions for culturing a prokaryotic or eukaryotic host are well known to the person skilled in the art. For example, suitable conditions for culturing bacteria are growing them under aeration in Luria Bertani (LB) medium. To increase the yield and the solubility of the expression product, the medium can be buffered or supplemented with suitable additives known to enhance or facilitate both. *E. coli* can be cultured from 4 to about 37° C., the exact temperature or sequence of temperatures depends on the molecule to be (over-)expressed. In general, the skilled person is also aware that these conditions may have to be adapted to the needs of the host and the requirements of the polypeptide expressed. In case an inducible promoter controls the nucleic acid molecule of the invention in the vector present in the host cell, expression of the polypeptide can be induced by addition of an appropriate inducing agent, such as e.g. IPTG or lactose. Suitable expression protocols and strategies are known to the skilled person.

Depending on the cell type and its specific requirements, mammalian cell cultures can e.g. be carried out in RPMI or DMEM medium containing 10% (v/v) FCS, 2 mM L-glutamine and 100 U/ml penicillin/streptomycine. The cells can be kept at 37° C. in a 5% $CO_2$, water saturated atmosphere. Suitable media for insect cell culture are e.g. TNM+10% FCS or SF900 medium. Insect cells are usually grown at 27° C. as adhesion or suspension cultures.

Further suitable expression protocols for eukaryotic cells are well known to the skilled person and can be retrieved e.g. from Sambrook, 2001, loc cit.

Methods of isolating the biopolymer produced are well-known in the art and comprise, without being limiting, method steps such as ion exchange chromatography, gel filtration chromatography (size exclusion chromatography), affinity chromatography, high pressure liquid chromatography (HPLC), reversed phase HPLC, disc gel electrophoresis or immunoprecipitation, see, for example, in Sambrook, 2001, loc. cit. More preferably, purification is performed as described in the appended examples, i.e. cells are lysed, followed by acidification and a subsequent fractional ammonium sulphate precipitation (using e.g. 1.5 M and 2.5 M ammonium sulphate). The purified biopolymer may then be washed with water and lyophilized.

The present invention further relates to foams, films, gels, e.g. hydrogels, coatings, particles, capsules, springs or nonwovens, e.g. nonwoven mats, comprising or consisting of the biopolymer of the invention or the biopolymer obtained by the method of the invention. Accordingly, the present invention also relates to the use of the biopolymer of the invention or of the biopolymer obtained by the method of the invention for the preparation of foams, films, gels, coatings, particles, capsules, springs or nonwovens mats.

It is preferred that the foams, films, gels, e.g. hydrogels, coatings, particles, capsules, springs or nonwovens, e.g. nonwoven mats, comprising the biopolymer of the invention or the biopolymer obtained by the method of the invention comprise one or more cells, such as one or more isolated cells, which may be part of a tissue. Said one or more cells, such as one or more isolated cells, may be incorporated into and/or attached to or associated with said foams, films, gels, e.g. hydrogels, coatings, particles, capsules, springs or nonwovens, e.g. nonwoven mats.

Said cells may be prokaryotic cells, e.g. bacteria of the species *Escherichia, Bacillus, Streptomyces* and *Salmonella typhimurium*. Said cells may also be eukaryotic cells, e.g. fungal cells, inter alia, yeasts such as *Saccharomyces cerevisiae* or *Pichia pastoris* or *Hansenula polymorpha* or insect cells such as *Drosophila* S2 cells, *Spodoptera* Sf9 cells, Sf21 cells and High five cells as well as plant cells, e.g. tobacco, potato, corn, pea or tomato cells, and mammalian cells, e.g. mouse NIH3T3 and C127 cells, COS 1, COS 7 and CV1, quail QC1-3 cells, mouse L cells, Chinese hamster ovary (CHO) cells and Bowes melanoma cells.

Said foams, films, gels, e.g. hydrogels, coatings, particles, capsules, springs or nonwovens, e.g. nonwoven mats, seeded with one or more cells, such as one or more isolated cells, can be used, for example, for artificial nerve regeneration or muscle cell growth.

The term "foam", as used herein, is defined in accordance with the pertinent prior art and relates to a solid structure made by creating bubbles of gas in a solution and solidifying it. Foams may be made from the biopolymer of the present invention by e.g. frothing up a solution comprising 0.1 to 50% (w/v) of the biopolymer of the invention with air. The resulting foam structures may be stabilized via cross-linking by exposition to visible light, e.g. from a tungsten lamp for 1 minute (Protocol: PNAS 1999 Vol. 96 pp. 6020-6024) and subsequent drying of the foam at e.g. 95° C. Exemplary solutions for the preparation of foams from the biopolymer of the invention comprise 2.5 mM ammonium peroxodisulfate (APS), 100 μM tris(2,2'-bipyridyl)dichlororuthenium(II) (Rubpy) and 0.1 to 50% (w/v) of the biopolymer of the invention. More preferably, the solution comprises 1 to 20% (w/v) of the biopolymer of the invention and even more preferably 2 to 10% (w/v) of the biopolymer of the invention. Another exemplary technique to produce foams is salt leaching where salt crystals such as NaCl are put into a mold and the biopolymer is poured over the salt, penetrating into all the small spaces left between the salt crystals. The polymer is subsequently hardened and then the salt is removed by dissolving it in a solvent (such as water or alcohol) which washes/leaches the salt out. Upon removal of the salt crystals all that remains is the hardened foam with open holes/pores where the salt was beforehand.

As used herein, the term "film" is defined in accordance with the pertinent prior art and relates to a sheet formed from the biopolymer of the invention, preferably a thin sheet of a thickness between 0.01 μm and 1000 μm. A film may be formed from a single layer as well as from multilayers. Films can be cast from solutions comprising 0.1 to 50% (w/v) of the biopolymer of the invention, preferably comprising 1 to 20% (w/v) of the biopolymer of the invention and even more preferably comprising 2 to 10% (w/v) of the biopolymer of the invention. Any solvent known in the art may be employed for preparing a solution, such as for example HFA, HFIP, formic acid or mixtures of these with water. As a substrate, various surfaces might be used, such as e.g. polystyrene, Teflon®, glass, polyurethane or quartz glass. Films can simply be cast onto such a surface and are then left to dry. After evaporation of the solvent, the biopolymers form films that can easily be peeled off the surface. The resulting films may be further modified to obtain functionalized films or to achieve water insolubility of the films by methods such as those described in the Examples and other methods well known in the art.

As used herein, the term "gel" is defined in accordance with the pertinent prior art and refers to a colloid in which the disperse phase has combined with the dispersion medium to produce a semisolid material. Where the dispersion medium is water, the gel is referred to as a "hydrogel". Gels may for example be produced by bringing the biopolymer of the invention into solution and allowing the self-assembly thereof into nanofibers. Depending on the structure of the specific biopolymer and on the nature of the dispersion medium, gel-formation may occur at concentrations between 0.1 to 50% (w/v) of the biopolymer of the invention, preferably between 1 to 20% (w/v) of the biopolymer of the invention and most preferably at a concentration between 2 to 10% (w/v) of the biopolymer of the invention. Self-assembly into nanofibres may be enhanced by adding e.g. methanol, such as for example 10% w/v methanol, or other primary alcohols, or glycol. Other exemplary methods to enhance the self assembly are by applying shear forces (such as for example rotation or sonication), by seeding of small preassembled fibrils or by addition of kosmotropic salts such as e.g. phosphate. To improve the mechanical properties of the gel, ammonium peroxodisulfate (APS), and Tris(2,2'-bipyridyl)dichlororuthenium(II) (Rubpy) can be allowed to enter the gel by diffusion to yield final concentrations of, for example, 10 mM APS and 100 μM Rubpy. To gain dimensionally stable gels, the biopolymers may additionally be cross-linked by exposition to visible light, for example from a tungsten lamp for e.g. 1 min.

As used herein, the term "coating" is defined in accordance with the pertinent prior art and relates to a layer spread over a surface for protection or decoration. Coatings may be prepared by distributing, for example spraying, dipping, spinning or casting a solution comprising 0.1 to 50% (w/v) of the biopolymer of the invention, preferably comprising 1 to 20% (w/v) of the biopolymer of the invention and even more preferably comprising 2 to 10% (w/v) of the biopolymer of the invention onto a surface and allowing the solvent to evaporate, as for example described above for films.

The term "particle", as used herein, is defined in accordance with the pertinent prior art and relates to a very small unit, also termed sphere herein. Biopolymeric particles preferably display a diameter ranging between 0.05 and 10 μm. Such particles may be generated for example by salting out with salts according to the Hofmeister series, such as for example adding 0.8 M ammonium sulphate to a solution comprising 0.1 to 50% (w/v) of the biopolymer of the invention, preferably comprising 0.1 to 20% (w/v) and even more preferably comprising 0.1 to 10% (w/v) of the biopolymer of the invention.

As used herein, the term "capsule" is defined in accordance with the pertinent prior art and refers to a vesicular structure. Such capsules find use for example in drug delivery, biomedical devices and flavour encapsulation. Capsules may be prepared from a solution comprising 0.1 to 50% (w/v) of the biopolymer of the invention, preferably comprising 0.1 to 20% (w/v) and even more preferably comprising 0.1 to 10% (w/v) of the biopolymer of the invention. The solution comprising the biopolymer can be emulsified in a solvent, such as e.g. toluene, and the size of the capsules obtained depends on the size of the emulsion droplets. Once formed the biopolymer shells surrounding the emulsion droplets can be transferred from the two-phase emulsion into a one-phase solution, for example by either adding water to the toluene to form an aqueous sublayer or by adding ethanol (95%) to the two-phase emulsion to solubilise the toluene and water, as described for example in Hermanson et al. (Adv. Mater. 2007, 19, 1810-1815).

The term "springs", as used herein, relates to stiff stalks in the shape of a spring. Due to the bending properties of the stalk it is possible to use the spring as a flexible damping material. Springs can be produced by dissolving the polymer in hexafluoroacetone and processing afterwards by pulling out a fibre of a droplet of spinning solution and spooling this on a support as described e.g. in example 9 below.

As used herein, the term "nonwovens", e.g. nonwoven mats, is defined in accordance with the pertinent prior art and refers to fabrics, such as sheets or web structures bonded together by entangling fibres or filaments, e.g. mechanically, thermally or chemically. Nonwoven mats are typically flat, porous sheets that are made directly from separate fibres or films and that are not made by weaving or knitting. Methods of preparing nonwovens, e.g. nonwoven mats, are well known in the art and have been described, for example, in WO 2010/072665.

Methods for generating such foams, films, gels, coatings, particles, capsules, springs or nonwovens mats from the biopolymers of the invention are well known in the art and have been described, e.g. in Hardy et al. 2008, some of which are also shown in the appended examples.

The foams, films, gels, coatings, particles, capsules, springs or nonwovens mats generated in accordance with the present invention find numerous applications, as detailed herein below.

The present invention also relates to fibres comprising or consisting of the biopolymer of the invention or the biopolymer obtained by the method of the invention. Accordingly, the present invention also relates to the use of the biopolymer of the invention or of the biopolymer obtained by the method of the invention for the preparation of fibres.

The term "fibres", as used herein, is defined in accordance with the pertinent prior art and refers to materials that are continuous filaments or discrete elongated pieces. Methods for generating fibres are also well known in the art. For example, wet spun fibres can be produced as shown in example 4 below. Further information about the generation of fibres is described in e.g. WO03060099. Also these fibres generated in accordance with the present invention find numerous applications, as for example detailed herein below.

It is preferred that the fibres comprising the biopolymer of the invention or the biopolymer obtained by the method of the invention comprise one or more cells, such as one or more isolated cells, which may be part of a tissue. Said one or more cells, such as one or more isolated cells, may be incorporated into and/or attached to or associated with said fibres.

Said cells may be prokaryotic cells, e.g. bacteria of the species *Escherichia, Bacillus, Streptomyces* and *Salmonella typhimurium*. Said cells may also be eukaryotic cells, e.g. fungal cells, inter alia, yeasts such as *Saccharomyces cerevisiae* or *Pichia pastoris* or *Hansenula polymorpha* or insect cells such as *Drosophila* S2 cells, *Spodoptera* Sf9 cells, Sf21 cells and High five cells as well as plant cells, e.g. tobacco, potato, corn, pea or tomato cells, and mammalian cells, e.g. mouse NIH3T3 and C127 cells, COS 1, COS 7 and CV1, quail QC1-3 cells, mouse L cells, Chinese hamster ovary (CHO) cells and Bowes melanoma cells.

Said fibres seeded with one or more cells, such as one or more isolated cells, can be used, for example, for artificial nerve regeneration or muscle cell growth.

The biopolymer of the invention, the foams, films, gels, e.g. hydrogels, coatings, particles, capsules, springs or nonwovens, e.g. nonwoven mats, of the invention as well as the fibres of the invention are also referred to herein as the biopolymeric compounds of the invention.

The present invention also relates to a method of producing (a) fibre(s), comprising (i) dissolving the biopolymer of the invention or obtained by the method of the invention in a solvent thereby obtaining a solution comprising said biopolymer; and (iia) extracting (a) fibre(s) from the solution of (i), (iib) extruding (a) fibre(s) from the solution of (i), or (iic) spinning (a) fibre(s) out of the solution of (i).

Preferably, the solvent is an organic solvent or an organic acid. More preferably, the organic solvent is Hexafluoroisopropanol (HFIP) or Hexafluoroacetone (HFA) or the organic acid is formic acid.

Thus, in one embodiment, the invention relates to a method of producing (a) fibre(s), comprising (i) dissolving the biopolymer of the invention or obtained by the method of the invention in a solvent thereby obtaining a solution comprising said biopolymer; and (ii) extracting (a) fibre(s) from the solution of (i).

Preferably, the method of producing (a) fibre(s), comprises (i) dissolving the biopolymer of the invention or obtained by the method of the invention in Hexafluoroacetone (HFA); and (ii) extracting (a) fibre(s) from the solution of (i).

As described in the examples below, this method may be carried out dissolving 10% w/v of the inventive biopolymer in HFA and then pulling fibres out of a droplet of this solution and attaching them to a contact point suspended above the droplet. The fibres thus obtained are subsequently dried at room temperature and tension is removed from the fibres by moving the contact points closer to the surface with the droplet. The samples may further be placed overnight in a climate chamber at approximately 60° C. and 70% relative humidity (RH).

In accordance with the present invention, it was found that the biopolymer of the present invention can be dissolved in HFA and processed into β-sheet rich structures, underlying the biophysical properties of the inventive biopolymer. This finding is surprising, as HFA is well known in the art to induce α-helical structures in solution. (J. M. Yao, H. Masuda, C. H. Zhao, T. Asakura, *Macromolecules* 2002, 35, 6.).

In another embodiment, the invention relates to a method of producing (a) fibre(s), comprising (i) dissolving the biopolymer of the invention or obtained by the method of the invention in a solvent thereby obtaining a solution comprising said biopolymer; and (ii) extruding (a) fibre(s) from the solution of (i).

Preferably, the fibre(s) is (are) extruded in a coagulation bath. It is preferred that the coagulation bath comprises methanol, ethanol, isopropanol, or an aqueous solution of kosmotropic salts, e.g. sulfate or phosphate salts. The production of (a) fibre(s) by extruding (a) fibre(s) from the solution of (i) in a coagulation bath may also be designated as wet spinning. The wet spinning process is exemplarily described in example 4.

The resulting fibre(s) may be post spun, e.g. immediately in the coagulation bath or in a post spinning solution such as water or additional coagulation solutions (e.g. 70% isopropanol in water).

In a further embodiment, the invention relates to a method of producing (a) fibre(s), comprising (i) dissolving the biopolymer of the invention or obtained by the method of the invention in a solvent thereby obtaining a solution comprising said biopolymer; and (ii) spinning (a) fibre(s) (directly) out of the solution of (i). Preferably, the fibre(s) is (are) electrospun out of the solution of (i).

The term "ectrospinning" refers to a process which uses an electrical charge to draw very fine (typically on the micro or nano scale) fibres from a solution. Electrospinning shares characteristics of both electrospraying and conventional solution dry spinning of fibers. The process does not require the use of coagulation chemistry or high temperatures to produce fibres from a solution.

The present invention further relates to the biopolymer of the invention, or the biopolymer obtained by the method of the invention, or the foams, films, gels, e.g. hydrogels, coatings, particles, capsules, springs or nonwovens, e.g. nonwoven mats, or the fibres of the invention for use in medicine.

Medical uses in accordance with the present invention include, without being limiting, the use in tissue engineering, in medical devices as well as in drug delivery.

Tissue engineering includes for example wound closure systems, hemostatic dressings or prosthetic devices such as e.g. replacement ligaments. Tissues engineering may be carried out as e.g. skin grafts or cellular growth matrices. Medical devices include for example implants, sutures, stents or surgical mesh. Furthermore, for drug delivery the biopolymer or foams, films, gels, coatings, particles, capsules, springs, nonwovens mats or fibres made thereof may be employed as a scaffold for into which drugs such as e.g. cytokines can be incorporated.

For example, the biopolymer of the present invention or foams, films, gels, e.g. hydrogels, coatings, particles, capsules, springs, nonwovens, e.g. nonwoven mats, or fibres made thereof, can be used as a matrix for prosthetic devices. As an example, the biopolymeric films as described in example 4 below may be employed and cells can be seeded onto such films. Moreover, directional layers or films can be produced as shown in Example 7, onto which cells are deposited. Cells will grow in between the film stripes and align with such structured templates and can subsequently be used for example for artificial nerve regeneration or muscle cell growth. Other applications include ligaments and tendons, cartilage, bone, muscle, skin or blood vessels.

Alternatively, the biopolymer of the present invention or foams, films, gels, coatings, particles, capsules, springs, nonwovens mats or fibres made thereof, can be used to coat a material used as wound dressing. Preferred amounts of the biopolymer to be employed can be determined by the skilled person without further ado. Preferably, coats of a thickness between 0.01 μm and 1000 μm are employed in order to promote wound healing. Methods for achieving the wound dressing are well known in the art and include, without being limiting dipping, spraying, lubricating etc.

Drugs that may be delivered employing the biopolymer of the present invention or foams, films, gels, coatings, particles, capsules, springs, nonwovens mats or fibres made thereof are known to the person skilled in the art. Exemplary drugs include, without being limiting, therapeutic and protective agents, such as e.g. any agent selected from the group comprising: an antimicrobial agent, an antibiotic, an anti-viral agent, anti-fungal agent, an urinary tract antiseptic, an agent for treating anaerobic infections, an agent for treating tuberculosis, an agent for treating leprosy, an agent for treating amebiasis, an anti-malarial agent, an anti-helminthiasis agent, an anti-gout agent, a thrombin inhibitors, an antithrombogenic agent, a thrombolytic agent, a fibrinolytic agent, a vasospasm inhibitor, a vasodilator, an antihypertensive agent, an antihypotensive agent, an inhibitors of surface glycoprotein receptor, an antiplatelet agent, an antimitotic, an actin inhibitors, a microtubule inhibitor, an anti secretory agent, a remodeling inhibitor, an antimetabolite, an antiproliferative (including anti-angiogenesis) agents, an immunosuppressive agent, a growth hormone antagonist, a growth factor, a dopamine agonist, a radiotherapeutic agent, a extracellular matrix component, an ACE inhibitor, a free radical scavenger, a chelator, an antioxidant, an antipolymerase, a photodynamic therapy agent, a centrally active muscle relaxant, an opioid agonist, a non-opioid analgesic, a non-steroid anti-inflammatory agent, an antimigraine agent, a Cox-II inhibitor, an antiemetic, a β-adrenergic blocker, a $Ca^{2+}$-channel blocker, an anticonvulsant, an antidepressant, an anticancer agent, an agent for treating or preventing urinary incontinence (UI), an agent for treating or preventing an ulcer, an agent for treating or preventing infectious bursal disease (IBD), an agent for treating or preventing irritable bowel syndrome (IBS), an agent for treating addictive disorder, an agent for treating Parkinson's disease and parkinsonism, an agent for treating anxiety, an agent for treating epilepsy, an agent for treating a stroke, an agent for treating a seizure, an agent for treating a pruritic condition, an agent for treating psychosis, an agent for treating Huntington's chorea, an agent for treating amytrophic lateral sclerosis (ALS), an agent for treating a cognitive disorder, an agent for treating a migraine, an agent for treating vomiting, an agent for treating dyskinesia, an agent for treating depression, an anorexic, an antacid, antiacne agents, an antiallergic, an antianginal agent, an antiarrythmic, an antiasthmatic, an antibaldness agent, an anticholinergic agent, an anticoagulant and blood thinner, an anticolitis agent, an anticystitis agent, an antidiabetic agent, an antidiarrheal, an antidiuretic, an antiflatulent, an antiglaucoma agent, an antihistaminic, an antipneumonia agent, an antiobesity agent, an antipsoriatics, an antipsychotic, an antipyretic, an antirheumatic, an antitussive, a bone densifier, a carbonic anhydrase inhibitor, a cardiotonic, a contraceptive, a decongestant, a diuretic, a CNS stimulant, a dopamine receptor antagonist, an HMG CoA reductase inhibitor, a phosphodiesterase inhibitor, a hormone, a hormone antagonist, a hematopoietic agent, an immunomodulator, an immunosuppressant, a laxative, an agent for treating multiple sclerosis, a sedative, a serotonin uptake inhibitor, and mixtures thereof.

It will be appreciated by the skilled person that in the medical uses described herein, further compounds will be included in addition to the biopolymer of the invention. For example, and as described above, specific medicaments for the treatment of a particular disease may be included. In addition, non-specific medical compounds may be included, such as e.g. disinfectants.

Accordingly, the present invention also relates to a pharmaceutical composition comprising the biopolymer of the invention, or the biopolymer obtained by the method of the invention, or the foams, films, gels, e.g. hydrogels, coatings, particles, capsules, springs or nonwovens, e.g. nonwoven mats, or the fibres of the invention.

In accordance with the present invention, the term "composition" relates to a composition which comprises at least one of the compounds of the invention. It may, optionally, comprise further molecules capable of altering the characteristics of the compounds of the invention thereby, for example, stabilizing, delaying, modulating and/or activating their function. The composition may be in solid, liquid or gaseous form and may be, inter alia, in the form of (a) powder(s), (a) tablet(s), (a) solution(s) or (an) aerosol(s).

The term "pharmaceutical composition", as used herein, relates to a composition for administration to a patient, preferably a human patient or an animal, e.g. a pet such as dogs, cats, rodents, etc. The pharmaceutical composition of the invention comprises the compounds recited above, preferably in combination with a pharmaceutically active compound.

The composition may e.g. be in solid or liquid form and may be, inter alia, in the form of (a) powder(s), (a) tablet(s), (a) solution(s) or (an) aerosol(s).

The pharmaceutical composition of the present invention may, optionally and additionally, comprise a pharmaceutically acceptable carrier, particularly for the pharmaceutically active compound.

By "pharmaceutically acceptable carrier" is meant a non-toxic solid, semisolid or liquid filler, diluent, encapsulating material or formulation auxiliary of any type. Examples of suitable pharmaceutically acceptable carriers are well known in the art and include phosphate buffered saline solutions, water, emulsions, such as oil/water emulsions, various types of wetting agents, sterile solutions, organic solvents including DMSO etc. Compositions comprising such carriers can be formulated by well known conventional methods.

Pharmaceutical compositions of the invention may for example be administered orally, parenterally, intraperitoneally, topically (as by powders, ointments, drops or transdermal patch), bucally, or as a nasal spray.

The term "parenteral" as used herein refers to modes of administration, which include intravenous, intramuscular, intrasternal, subcutaneous and intraarticular injection and infusion.

Furthermore, the present invention also relates to the biopolymer of the invention, or the biopolymer obtained by the method of the invention, or the foams, films, gels, e.g. hydrogels, coatings, particles, capsules, springs or nonwovens, e.g. nonwoven mats, or the fibres of the invention for use in the treatment of infections such as bacterial, viral or fungal infections, malaria, helminthiasis, gout, migraine, depression, cancer, ulcer, addictive disorders, Parkinson's disease (PD), Alzheimer's disease, anxiety, epilepsy, stroke, seizure, pruritus, psychosis, Huntington's chorea, Amyotrophic lateral sclerosis (ALS), cognitive disorders, vomiting, dyskinesia and other diseases curable by the drugs recited herein above.

All of the diseases described herein are well known to the skilled person and are defined in accordance with the prior art and the common general knowledge of the skilled person. A detailed description of suitable drugs for the treatment of the above referenced diseases may for example be found in WO 2011/063990.

The present invention further relates to the biopolymer of the invention, or the biopolymer obtained by the method of the invention, or the foams, films, gels, e.g. hydrogels, coatings, particles, capsules, springs or nonwovens, e.g. nonwoven mats, or the fibres of the invention for use in agriculture.

Agricultural uses include, without being limiting, the use of the biopolymer of the invention, or the biopolymer obtained by the method of the invention, or the foams, films, gels, e.g. hydrogels, coatings, particles, capsules, springs or nonwovens, e.g. nonwoven mats, or the fibres of the invention as a carrier and/or enhancer for herbicides, insecticides and/or fungicides or animal foods.

The biopolymeric composition of the present invention, i.e. the biopolymer of the invention, or the biopolymer obtained by the method of the invention, or the foams, films, gels, e.g. hydrogels, coatings, particles, capsules, springs or nonwovens, e.g. nonwoven mats, or the fibres of the invention, may for example serve as a protector of the herbicides, insecticides and/or fungicides or animal foods. It may for example protect these compounds from environmental influences such as e.g. oxidative processes or UV radiation as well as from reactions with other constituents of the composition or degradation via e.g. enzymes. Release of the herbicides, insecticides and/or fungicides can for example be achieved via desorption, proteolytic degradation, immediate or sustained release or a combination of these methods. The biopolymeric composition of the present invention may also serve as an enhancer of the activity of the herbicides, insecticides and/or fungicides. For example, bioavailability of the compounds may be increased due to formulation with the biopolymeric composition of the present invention, or absorption in the body of the targeted insects or fungi may be improved. Suitable compositions for agricultural uses have been described in the art, for example in WO2007/082936.

The present invention further relates to the biopolymer of the invention, or the biopolymer obtained by the method of the invention, or the foams, films, gels, e.g. hydrogels, coatings, particles, capsules, springs or nonwovens, e.g. nonwoven mats, or the fibres of the invention for use in cosmetics.

Cosmetic uses, in accordance with the present invention, include without being limiting skin care, skin cleansing such as e.g. soap; hair care such as e.g. shampoo, conditioner or dyes; make-up such as e.g. foundation, lip-stick, mascara; creams and emulsions, such as e.g. compositions for moisturising or tanning as well as sunscreens; but also nail varnish, perfumes, dental hygiene products or products for showering/bathing.

Accordingly, the present invention also relates to a cosmetic composition comprising the biopolymer of the invention, or the biopolymer obtained by the method of the invention, or the foams, films, gels, e.g. hydrogels, coatings, particles, capsules, springs or nonwovens, e.g. nonwoven mats, or the fibres of the invention.

The term "cosmetic composition", as used herein, relates to a composition for administration to a patient, preferably a human patient or an animal such as a pet, e.g. dogs, cats, rodents etc. The cosmetic composition of the invention comprises the compounds recited above, alone or in combination. The composition may e.g. be in solid or liquid form and may be, inter alia, in the form of (a) powder(s), (an) emulsion), (a) solution(s) or (an) aerosol(s).

The cosmetic composition of the present invention may, optionally and additionally, comprise a cosmetically acceptable carrier.

By "cosmetically acceptable carrier" is meant a non-toxic solid, semisolid or liquid filler, diluent, encapsulating material or formulation auxiliary of any type. Examples of suitable cosmetically acceptable carriers are the same carriers as defined herein above as therapeutically acceptable carriers.

Cosmetic compositions of the invention may for example be administered orally, parenterally, intravenously, topically (as by powders, ointments, drops or transdermal patch), or as a nasal spray. These cosmetic compositions can be administered to the subject at a suitable dose. The dosage regimen can be easily determined by the skilled person depending on the type of cosmetic composition and is preferably in the range of between about 0.0001 to about 30% by weight, more preferably between about 0.001 to about 15% by weight, more preferably between about 0.01 to about 10% by weight and most preferably between about 0.1 and 3% by weight.

Moreover, the present invention also relates to the biopolymer of the invention, or the biopolymer obtained by the method of the invention, or the foams, films, gels, e.g. hydrogels, coatings, particles, capsules, springs or nonwovens, e.g. nonwoven mats, or the fibres of the invention for use in surface, paper, leather and/or textile processing.

In accordance with the present invention, any of the compounds of the invention may be added to surfaces such as wooden panels, furniture, plastics, building and automotive parts etc. in order to reinforce that surface. Means and methods for coating a surface are well known in the art and include, without being limiting dipping, spraying, lubricating etc. Moreover, the compounds of the invention may also be employed in the process of paper making, in order to add strength and quality to the paper. In order to do so, the biopolymer or biopolymeric compounds of the invention is mixed into the cotton pulp during the preparation process.

Textiles, such as e.g. tights but also sports and leisure clothing as well as protective work clothing can also be processed with the biopolymeric compounds of the invention. One method involves applying them onto the surface of threads, such as e.g. textile fibres of cotton, rayon, nylon, wool and other fibres from which textiles are made, thus providing a smooth surface and good feel. Alternatively, the biopolymeric compounds of the invention are applied to the woven fabric. Coating may be achieved as described herein above for the coating of surfaces. Due to the extensibility and toughness of the biopolymeric compounds of the invention and the fact that they maintain this properties when wet, they provide superior wearing comfort and durability to the textiles.

Moreover, the biopolymeric compounds of the invention also confer stability and durability to leather products, thereby avoiding or reducing tanning and its negative effects for environment.

The invention further relates to a surface, paper, leather and/or textile processing composition comprising the biopolymer of the invention, or the biopolymer obtained by the method of the invention, or the foams, films, gels, e.g. hydrogels, coatings, particles, capsules, springs or nonwovens, e.g. nonwoven mats, of the invention, or the fibres of the invention, or the fibres obtained by the method of the invention.

Said composition may be added to surfaces such as wooden panels, furniture, plastics, building and automotive parts etc. in order to reinforce those surfaces. Said composition may also be employed in the process of paper making, in order to add strength and quality to the paper. For example, said composition may be mixed into the cotton pulp during the preparation process. Textiles, such as e.g. tights but also sports and leisure clothing as well as protective work clothing can also be processed with said composition. Said composition may be applied onto the surface of threads, such as e.g. textile fibres of cotton, rayon, nylon, wool and other fibres from which textiles are made, thus, providing a smooth surface and good feel. Alternatively, said composition may be applied to the woven fabric.

Furthermore, the invention relates to a medical device comprising or consisting of the biopolymer of the invention, or the biopolymer obtained by the method of the invention, or the foams, films, gels, e.g. hydrogels, coatings, particles, capsules, springs or nonwovens, e.g. nonwoven mats, of the invention, or the fibres of the invention, or the fibres obtained by the method of the invention.

The biopolymer of the invention, the biopolymer obtained by the method of the invention, or the foams, films, gels, e.g. hydrogels, coatings, particles, capsules, springs or nonwovens, e.g. nonwoven mats, of the invention may form the scaffold or the matrix of the medical device. Alternatively, the medical device may be coated with the biopolymer of the invention or with the biopolymer obtained by the method of the invention.

Preferably, the medical device is selected from the group consisting of an implant, a wound closure system, prosthetic device, suture, stent, or surgical mesh.

Thus, for example, the stent or implant may be coated with the biopolymer of the invention, or the biopolymer obtained by the method of the invention. The wound closure system, the suture or surgical mesh may consist of or may be made from the biopolymer of the invention or from the biopolymer obtained by the method of the invention.

In addition, the invention relates to a drug delivery system comprising the biopolymer of the invention, or the biopolymer obtained by the method of the invention, or the foams, films, gels, e.g. hydrogels, coatings, particles, capsules, springs or nonwovens, e.g. nonwoven mats, of the invention, or the fibres of the invention, or the fibres obtained by the method of the invention.

The biopolymer of the invention, the biopolymer obtained by the method of the invention, or the foams, films, gels, e.g. hydrogels, coatings, particles, capsules, springs or nonwovens, e.g. nonwoven mats, of the invention may form the scaffold or the matrix of the drug delivery device. This means that the drugs may be incorporated into and/or attached to, bound to or associated with said biopolymer of the invention, the biopolymer obtained by the method of the invention, or the foams, films, gels, e.g. hydrogels, coatings, particles, capsules, springs or nonwovens, e.g. nonwoven mats, of the invention.

For example, the drugs may be incorporated into and/or attached to, bound to or associated with the particles of the invention. The drugs may also be encapsulated in and/or attached to, bound to or associated with the capsules of the invention. The drugs may further be incorporated in the films, e.g. in single-layer or multi-layer form, and/or attached to, bound to or associated with the films, e.g. in single-layer or multi-layer form, of the invention.

The above mentioned forms/structures are superior when the drug must be isolated from its surroundings, as in isolating drugs from the deteriorating effects of oxygen, retarding evaporation of a volatile drug, improving the handling properties of a sticky drug, or isolating a reactive drug from chemical attack. In other cases, the objective is not to isolate the drug completely but to control the rate at which it leaves the capsule, as in the controlled release of drugs. The problem may be as simple as masking the taste or odor of the drug, or as complex as increasing the selectivity of an adsorption or extraction process.

The drugs may be released in vivo (after administration to a patient in need thereof) chemically, physically (for example by shear forces) or biologically (by proteolytic digestion).

Drugs that may be delivered are known to the person skilled in the art. Exemplary drugs include, without being limiting, therapeutic and protective agents, such as e.g. any agent selected from the group comprising: an antimicrobial agent, an antibiotic, an anti-viral agent, anti-fungal agent, an antiproliferative (including anti-angiogenesis) agent, an immunosuppressive agent, a growth hormone antagonist, a growth factor, a radiotherapeutic agent, a free radical scavenger, a chelator, an antioxidant, an antiallergic, an antianginal agent, an antiarrythmic, an antiasthmatic, an antibaldness agent, an anticholinergic agent, an anticoagulant and blood thinner, an anticolitis agent, an anticystitis agent, an antidiabetic agent, an antidiarrheal, an antidiuretic, an antiflatulent, an antiglaucoma agent, an antihistaminic, an antipneumonia agent, an antiobesity agent, an antipsoriatics, an antipsychotic, an antipyretic, an antirheumatic, an antitussive, a hormone, a hormone antagonist, a hematopoietic agent, an immunomodulator, an immunosuppressant, a laxative, a sedative, and mixtures thereof. Further examples of drugs can be taken from the above listing.

The invention is summarized as follows:

1. A biopolymer comprising or consisting of at least two repeats of an amino acid sequence comprising or consisting of:

(a) the amino acid sequence of formula I:

Gly-Ser-$X_1$-$X_2$-Ala-$X_3$-Ser-$X_4$-$X_5$-Ser-$X_6$-Ala-$X_7$-Ala-$X_8$-Lys-$X_9$-$X_{10}$-Ala-$X_{11}$-Ala-$X_{12}$-Ser-$X_{13}$-$X_{14}$-Ser-Thr-Ala-$X_{15}$-Ala-Ser-Lys-Gly-Ser-Ala-$X_{16}$-Ala-$X_{17}$-Ser-$X_{18}$-$X_{19}$-Ser-Thr-Ala-$X_{20}$-Ala-$X_{21}$-Lys (formula I)

wherein:

$X_1$ is selected from the group consisting of Ala and Ser;

$X_2$ and $X_3$ are each independently selected from the group consisting of Gly, Ser, Thr and Val;

$X_4$ is selected from the group consisting of Asn, Gly, Gln and Asp;

$X_5$, $X_{13}$, $X_{14}$, $X_{18}$ and $X_{19}$ are each independently selected from the group consisting of Gly and Asn;

$X_6$, $X_{11}$, $X_{12}$, $X_{15}$, $X_{16}$, and $X_{20}$ are each independently selected from the group consisting of Gly, Ser, Thr, Ala and Val $X_7$ is selected from the group consisting of Ser, Thr and Ala;

$X_8$ and $X_{21}$ are each independently selected from the group consisting of Ser and Thr;

$X_9$ is selected from the group consisting of Gly and Asp;

$X_{10}$ is selected from the group consisting of Ser, Ala and Gly; and $X_{17}$ is selected from the group consisting of Ser, Thr, Ala and Val;

and wherein at least one of $X_4$ and $X_5$ is Gly;

at least one of $X_{13}$ and $X_{14}$ is Gly; and at least one of $X_{18}$ and $X_{19}$ is Gly; and/or (b) a variant of the amino acid sequence of (a), wherein the variant differs from the amino acid sequence of (a) in 1 to 10 amino acids and wherein the variations are selected from the group consisting of substitutions, deletions, insertions and/or additions and wherein the variations do not or do not substantially reduce the biophysical properties of the biopolymer formed as compared to a biopolymer comprising or consisting of repeats of the amino acid sequence of (a), wherein the biophysical properties are at least one of the ability of the biopolymer to stay in solution, the processability of the biopolymer and the tensile strength, extensibility, Young's modulus/stiffness and/or toughness of fibres produced from the biopolymer of the invention.

2. The biopolymer of item 1, wherein the amino acid sequence of formula I is selected from the group consisting of:

(i) the amino acid sequence of SEQ ID NO:1;

(ii) an amino acid sequence having at least 91% sequence identity to the amino acid sequence of SEQ ID NO:1;

(iii) an amino acid sequence encoded by a nucleic acid molecule of SEQ ID NO: 2;

(iv) an amino acid sequence encoded by a nucleic acid sequence that hybridizes under stringent conditions to the complementary strand of the nucleic acid sequence of SEQ ID NO:2; and (v) an amino acid sequence encoded by a nucleic acid sequence that is degenerate with respect to the nucleic acid sequence of (iii) or (iv); and (vi) a variant of the amino acid sequence of (i), wherein the variant differs from the amino acid sequence of (i) in 1 to 10 amino acids, wherein the variations are selected from the group consisting of substitutions, deletions, insertions and/or additions and wherein the variations do not or do not substantially reduce the biophysical properties of the biopolymer formed with this repeat sequence as compared to a biopolymer formed with a repeat sequence comprising or consisting of the amino acid sequence of (i), wherein the biophysical properties are at least one of the ability of the biopolymer to stay in solution, the processability of the biopolymer and the tensile strength, extensibility, Young's modulus/stiffness and/or toughness of fibres produced from the biopolymer of the invention.

3. The biopolymer of item 1 or 2, further comprising an N- and/or C-terminal polypeptide.

4. The biopolymer of item 3, wherein the N-terminal polypeptide is selected from the group consisting of:

(i) an amino acid sequence comprising or consisting of the amino acid sequence of any one of SEQ ID NO:3 to SEQ ID NO:18;

(ii) an amino acid sequence having at least 80% sequence identity to the amino acid sequence of (i);

(iii) an amino acid sequence encoded by a nucleic acid molecule comprising or consisting of the sequence of any one of SEQ ID NO:19 to SEQ ID NO:34;

(iv) an amino acid sequence encoded by a nucleic acid sequence that hybridizes under stringent conditions to the complementary strand of a nucleic acid sequence of (iii);

(v) an amino acid sequence encoded by a nucleic acid sequence that is degenerated with respect to the nucleic acid sequence of (iii) or (iv); and (vi) a variant of the amino acid sequence of (i), wherein the variant differs from the amino acid sequence of (i) in 1 to 10 amino acids and wherein the variations are selected from the group consisting of substitutions, deletions, insertions and/or additions and wherein the variations do not or do not substantially reduce the biophysical properties of the biopolymer formed with this N-terminal polypeptide as compared to a biopolymer formed with an N-terminal polypeptide comprising or consisting of the amino acid sequence of (i), wherein the biophysical properties are at least one of the ability of the biopolymer to stay in solution, the processability of the biopolymer and the tensile strength, extensibility, Young's modulus/stiffness and/or toughness of fibres produced from the biopolymer of the invention.

5. The biopolymer of item 3 or 4 wherein the C-terminal polypeptide is selected from the group consisting of:

(i) an amino acid sequence comprising or consisting of the amino acid sequence of any one of SEQ ID NO:35 to SEQ ID NO:50;

(ii) an amino acid sequence having at least 80% sequence identity to the amino acid sequence of (i)

(iii) an amino acid sequence encoded by a nucleic acid molecule comprising or consisting of the sequence of any one of SEQ ID NO:51 to SEQ ID NO:66;

(iv) an amino acid sequence encoded by a nucleic acid sequence that hybridizes under stringent conditions to the complementary strand of a nucleic acid sequence of (iii); and (v) an amino acid sequence encoded by a nucleic acid sequence that is degenerate with respect to the nucleic acid sequence of (iii) or (iv); and (vi) a variant of the amino acid sequence of (i), wherein the variant differs from the amino acid sequence of (i) in 1 to 10 amino acids and wherein the variations are selected from the group consisting of substitutions, deletions, insertions and/or additions and wherein the variations do not or do not substantially alter the biophysical properties of the biopolymer formed with this C-terminal polypeptide as compared to a biopolymer formed with a C-terminal polypeptide comprising or consisting of the amino acid sequence of (i), wherein the biophysical properties are at least one of the ability of the biopolymer to stay in solution, the processability of the biopolymer and the tensile strength, extensibility, Young's modulus/stiffness and/or toughness of fibres produced from the biopolymer of the invention.

6. A nucleic acid molecule encoding the biopolymer of any one of items 1 to 5.

7. A vector comprising the nucleic acid molecule of item 6.

8. A non-human host transformed with the vector of item 7.

9. The non-human host of item 8, wherein the host is a cell.

10. A method for the production of a biopolymer according to any one of items 1 to 5, comprising culturing the non-human host cell of item 9 under suitable conditions and isolating the biopolymer produced.

11. Foams, films, gels, coatings, particles, capsules, springs or nonwovens mats comprising or consisting of the biopolymer according to any one of items 1 to 5 or the biopolymer obtained by the method of item 10.

12. Fibres comprising or consisting of the biopolymer of any one of items 1 to 5 or the biopolymer obtained by the method of item 10.

13. A method of producing (a) fibre(s), comprising (i) dissolving the biopolymer of any one of items 1 to 5 or obtained by the method of item 10 in hexa fluoro acetone (HFA); and (ii) extracting (a) fibre(s) from the solution of (i).

14. The biopolymer of any one of items 1 to 5, or the biopolymer obtained by the method of item 10, or the foams, films, gels, coatings, particles, capsules, springs or nonwovens mats of item 11 or the fibres of item 12 or the fibres obtained by the method of item 13 for use in medicine.

15. The biopolymer of any one of items 1 to 5, or the biopolymer obtained by the method of item 10, or the foams, films, gels, coatings, particles, capsules, springs or nonwovens mats of item 11 or the fibres of item 12 or the fibres obtained by the method of item 13 for use in agriculture.

16. The biopolymer of any one of items 1 to 5, or the biopolymer obtained by the method of item 10, or the foams, films, gels, coatings, particles, capsules, springs or nonwovens mats of item 11 or the fibres of item 12 or the fibres obtained by the method of item 13 for use in cosmetics.

17. The biopolymer of any one of items 1 to 5, or the biopolymer obtained by the method of item 10, or the foams, films, gels, coatings, particles, capsules, springs or nonwovens mats of item 11 or the fibres of item 12 or the fibres obtained by the method of item 13 for use in surface, paper, leather and/or textile processing.

Unless otherwise defined, all technical and scientific terms used herein have the same meaning as commonly understood by one of ordinary skill in the art to which this invention pertains. In case of conflict, the present specification, including definitions, will control.

EXAMPLES

The examples illustrate the invention:

Example 1

Material and Methods

Preparation of a Biopolymer in Accordance with the Present Invention.

Figure 6:
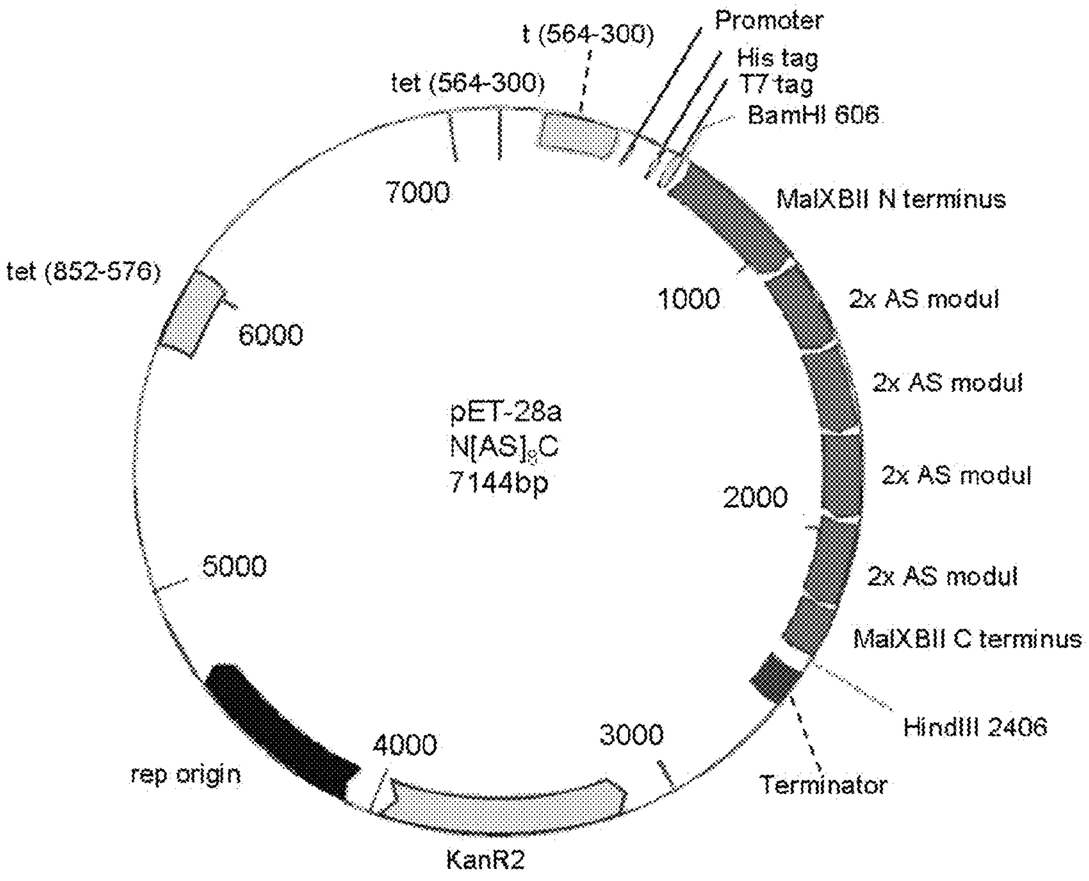
FIG. 6: Vector map of N[AS]$_8$C in a pET28 vector.

The modules encoding an exemplary biopolymer of the invention, referred to herein as $N[AS]_8C$ (N=N-terminus: SEQ ID NO: 68, C=C-terminus: SEQ ID NO: 35, and AS=AS module: SEQ ID NO: 1 repeated 8 times), were designed with a 5' BamHI and a 3' HindIII restriction site. Modules were cloned using the enzymes BsaI, BsgI and BseRI followed by ligation (Huemmerich et al. 2004). The complete construct was transferred to a pET28 vector using BamHI and HindIII (see e.g. FIG. 6). The modules encoding the exemplary biopolymer of the invention are also shown in FIG. 1.

BL21 (DE3) cells were transformed with the pET28 $N[AS]_8C$ described above and grown in a fermenter (Infors Minifors 2.51) using a protocol described previously (Korz et al. 1995). At an OD600 of 72 the bacteria were induced with 1 mM IPTG for 3 hours. Cells were harvested and washed three times.

Figure 7:
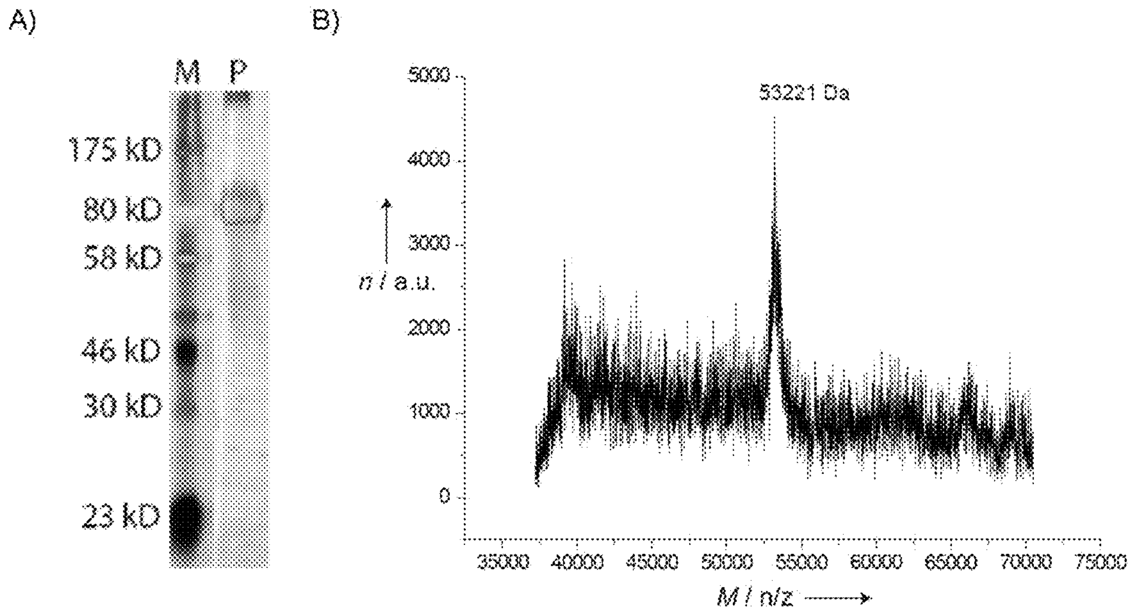
FIGS. 7A-7B: MALDI-TOF analysis of N[AS]$_8$C.

Purification was performed after adopting and optimizing a protocol described previously (Xia et al. 2010). Cells were lysed in a buffer containing 1 mM Tris/HCl pH 8, 20 mM $NaH_2PO_4$, 8 M urea and 2 M thiourea for at least 6 hours or over night. DNA and some proteins were precipitated by acidification to pH 4 with glacial acetic acid (2 hours), followed by centrifugation at 30000 g for 20 minutes. The supernatant was subjected a fractional ammonium sulphate precipitation (1.5 M and 2.5 M ammonium sulphate; incubation for one hour; centrifugation at 30000 g for 20 minutes). The resulting pellet of the 2.5 M ammonium sulfate was washed several times with water and the purified protein was lyophilized. The protein was identified by SDS-PAGE followed by silver staining (FIG. 7A), and mass spectrometric analysis (FIG. 7B).

Preparation of Stalks from the Biopolymer of the Invention

Stalks were pulled out of a droplet of 10% w/v of $N[AS]_8C$ in HFA and dried at room temperature. Afterwards tension was removed from the stalk by moving the contact points closer, and the samples were placed overnight in a climate chamber at 60° C. and 70% RH.

Analysis of Biophysical Properties

For scanning electron microscopy samples were sputter coated with platinum (thickness 2 nm). SEM Pictures were taken at a Zeiss 1530 using the inlens detector.

Fourier transformed infrared spectroscopy (FTIR) was performed using a Bruker tensor 27/pike MIRacle using the Hyperion. Data processing and Fourier self deconvolution of the amide I region was performed using the Opus 6.5 software (Hu et al. 2006). Polarized FTIR measurements and processing of the data was carried out according to Hagenau et al. 2011.

Microscopic pictures were taken with a microscope (Leica DMI 3000B) equipped with polarisers.

Samples for tensile testing were glued onto plastic frames having a gauge length of 2 mm with modelling glue. Stress strain curves were recorded on a tensile tester (Bose Electroforce 3220) equipped with a 0.5 N load cell using a climate chamber to adjust the relative humidity. The stalks were extended with a rate of 0.01 mm/s until rupture.

Circular dichroism spectra were recorded from 250 nm to 195 nm using a Jasco J-815 CD Spectrometer measuring with an interval of 0.1 nm, a bandwidth of 1 nm, a scanning speed of 50 nm/min and three accumulations.

For mass spectrometric analysis 3 mg/ml of $N[AS]_8C$ were dissolved in guanidinium thiocyanate, the solution was desalted with Zip Tip C4 (Millipore) and subsequently characterized by MALDI-TOF

Example 2

Preparation of a Novel Biopolymer

Lacewings use silk for egg stalks. In contrast to other silks, egg stalk silk has a cross-beta structure, which has been determined already in 1957 (Parker and Rudall, 1957). Since then, only a few additional cross-beta silks have been detected (Craig, 1997). At high humidity lacewing egg stalks are highly extensible and have a good toughness, whereas under dry conditions they are quite stiff. For the production of egg stalks, the lacewing simply deposits a droplet of silk dope on a surface and dips in an egg. Pulling the egg creates a filament which hardens within a few seconds. Normally stalks hang downwards from leaves, but if turned around they won't bend under the load of the egg.

In order to biomimetically produce an egg stalk with similar properties, an artificial egg stalk biopolymer was engineered and recombinantly produced. A consensus module for the core domain was identified, which was named AS. The module comprises 48 amino acids. The corresponding gene module was then multimerized to mimic the repetitive core using a seamless cloning technique as previously described (Huemmerich et al. 2004). Sequences for the terminal domains were fused yielding an engineered gene for bacterial expression with a codon usage optimized for *E. coli*. The engineered construct was named $N[AS]_8C$ containing eight repeats of module AS and both N- and C-terminal polypeptides leading to a molecular weight of 53 kD. Although SDS-PAGE analysis revealed an apparently higher molecular weight for $N[AS]_8C$ than calculated, mass spectrometry confirmed the correct mass of the protein (FIGS. 7A-7B).

Example 3

Stalk Formation

Figure 2:
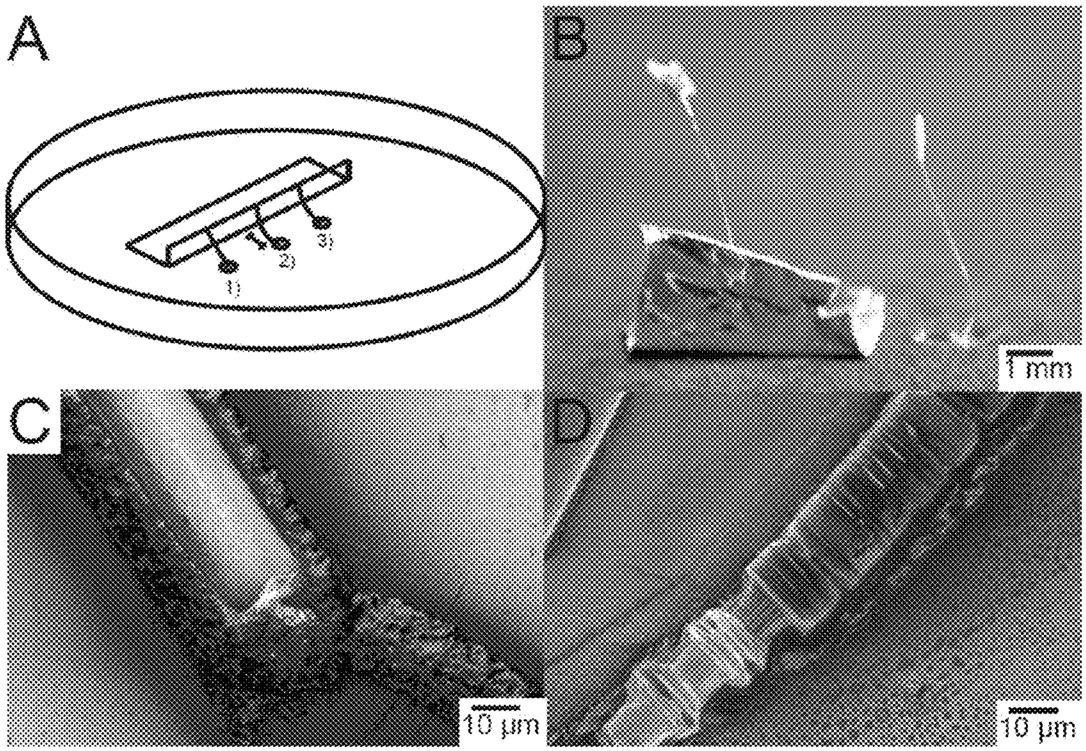
FIGS. 2A-2D.
Figure 8:
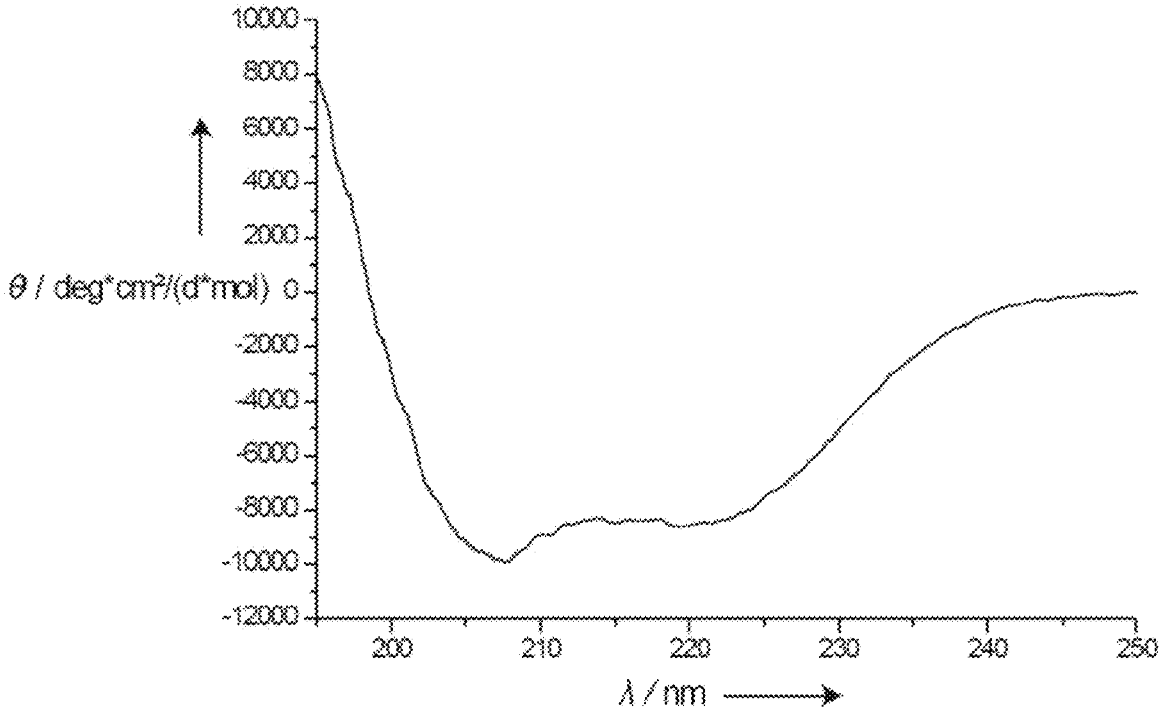
FIG. 8: CD spectrum of N[AS]$_8$C solubilized in HFA.

For stalk formation, 10% w/v $N[AS]_8C$ were dissolved in hexafluoroacetone (HFA). In solution the protein shows an alpha helical structure as detected by CD-spectroscopy (FIG. 8). Induction of alpha-helix formation by HFA has been also previously shown for other proteins (Yao et al. 2002). Mimicking the silk stalk formation of lacewings, tweezers were dipped in a droplet of silk solution. The resulting stalk was transferred to a tinfoil support followed by drying (FIG. 2A). For post treatment, stalks were placed in a climate chamber at 60° C. and 70% relative humidity overnight.

To obtain natural egg stalks a mixture of male and female lacewings was kept in polystyrene dishes together with a moist paper towel and a food mixture provided by Sauter and Stepper GmbH. The females regularly deposited eggs on stalks at the sealing of the container. Twice a week the flies were transferred to a new container and the stalks were gently harvested by the use of tweezers. The necking on the natural stalk seen in FIG. 2D is related to stressing the stalk at relative humidity higher than 30% or under water. This phenomenon leads to a loss of rigidity in the necked parts accompanied by a transition from cross-beta to parallel beta structure (Parker and Rudall, 1957). Such necking was not observed with the artificial stalk.

The artificial stalks have a smooth surface similar to those of natural stalks (FIGS. 2C and 2D). The artificial stalks had an average diameter of 10 μm and had a similar rigidity as the natural stalks. Cross sections of the stalks showed some porosity, which leads to a slight overestimation of the cross sectional area of the stalks and thus to reduced stress values calculated by the outer diameter.

Figure 3:
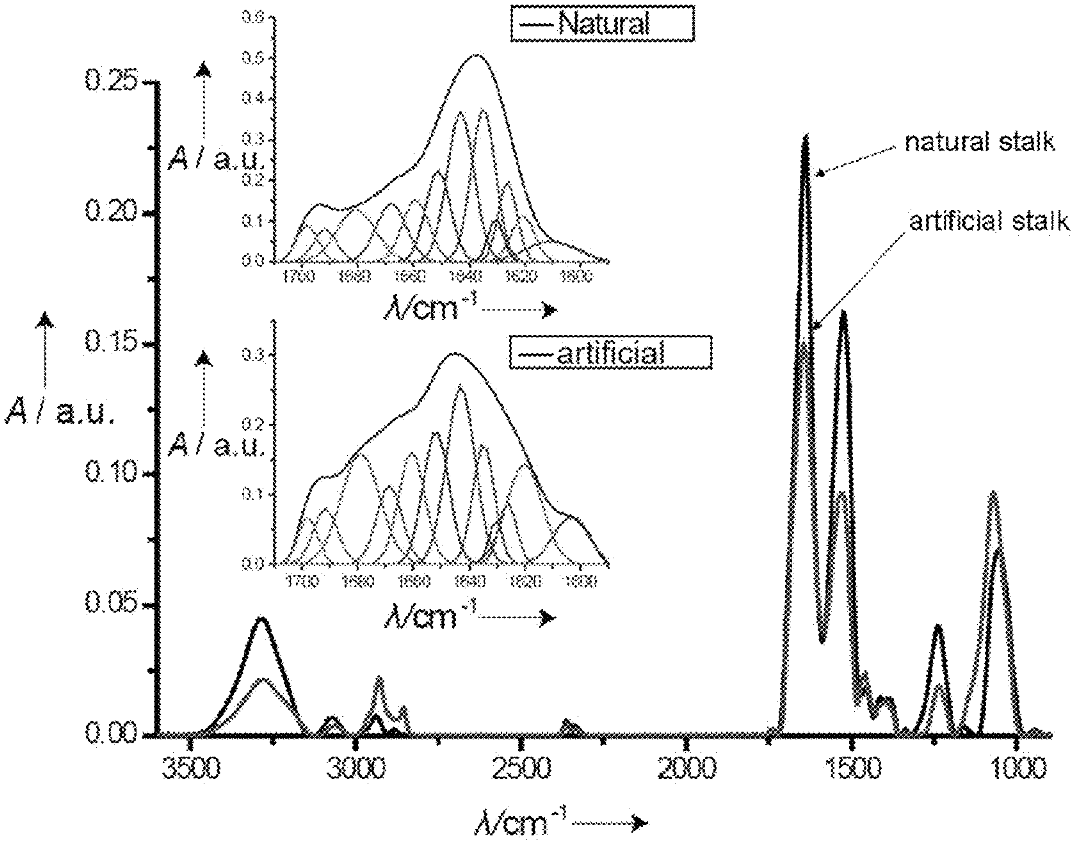
FIG. 3: FTIR absorbance spectra of natural and artificial stalks; insets show the Fourier self deconvoluted amide I region of natural and artificial stalks.

Both artificial and natural stalks were structurally analysed using FTIR (FIG. 3). For secondary structure analysis Fourier self-deconvolution of the amide I region (Hu et al. 2006) was performed indicating a lower beta-sheet content in artificial stalks in comparison to the natural ones (Table 1). The alpha helical content in both stalks is quite low at 6-9%.

The poly (L-Alanine) NCα stretching vibration (Moore and Krimm, 1976) at a wavelength of 1167 $cm^{-1}$, as detected by polarized FTIR spectra measured at 0° and 90° of the stalk axis, indicates a strong orientation of the poly-Ala crystals perpendicular to the stalk axis for the natural egg stalks (Smol: −0.44). The engineered biopolymer does not contain poly-alanine sequences indicating that so far undetected poly-alanine rich proteins are critically involved in structural alignment in natural stalks. Therefore our approach is not meant to mimic the natural approach. It is rather a novel approach inspired by nature.

TABLE 1

Secondary structure averaged from 12 natural and 18 artificial egg stalks (after post-treatment) measured individually using FTIR spectroscopy and calculated with Fourier self-deconvolution (Hu et al. 2006).

| secondary structure | natural egg stalk average [%] | standard deviation | artificial egg stalk average [%] | standard deviation |
|---|---|---|---|---|
| β-sheets | 40 | ±6 | 32 | ±3 |
| alpha-helices | 6 | ±4 | 9 | ±2 |
| turns | 24 | ±3 | 30 | ±3 |
| random coils | 30 | ±4 | 29 | ±1 |

Figure 4:
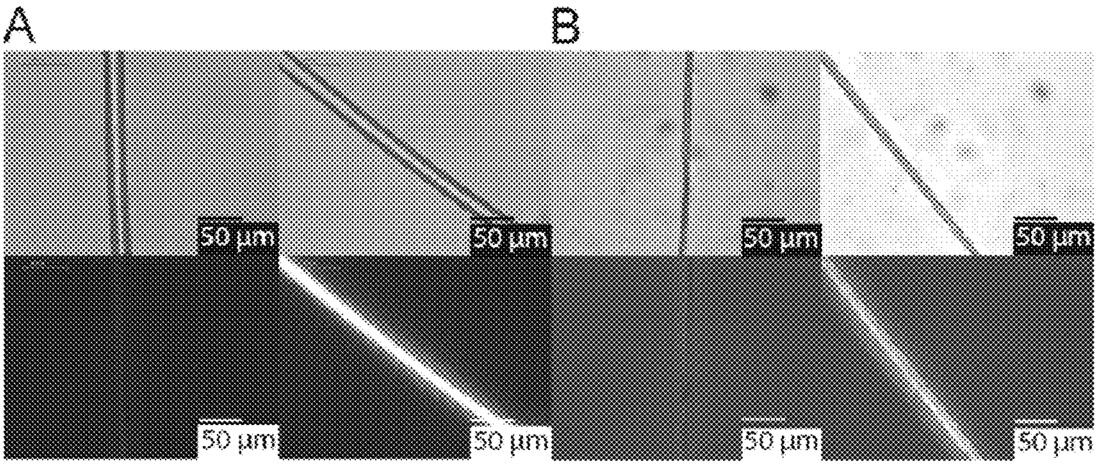
FIGS. 4A-4B.

Both the natural as well as the artificial stalks show birefringence (FIGS. 4A-B) based on anisotropy. The birefringence has a high intensity for the natural stalks based on highly ordered crystalline regions with beta sheets ordered perpendicular to the stalk axis, while the artificial stalks show weaker birefringence indicating less ordered structure in the stalks.

Figure 5:
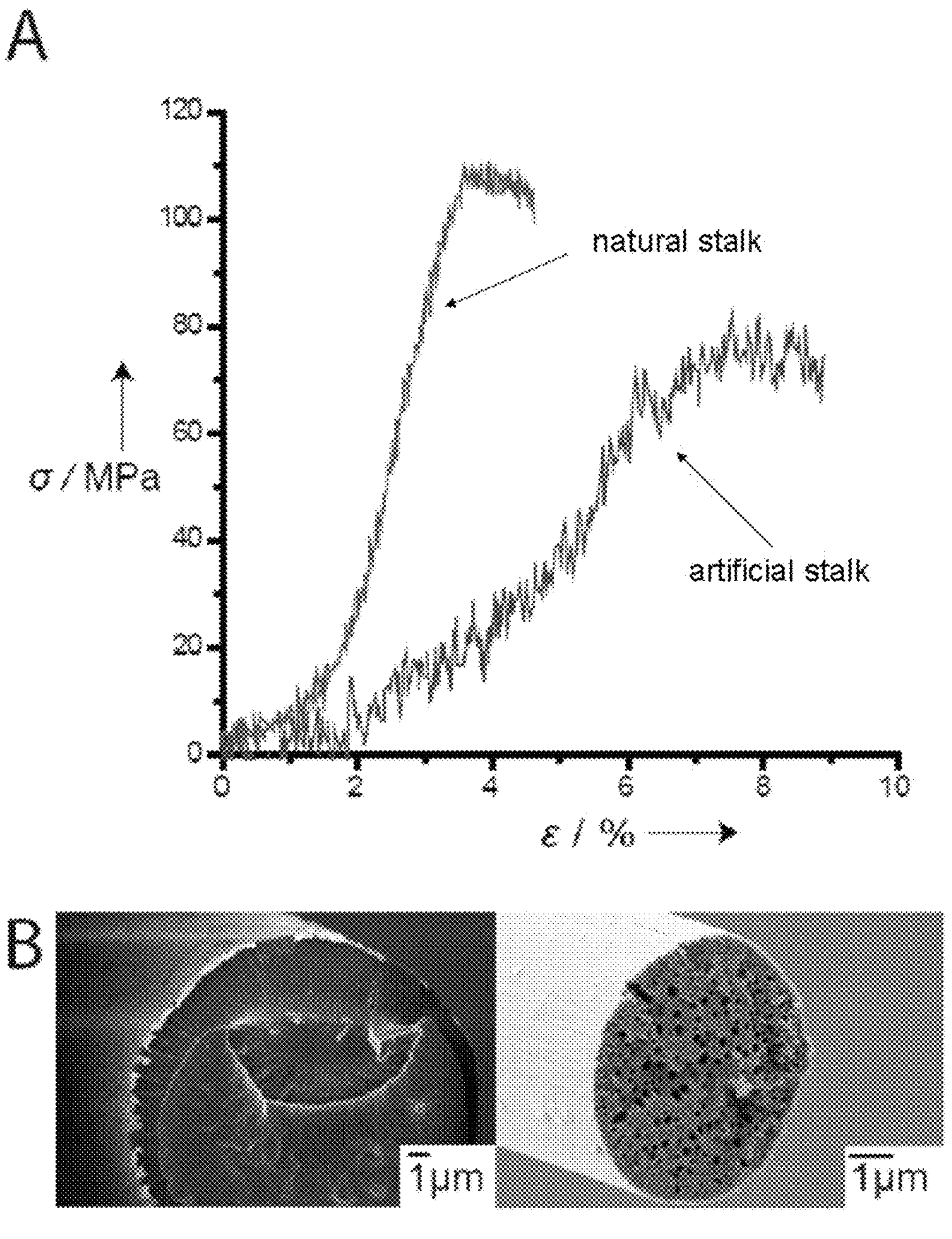
FIGS. 5A-5B.

Mechanical properties were analysed at an extension rate of 0.01 mm/s and a relative humidity (RH) of 30% and 70% RH at 22° C. Controlled humidity is highly important for tensile testing of biopolymers based on silk proteins (Schafer et al. 2008; Vehoff et al. 2007; Plaza et al. 2006). Stress strain curves of each of one of the best performing (strength) natural and artificial stalks are shown in FIG. 5A, and mechanical values are summarized in Table 2. The strength of the natural egg stalks measured under the chosen conditions is quite low with 68 MPa (30% RH) and 155 MPa (70% RH) if compared to the published values of 186 MPa to 375 MPa measured at 65% RH (Weisman et al. 2009; Hepburn et al. 1979). At 30% RH the stalks rupture at a strain of about 2%, while at 70% RH they rupture at a strain of 211%. The Young's modulus of natural egg stalks at 30% RH is 5.7 GPa, while the artificial egg stalk has about 40% of the stiffness (2.3 GPa). The tensile strength of the natural stalk is 55 MPa and that of the artificial stalk is about 79% of that value. The toughness of the artificial stalks at 30% RH is slightly higher than for the natural ones with 1.2 $MJ/m^3$, while at 70% RH the natural stalks have a toughness of 87 $MJ/m^3$.

TABLE 2

Tensile testing of natural and artificial egg stalks. Experiments were carried out at 30% and 70% relative humidity and at 22° C.

| | extensibility [%] | strength $\sigma_{max}$ [MPa] | Youngs modulus [MPa] | toughness [$MJ/m^3$] |
|---|---|---|---|---|
| natural egg stalk | | | | |
| 30% RH | 2 ± 1 | 68 ± 19 | 5777 ± 1257 | 1.2 ± 0.72 |
| 70% RH | 210 ± 100 | 155 ± 75 | 3175 ± 1016 | 87 ± 49 |
| literature values | | | | |
| 65% RH (Weisman et al. 2009) | 381 | 310 | | |
| 65% RH (Hepburn et al. 1979) | 249 | ~480 | | |
| artificial egg stalk | | | | |
| 30% RH | 5 ± 2 | 55 ± 14 | 2330 ± 850 | 1.76 ± 0.9 |
| 70% RH | 6 ± 3 | 25 ± 11 | 1012 ± 252 | 1.09 ± 0.59 |

Taking into account, that the cross section of the artificial stalk in contrast to the natural stalk is porous (a possible artefact coming from non-degassed HFA) (FIG. 5B), the strength can be recalculated, yielding 90% of the natural egg stalks strength.

As shown above, the first designed and recombinantly produced lacewing egg stalk biopolymer could be processed into artificial egg stalks with similar properties as natural stalks at 30% RH. The stalks show similar bending properties as the natural ones which may open applications for biopolymers where rigidity is of interest in the transversal direction. Further, the recombinant approach allows to deepen the understanding of the molecular structure-function relationship in such biopolymers.

Example 4

Production of Wet Spun Fibers of the Engineered Biopolymer of the Invention

It is possible to spin fibers of $N[AS]_8C$ solutions preferably in organic acids such as formic acid or organic solvents such as Hexafluoroisopropanol (HFIP) or Hexafluoroacetone (HFA). As a coagulation bath solvents can be used such as e.g. methanol, ethanol, isopropanol or aqueous solutions of kosmotropic salts, such as e.g.: sulfate or phosphate salts, in different concentrations.

The spinning dope containing 7 to 12% of $N[AS]_8C$ is extruded through a small needle into the coagulation bath with a distinct speed. The coagulation bath may range in concentrations between 50%-to 100% for the alcohol or alternatively up to 2 M for kosmotropic salts.

Figure 9:
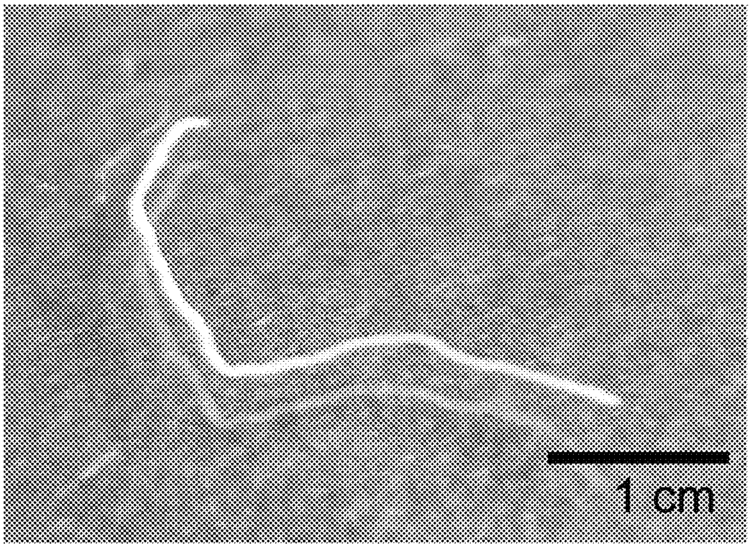
FIG. 9: Wet spun fiber of 10% N[AS]$_8$C in formic acid solution spun into a methanol bath.

The resulting fiber can be post spun immediately in the coagulation bath or in a special post spinning solution such as water or additional coagulation solutions (e.g.: 70% isopropanol in $H_2O$). Surprisingly these fibers are not stiff. An example of a wet spun fibre is shown in FIG. 9.

Example 5

Production of Films of the Engineered Biopolymer of the Invention

Films can be cast out of various solvents such as HFA, HFIP, formic acid and others or mixtures of these with water. Protein concentrations may range from 0.1 mg/ml to 50 mg/ml, the solubility limit depending on the respective solvent. As a substrate, various surfaces might be used, such as e.g. polystyrene, Teflon, glass, polyurethane or quartz glass. Films can simply be cast onto such a surface and are then left to dry. After evaporation of the solvent, the biopolymers form films that can easily be peeled off the surface. The relative humidity at which the solvents evaporate is preferably controlled to get reproducible film properties.

Since water insolubility is preferred for many applications of biopolymer films, incubating the films as cast with for example 1 M potassium phosphate, methanol, ethanol, isopropanol or others may be carried out, which results in the conversion of films into a water insoluble state. In addition, some applications of biopolymer films require a functionalization of the surface of the film, e.g. with small organic molecules as well as biological macromolecules like proteins, such as for example fluorescent proteins or enzymes, such as e.g. β-galactosidase. To achieve the desired functionalization, surface exposed carboxyl groups of the biopolymer have to be activated, for example using 1-ethyl-3-(3-dimethylaminopropyl)carbodiimide (EDC) or similar compounds. The films may then be incubated with for example ethylenediamine to form an amide. The remaining free amino group of ethylenediamine can subsequently be coupled to the required molecules, resulting in the efficient covalent linkage of the molecule via formation of a stable thiourea derivative. Alternatively, incubation with molecules that have primary amines accessible on their surface, such as e.g. β-galactosidase, may be carried out directly with EDC-activated biopolymer films, thus leading to the formation of amide bonds between carboxyl groups of the biopolymer and primary amines (e.g. from lysine residues) of the molecule. Subsequently, the films may be washed several times.

Figure 10:
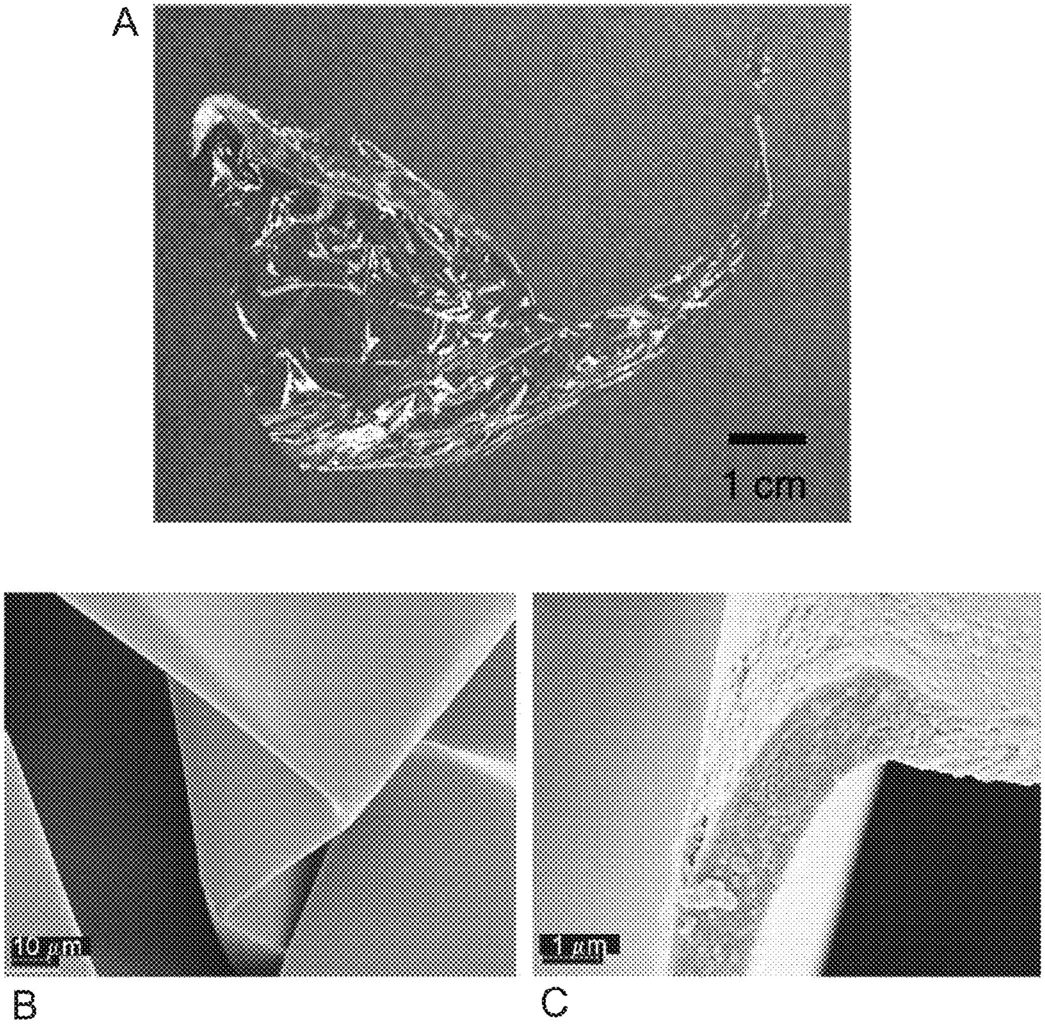
FIGS. 10A-10C: N[AS]$_8$C—Film cast from an HFIP solution on polystyrene and peeled off. Photograph (top) and SEM pictures (middle and bottom)

FIGS. 10A-100 shows a $N[AS]_8C$-film which was cast from an HFIP solution on polystyrene and peeled off.

Example 6

Cell Attachment to $N[AS]_8C$ Films

Fibroblasts show a very poor attachment onto films cast from formic acid. The adhesion is comparable to that to the negative control (untreated cell culture plates; Nunc, Germany). Attachment can be tuned by adding water to the formic acid or by varying the film thickness.

For cell culture experiments, BALB/3T3 mouse fibroblasts (European Collection of Cell Cultures) were cultured in DMEM media (Biochrom, Berlin, Germany) supplemented with 10% fetal bovine serum (Biochrom, Berlin, Germany), 1.0% (v/v) GlutaMAX (Gibco, Grand Island, USA), and 0.1% (v/v) gentamicin sulfate (Sigma-Aldrich, Seelze, Germany). Cell viability was determined by the Trypan blue exclusion method (Sigma-Aldrich, Ayrshire, UK). Cells were maintained in an incubator with controlled atmosphere (5.0% CO2, 95% humidity) (Haereus, Hanau, Germany).

For analysis of cell adhesion, films were directly cast in non-treated cell culture plates (Nunc, Langenselbold, Germany). As a positive control for cell adhesion and proliferation, cells were seeded on treated cell culture plates (BD Falcon, Franklin Lakes, USA).

Adhesion tests were carried out after seeding of 100 000 cells/$cm^2$ in 1.0 ml of cell culture media using single wells of a 24 well plate. After incubation for 4 h, media were changed and cells were washed twice with PBS (Sigma-Aldrich, St. Louis, USA) in order to remove dead or non-adherent fibroblasts. After washing, cells were additionally incubated for 2.5 h in the presence of the dye cell-titter blue (Promega, Madison, USA), at a concentration of 10% (v/v). The number of attached cells was determined by spectroscopically measuring the transformation of resazurin (blue, no fluorescent) into resorufin (red fluorescence, λex 530 nm; λem 590 nm). Fluorescence emission was measured in a plate reader (Mythras LB 940; Berthold, Bad Wildbad, Germany), with a counting time of 0.5 s, using a Halogen lamp (75 W). For excitation filter F530 and for emission filter F600 were used.

Example 7

Production of Structured Films and Surfaces for Guided/Directed Cell Growth

Structured protein layers/films can be deposited on cell culture plates and various other substrates with a defined surface topology. Different techniques can be used to achieve this, for example Micro contact printing (Zhang 2011) or filling of micro channels of PDMS templates by capillary forces. Since cells show low adhesion to $N[AS]_8C$ they align along such structured templates in contact with the other substrate (e.g. not silk-covered surface of the culture plate), and aligned cells can be used for artificial nerve regeneration or muscle cell growth.

Figure 11:
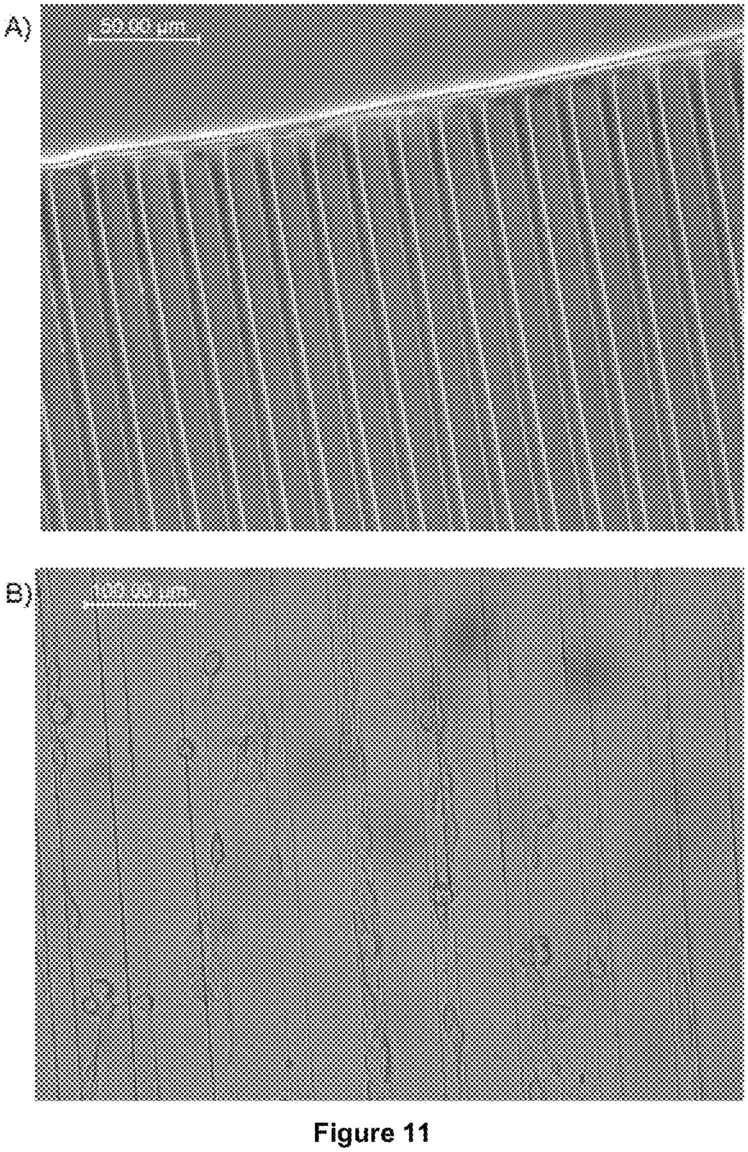
FIGS. 11A-11B.

Structures were made by placing a PDMS template containing 50 μm wide channels in a cell culture plate (channels downside) and depositing a droplet of silk solution (1% N[AS]8C in formic acid) at one side with open channels. Capillary forces soak the protein solution into the channels where the solution is allowed to dry over night. The PDMS template is removed carefully to not destroy the structure. FIG. 11A shows an example of such a structure. Fibroblasts were seeded with a density of 4500 cells/$cm^2$ in the culture plate and cultured at 37° C. and 5% $CO_2$ in a DMEM (Dulbecco's Minimal Essential Medium) media supplemented with 10% (v/v) FCS (fetal calf serum). As is shown in FIG. 11B, cells grow and spread only on the cell culture plate and orientate along the structured lines.

Example 8

Production of Spheres from the Engineered Biopolymer of the Invention

Figure 12:
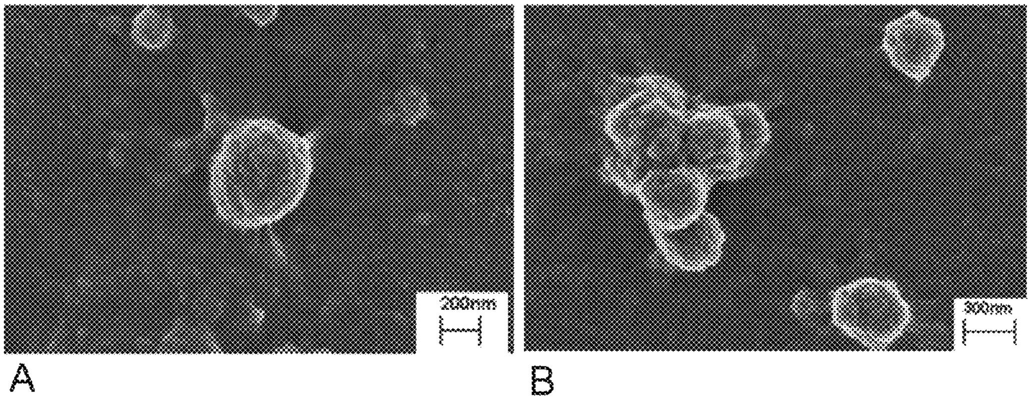
FIGS. 12A-12B: SEM pictures of microspheres made of N[AS]$_8$C.

Spheres can be created by precipitation of protein out of solution. For this purpose, $N[AS]_8C$ is dissolved in formic acid in concentrations varying from 0.1% to 10%. The solution may be diluted to lower concentrations with water. The addition of kosmotropic salts or oil causes the formation of spheres, as shown in FIGS. 12A-12B.

Example 9

Production of a Spring from the Engineered Biopolymer of the Invention

Figure 13:
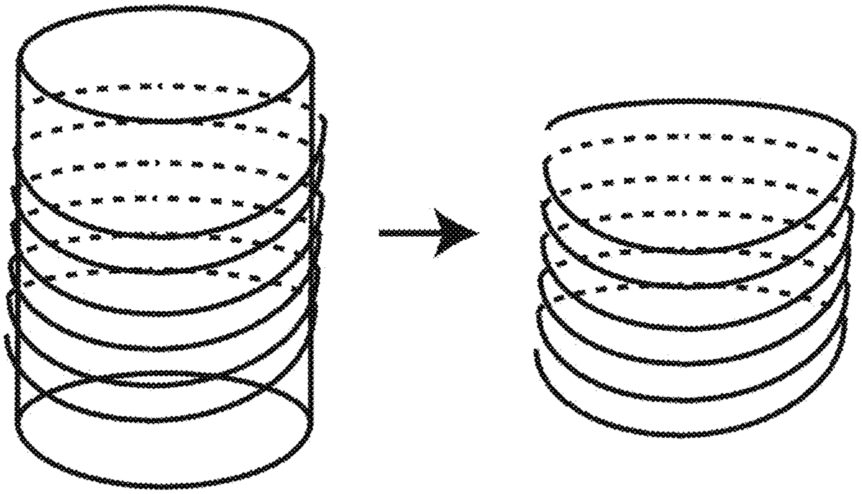
FIG. 13: Schematic representation of the production of a spring out of N[AS]$_8$C.

An artificial stalk (see example 3 above) can be spooled on a rod in a spiral shape during processing. After hardening, the spiral can be taken off the rod as a spring. See FIG. 13 for an illustration.

Example 10

Production of Nonwoven Mats by Electro Spinning

Nonwovens can be generated out of various highly concentrated $N[AS]_8C$ solutions using solvents such as HFIP, HFA or aqueous solutions. For example, 7% to 12% of $N[AS]_8C$ is dissolved in HFIP and extruded through a contacted needle on which a high electric field is applied.

Using this technique, thin fibres (50 nm up to about one μm) can be produced and deposited as nonwoven mats.

Example 11

Production of Films

Easy obtainable biopolymer-structures are films (FIGS. 14A-14F) because it is only necessary to dissolve the protein, and cast a film onto a substrate and let the solvent evaporate.

Therefore, 1% (w/v) $N[AS]_8C$ was dissolved in HFIP (Hexafluoroisopropanol) or formic acid. Both solutions were cast on polystyrene. After drying, the films could be peeled off the substrate or be first post-treated by covering with methanol or over-night at storage at 60° C. and 50% relative humidity. Secondary structure was analysed using a FTIR. For scanning electron microscopy the samples were glued on aluminium stubs and were sputter-coated with platinum. Images were obtained using a Zeiss 1530.

Figure 14:
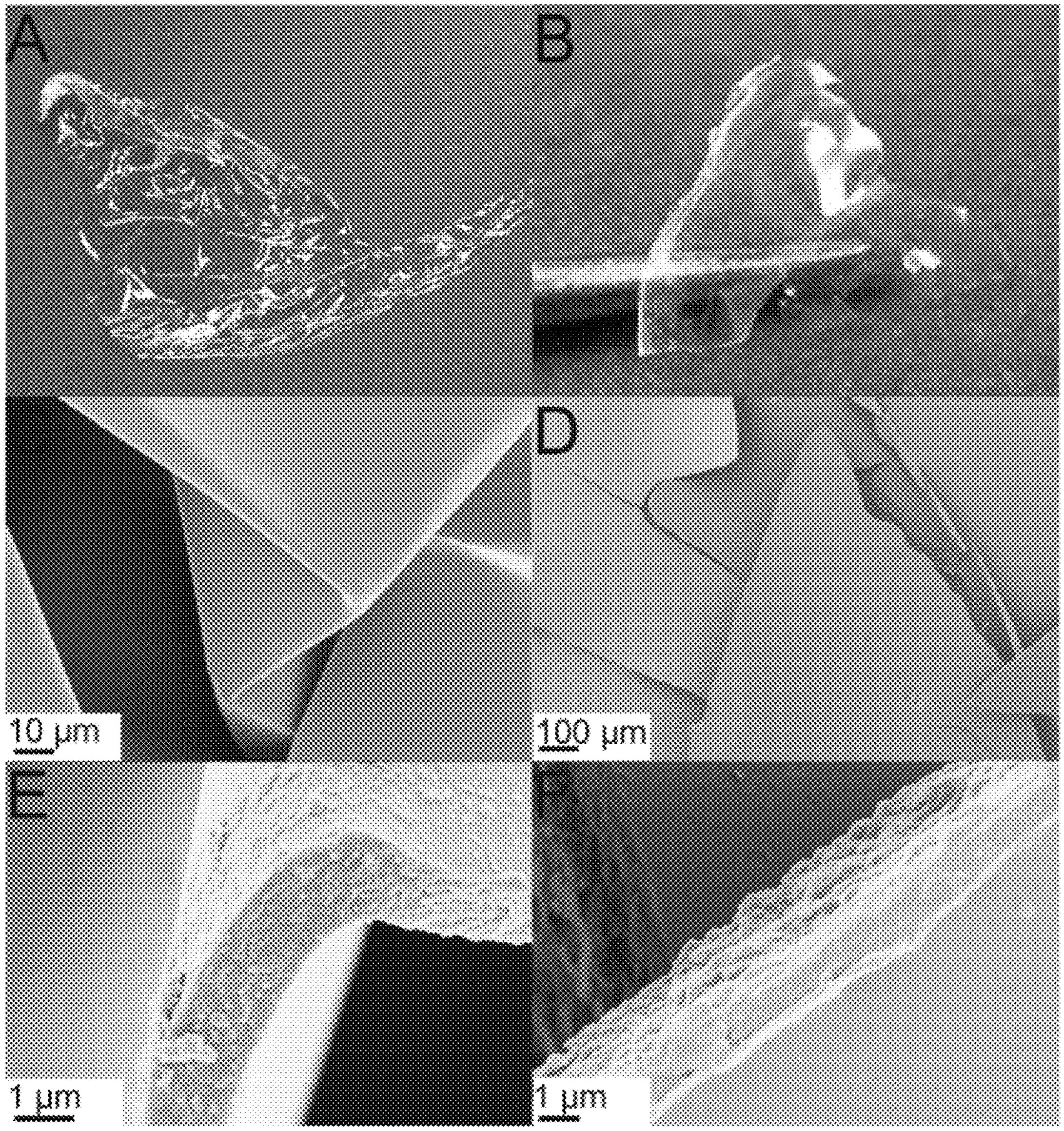
FIGS. 14A-14F: N[AS]$_8$C-films. Figures A, C, and E are cast from HFIP; Figures B, D, and F are cast from formic acid. C—F: Scanning electron microscopic pictures of film surfaces and breaking edges.
Figure 15:
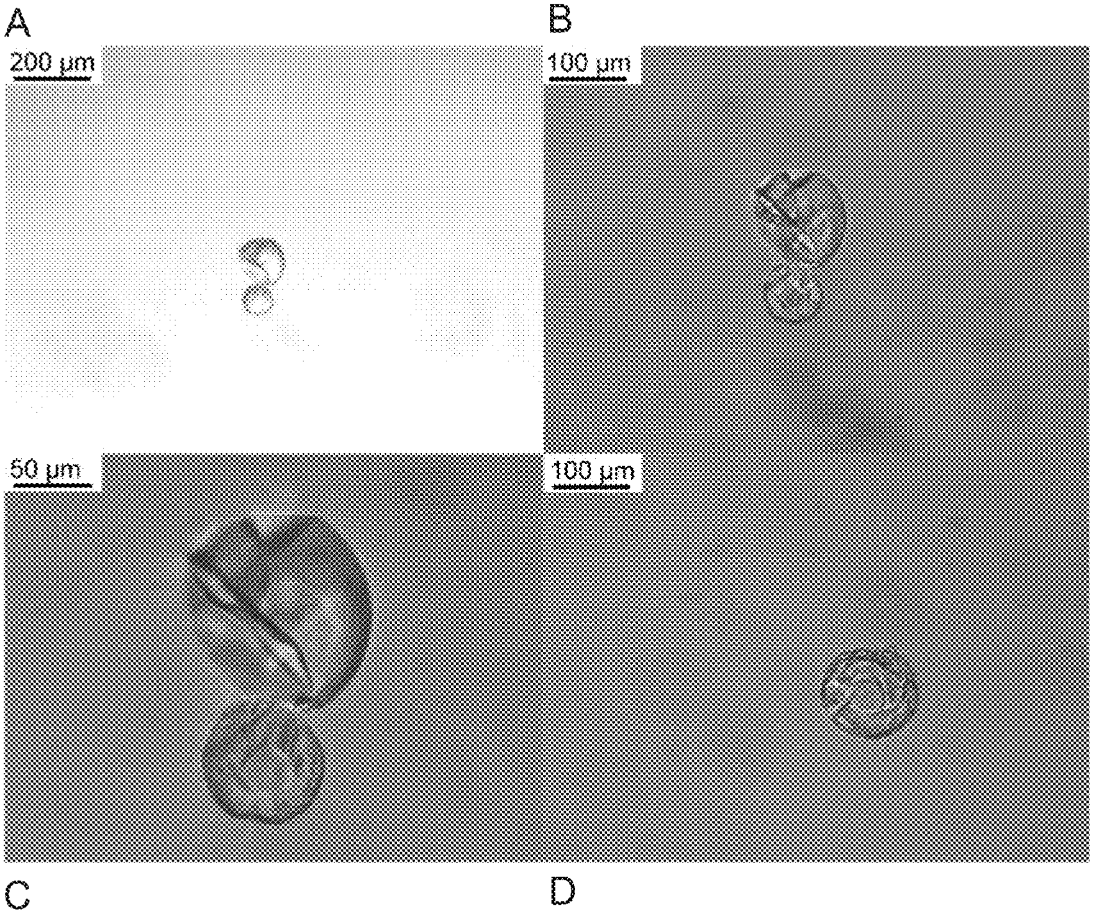
FIGS. 15A-15D: Capsules made of N[AS]$_8$C produced by interfacial polymerisation.

Films cast from formic acid were more brittle (FIGS. 14B, 14D, and 14F) and were water insoluble directly after drying. They had a β-sheet content of approximately 58%. In contrast films from HFIP (FIGS. 14A, 14C, 14E) were water soluble and therefore had to be post-treated. Without post-treatment they had a β-sheet content of 5% which increased due to aging to around 20% (after 4 days). Overnight heat treatment of the films at 60° C. and 50% relative humidity led to around 40% β-sheet content. Slightly higher values could be obtained by treating the film with methanol. Such treated films were stable in water. SEM images of methanol treated films show a smooth surface. The breaking edge of films cast from formic acid show a layered structure (FIG. 14F). This layers might be related to $N[AS]_8C$ folding into sheets with a thickness of 2.5 nm (without terminal domains)/40 nm (with terminal domains), or multiples thereof, which one would expect from the structure of the natural proteins in an egg stalk.

Example 12

Production of Capsules

Capsules were produced using protein self-assembly at a water oil interface.

Therefore, 1.5 mg $N[AS]_8C$ were dissolved per 1 ml 6 M guanidinium thiocyanate solution. Afterwards the solution was dialysed against 10 mM Tris/HCl; pH 7.5; 5 mM β-mercaptoethanol using a dialysis tube with a cut-off of 6-8 kD. 5 μl of this solution were transferred into 500 μl M100 silicon oil and subsequently were shaken for 45 s. After emulsification (shaking) a protein layer builds up at the oil-water interface of the water droplets. To transfer the capsules in an aqueous environment the silicon oil was supplemented with 70% ethanol and the oil mixture was removed. Repeating this step several times led to oil free capsules which were washed with water afterwards. Finally the capsules were observed in a light microscope (see FIGS. 15A-15D).

The capsules shrunk during ethanol treatment due to osmosis and did not swell afterwards in water.

This indicates a completely protein layer on the surface with semipermeable properties.

Example 13

Production of Hydrogels

Figure 16:
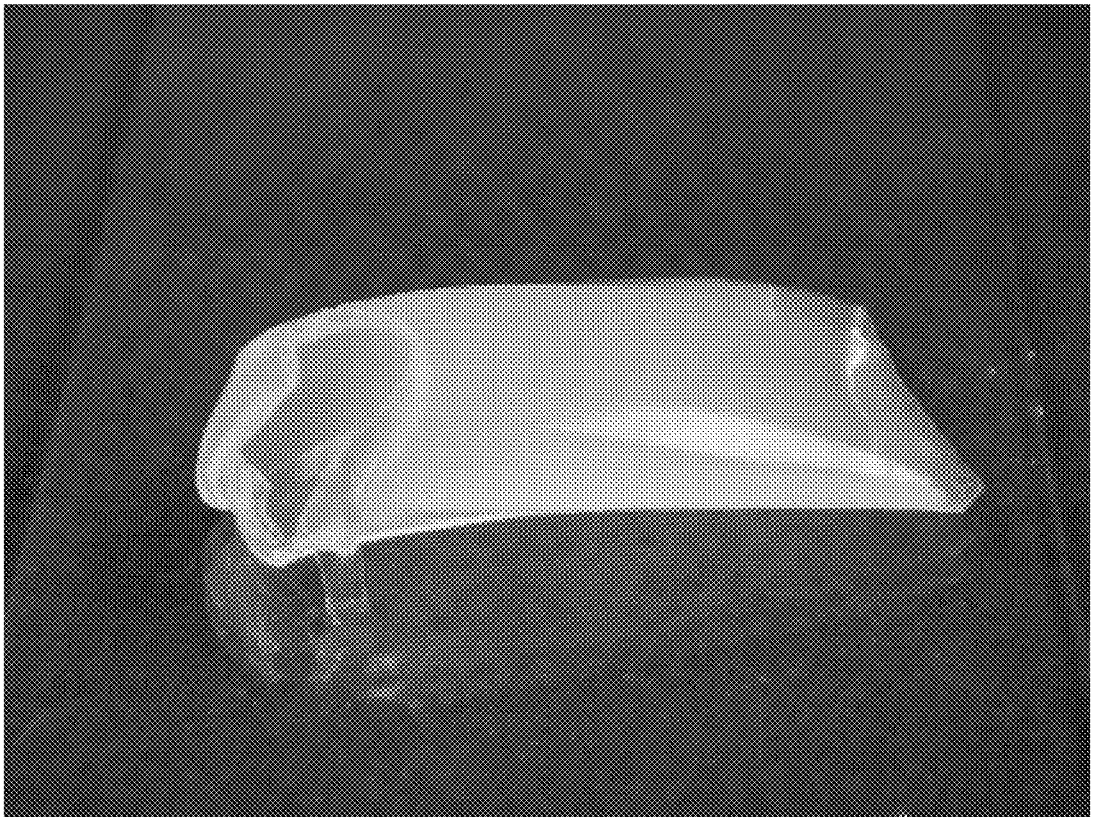
FIG. 16: Hydrogel of 3% (w/v) N[AS]$_8$C.
Figure 17:
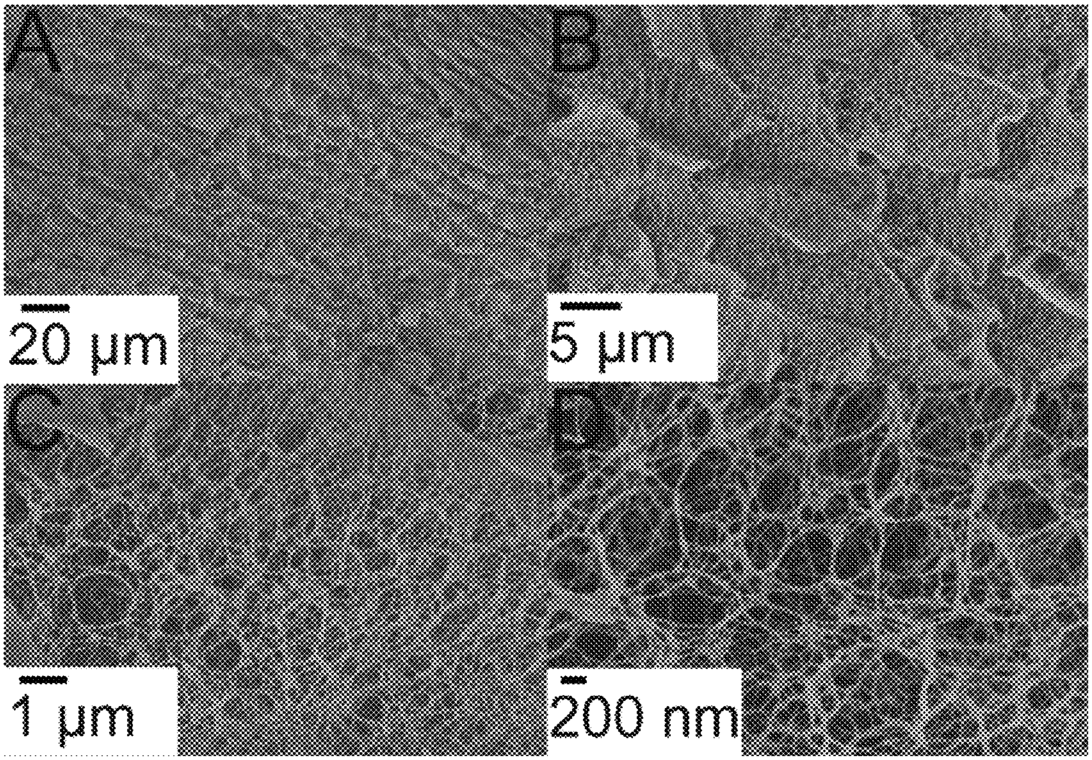
FIGS. 17A-17D: SEM (scanning electron microscopy) pictures of a foam produced by freeze drying of a 3% (w/v) N[AS]$_8$C hydrogel.

To produce hydrogels, 3% (w/v) $N[AS]_8C$ was dissolved in guanidinium thiocyanate. During dialysis against 10 mM Tris/HCl; pH 7.5 a hydrogel forms (FIG. 16).

The hydrogel formation is forced by a nucleation-aggregation mechanism of nanofibrils in the solution which build a stable network.

Example 14

Production of Foams

Foams were fabricated by freeze drying of hydrogels.

Hydrogels out of 3% N[AS]8C were fabricated as described above. After freezing in liquid nitrogen the hydrogels were lyophilised resulting in foams. Samples of the foam were glued on aluminium stubs and were sputter-coated with platinum. Images were obtained using a Zeiss 1530.

Freeze drying of a 3% $N[AS]_8C$ hydrogel led to a stable foam like structure (FIG. 16). Interestingly SEM (scanning electron microscopy) pictures revealed differences from foams produced the same way out of engineered spider silk proteins. The foam has a pore size of 6 to 17 μm. Surprisingly the pores are filled with a 3D mesh of fibres in the nanometer scale revealing a pore size of 200-400 nm (FIG. 16 higher magnifications).

These fibrous structures which are embedded in the stable porous scaffold might be suitable as a filter material.

Possible applications for the recombinant lacewing egg stalk protein $N[AS]_8C$ vary depending on their morphology. Stalks for example might be useful in a composite material to provide rigidity to the resulting material. Capsules could be used to encapsulate enzymes or drugs for controlled drug release. Hydrogels might be used in wound healing/dressing or cell culture. Foams are a scaffold which might promote cell growth in a three dimensional shape for tissue engineering or as a filter material. Here the mesh in the pores might be an interesting feature exceeding other materials.

REFERENCES

C. Allmeling, A. Jokuszies, K. Reimers, S. Kall, P. M. Vogt, Journal of Cellular and Molecular Medicine 2006, 10, 770.

C. Allmeling, A. Jokuszies, K. Reimers, S. Kall, C. Y. Choi, G. Brandes, C. Kasper, T. Scheper, M. Guggenheim, P. M. Vogt, Cell Prolif 2008, 41, 408.

C. L. Craig, Annual review of entomology 1997, 42, 231.

A. Hagenau, P. Papadopoulos, F. Kremer, T. Scheibel, J Struct Biol 2011, 175, 339.

J. G. Hardy, L. M. Römer, T. R. Scheibel, Polymer 49 (2008) 4309-4327.

H. R. Hepburn, H. D. Chandler, M. R. Davidoff, Insect Biochemistry 1979, 9, 69.

X. Hu, D. Kaplan, P. Cebe, Macromolecules 2006, 39, 6161.

D. Huemmerich, C. W. Nelsen, S. Quedzuweit, J. Oschmann, R. Rudolph, T. Scheibel, Biochemistry 2004, 43, 13604.

D. J. Korz, U. Rinas, K. Hellmuth, E. A. Sanders, W. D. Deckwer, Journal of Biotechnology 1995, 39, 59.

A. Lammel, M. Schwab, M. Hofer, G. Winter, T. Scheibel, Biomaterials 2011, 32, 2233.

A. Leal-Egana, T. Scheibel, Biotechnology and Applied Biochemistry 2010, 55, 155.

F. Lucas, J. T. B. Shaw, S. G. Smith, Nature 1957, 179, 906.

W. H. Moore, S. Krimm, Biopolymers 1976, 15, 2465.

K. Numata, D. L. Kaplan, Advanced Drug Delivery Reviews 2010, in press.

K. D. Parker, K. M. Rudall, Nature 1957, 179, 905.

G. R. Plaza, G. V. Guinea, J. Perez-Rigueiro, M. Elices, Journal of Polymer Science Part B-Polymer Physics 2006, 44, 994.

A. Schafer, T. Vehoff, A. Glisovic, T. Salditt, European Biophysics Journal with Biophysics Letters 2008, 37, 197.

K. Spiess, A. Lammel, T. Scheibel, Macromolecular Biosciences 2010, 10, 998.

T. Vehoff, A. Glisovic, H. Schollmeyer, A. Zippelius, T. Salditt, Biophysical Journal 2007, 93, 4425.

C. Vendrely, T. Scheibel, Macromolecular Bioscience 2007, 7, 401.

S. Weisman, S. Okada, S. T. Mudie, M. G. Huson, H. E. Trueman, A. Sriskantha, V. S. Haritos, T. D. Sutherland, Journal of Structural Biology 2009, 168, 467.

X.-X. Xia, Z.-G. Qian, C. S. Ki, Y. H. Park, D. L. Kaplan, S. Y. Lee, Proceedings of the National Academy of Sciences 2010, 107, 14059.

J. M. Yao, H. Masuda, C. H. Zhao, T. Asakura, Macromolecules 2002, 35, 6.

J-T. Zhang, J. Nie, M. Mühlstädt, H. Gallagher, O. Pullig, K. D. Jandt, Advanced Functional Materials 2011, 21, 4079-4087

What is claimed is:

1. A biopolymer comprising at least two repeats, wherein the at least two repeats within the biopolymer are identical or different, of an amino acid sequence comprising:

(i) the amino acid sequence of SEQ ID NO: 1;

(ii) an amino acid sequence having at least 97% sequence identity to the amino acid sequence of SEQ ID NO: 1, wherein a fiber formed from the biopolymer comprising said amino acid sequence has a toughness of at least 700 $J/m^3$;

(iii) the amino acid sequence encoded by the nucleic acid molecule of SEQ ID NO: 2;

(iv) an amino acid sequence having at least 97% sequence identity to the amino acid sequence of SEQ ID NO: 1 encoded by a nucleic acid sequence that hybridizes under highly stringent conditions to the complementary strand of the nucleic acid sequence of SEQ ID NO: 2, wherein said highly stringent conditions comprise:
(iva) an overnight incubation at 65° C. in 4×SSC followed by washing at 65° C. in 0.1×SSC for one hour, or
(ivb) an overnight incubation at 42° C. in a solution comprising 50% formamide, 5×SSC, 50 mM sodium phosphate (pH 7.6), 5×Denhardt's solution, 10% dextran sulphate, and 20 μg/ml denatured, sheared salmon sperm DNA, followed by washing in 0.1-0.5× SSC at 55-65° C. for 5 to 20 min,
wherein a fiber formed from the biopolymer comprising said amino acid sequence has a toughness of at least 700 $J/m^3$; or
(v) a variant of the amino acid sequence of (i), wherein the variant differs from the amino acid sequence of (i) in 1 amino acid, wherein the variations are selected from the group consisting of substitutions, deletions, insertions and/or additions and wherein a fiber formed from the biopolymer comprising said variant of the amino acid sequence of (i) has a toughness of at least 700 $J/m^3$.

2. The biopolymer of claim 1, further comprising an N- and/or C-terminal polypeptide.

3. The biopolymer of claim 2, wherein the N-terminal polypeptide is selected from the group consisting of:
(i) an amino acid sequence comprising the amino acid sequence of any one of SEQ ID NO: 3 to SEQ ID NO: 18;
(ii) an amino acid sequence having at least 90% sequence identity to the amino acid sequence of (i), wherein a fiber formed from the biopolymer comprising said amino acid sequence has a toughness of at least 700 $J/m^3$;
(iii) an amino acid sequence having at least 95% sequence identity to the amino acid sequence of (i), wherein a fiber formed from the biopolymer comprising said amino acid sequence has a toughness of at least 700 $J/m^3$;
(iv) an amino acid sequence encoded by a nucleic acid molecule comprising the sequence of any one of SEQ ID NO: 19 to SEQ ID NO: 34;
(v) an amino acid sequence encoded by a nucleic acid sequence that hybridizes under highly stringent conditions to the complementary strand of a nucleic acid sequence of (iv), wherein said highly stringent conditions comprise:
(va) an overnight incubation at 65° C. in 4×SSC followed by washing at 65° C. in 0.1×SSC for one hour, or
(vb) an overnight incubation at 42° C. in a solution comprising 50% formamide, 5×SSC, 50 mM sodium phosphate (pH 7.6), 5×Denhardt's solution, 10% dextran sulphate, and 20 μg/ml denatured, sheared salmon sperm DNA, followed by washing in 0.1-0.5× SSC at 55-65° C. for 5 to 20 min,
wherein a fiber formed from the biopolymer comprising said amino acid sequence has a toughness of at least 700 $J/m^3$; and
(vi) a variant of the amino acid sequence of (i), wherein the variant differs from the amino acid sequence of (i) in 1 to 5 amino acids and wherein the variations are selected from the group consisting of substitutions, deletions, insertions and/or additions and wherein a fiber formed from the biopolymer comprising said variant of the amino acid sequence of (i) has a toughness of at least 700 $J/m^3$.

4. The biopolymer of claim 2, wherein the C-terminal polypeptide is selected from the group consisting of:
(i) an amino acid sequence comprising the amino acid sequence of any one of SEQ ID NO: 35 to SEQ ID NO: 50;
(ii) an amino acid sequence having at least 90% sequence identity to the amino acid sequence of (i), wherein a fiber formed from the biopolymer comprising said amino acid sequence has a toughness of at least 700 $J/m^3$;
(iii) an amino acid sequence having at least 95% sequence identity to the amino acid sequence of (i), wherein a fiber formed from the biopolymer comprising said amino acid sequence has a toughness of at least 700 $J/m^3$;
(iv) an amino acid sequence encoded by a nucleic acid molecule comprising the sequence of any one of SEQ ID NO: 51 to SEQ ID NO: 66;
(v) an amino acid sequence encoded by a nucleic acid sequence that hybridizes under highly stringent conditions to the complementary strand of a nucleic acid sequence of (iv), wherein said highly stringent conditions comprise:
(va) an overnight incubation at 65° C. in 4×SSC followed by washing at 65° C. in 0.1×SSC for one hour, or
(vb) an overnight incubation at 42° C. in a solution comprising 50% formamide, 5×SSC, 50 mM sodium phosphate (pH 7.6), 5×Denhardt's solution, 10% dextran sulphate, and 20 μg/ml denatured, sheared salmon sperm DNA, followed by washing in 0.1-0.5× SSC at 55-65° C. for 5 to 20 min;
wherein a fiber formed from the biopolymer comprising said amino acid sequence has a toughness of at least 700 $J/m^3$; and
(vi) a variant of the amino acid sequence of (i), wherein the variant differs from the amino acid sequence of (i) in 1 to 5 amino acids and wherein the variations are selected from the group consisting of substitutions, deletions, insertions and/or additions and wherein a fiber formed from the biopolymer comprising said variant of the amino acid sequence of (i) has a toughness of at least 700 $J/m^3$.

5. A nucleic acid molecule encoding the biopolymer of claim 1.

6. A vector comprising the nucleic acid molecule of claim 5.

7. A non-human host transformed with the vector of claim 6.

8. The non-human host of claim 7, wherein the host is a cell.

9. A method for the production of a biopolymer according to claim 1, comprising culturing a non-human host cell under suitable conditions and isolating the biopolymer produced.

10. Foams, films, gels, coatings, particles, capsules, springs or nonwovens, preferably nonwoven mats, comprising the biopolymer according to claim 1.

11. Fibres comprising the biopolymer of claim 1.

12. A method of producing (a) fibre(s), comprising
(i) dissolving the biopolymer of claim 1 or obtained by the method of claim 9 in a solvent thereby obtaining a solution comprising said biopolymer, and
(iia) extracting (a) fibre(s) from the solution of (i),
(iib) extruding (a) fibre(s) from the solution of (i), or
(iic) spinning (a) fibre(s) out of the solution of (i).

13. The method of claim 12, wherein the solvent is an organic solvent or an organic acid.

14. The method of claim 13, wherein the organic solvent is Hexafluoroisopropanol (HFIP) or Hexafluoroacetone (HFA) or wherein the organic acid is formic acid.

15. The method of claim 12, wherein the fibre(s) is (are) extruded in a coagulation bath.

16. The method of claim 15, wherein the coagulation bath comprises methanol, ethanol, isopropanol, or an aqueous solution of kosmotropic salts, preferably sulfate or phosphate salts.

17. A pharmaceutical composition comprising the biopolymer of claim 1.

18. A cosmetical composition comprising the biopolymer of claim 1.

19. A surface, paper, leather and/or textile processing composition comprising the biopolymer of claim 1.

20. A medical device comprising the biopolymer of claim 1.

21. The medical device of claim 20, wherein the medical device is selected from the group consisting of an implant, a wound closure system, prosthetic device, suture, stent, or surgical mesh.

22. A drug delivery system comprising the biopolymer of claim 1.

23. A biopolymer comprising at least two repeats, wherein the at least two repeats within the biopolymer are identical or different, of an amino acid sequence comprising:

(i) the amino acid sequence of SEQ ID NO: 1, or (ii) a variant of the amino acid sequence of (i), wherein the variant differs from the amino acid sequence of (i) in 1 amino acid, wherein the amino acid variation is according to formula I:

(SEQ ID NO: 67)

Gly-Ser-$X_1$-$X_2$-Ala-$X_3$-Ser-$X_4$-$X_5$-Ser-$X_6$-Ala-$X_7$-Ala-$X_8$-Lys-$X_9$-$X_{10}$-Ala-$X_{11}$-Ala-$X_{12}$-Ser-$X_{13}$-$X_{14}$-Ser-Thr-Ala-$X_{15}$-Ala-Ser-Lys-Gly-Ser-Ala-$X_{16}$-Ala-$X_{17}$-Ser-$X_{18}$-$X_{19}$-Ser-Thr-Ala-$X_{20}$-Ala-$X_{21}$-Lys (formula I)

wherein:

$X_1$ is selected from the group consisting of Ala and Ser;

$X_2$ and $X_3$ are each independently selected from the group consisting of Gly, Ser, Thr and Val;

$X_4$ is selected from the group consisting of Asn, Gly, Gln and Asp;

$X_5$, $X_{13}$, $X_{14}$, $X_{18}$ and $X_{19}$ are each independently selected from the group consisting of Gly and Asn;

$X_6$, $X_{11}$, $X_{12}$, $X_{15}$, $X_{16}$, and $X_{20}$ are each independently selected from the group consisting of Gly, Ser, Thr, Ala and Val;

$X_7$ is selected from the group consisting of Ser, Thr and Ala;

$X_8$ and $X_{21}$ are each independently selected from the group consisting of Ser and Thr;

$X_9$ is selected from the group consisting of Gly and Asp;

$X_{10}$ is selected from the group consisting of Ser, Ala and Gly; and $X_{17}$ is selected from the group consisting of Ser, Thr, Ala and Val;

and wherein at least one of $X_4$ and $X_5$ is Gly;

at least one of $X_{13}$ and $X_{14}$ is Gly; and at least one of $X_{18}$ and $X_{19}$ is Gly, and wherein a fiber formed from the biopolymer comprising said variant of the amino acid sequence of (i) has a toughness of at least 700 $J/m^3$.

* * * * *